United States Patent
Foster et al.

(10) Patent No.: US 11,162,115 B2
(45) Date of Patent: Nov. 2, 2021

(54) METHODS, SYNTHETIC HOSTS AND REAGENTS FOR THE BIOSYNTHESIS OF HYDROCARBONS

(71) Applicant: INV NYLON CHEMICALS AMERICAS, LLC, Wilmington, DE (US)

(72) Inventors: Alexander Brett Foster, Redcar (GB); Leonard Keith Pattenden, Redcar (GB); Jonathan David Rand, Redcar (GB); Ana Teresa dos Santos Brito Mendes Roberts, Redcar (GB); Andrew Shaw, Redcar (GB); Mark Paul Taylor, Redcar (GB)

(73) Assignee: INV Nylon Chemicals Americas, LLC, Wilmington, DE (US)

( * ) Notice: Subject to any disclaimer, the term of this patent is extended or adjusted under 35 U.S.C. 154(b) by 0 days.

(21) Appl. No.: 16/023,055

(22) Filed: Jun. 29, 2018

(65) Prior Publication Data

US 2019/0002927 A1   Jan. 3, 2019

Related U.S. Application Data

(60) Provisional application No. 62/527,551, filed on Jun. 30, 2017.

(51) Int. Cl.
   *C12P 5/00* (2006.01)
   *C12N 9/10* (2006.01)
   *C12N 1/20* (2006.01)
   *C12N 9/88* (2006.01)

(52) U.S. Cl.
   CPC ............... *C12P 5/007* (2013.01); *C12N 1/20* (2013.01); *C12N 9/1022* (2013.01); *C12N 9/88* (2013.01); *C12Y 202/01007* (2013.01); *C12Y 402/03027* (2013.01)

(58) Field of Classification Search
   None
   See application file for complete search history.

(56) References Cited

U.S. PATENT DOCUMENTS

| | | | |
|---|---|---|---|
| 1,016,748 A | 1/1919 | Conradie | C12P 5/007 |
| 1,053,878 A | 1/1920 | Kamionka et al. | C12P 5/007 |
| 4,605,620 A | 8/1986 | Andersch et al. | |
| 5,830,714 A | 11/1998 | Swaminathan et al. | 435/91.2 |
| 8,703,455 B2 | 4/2014 | Marliere | 435/167 |
| 8,741,612 B2 | 6/2014 | Campbell et al. | 435/167 |
| 9,297,026 B2 | 3/2016 | Koepke et al. | C12P 7/065 |
| 9,422,578 B2 | 8/2016 | Pearlman et al. | C12P 5/02 |
| 9,422,580 B2 | 8/2016 | Pearlman et al. | C12P 5/026 |
| 9,777,300 B2 | 10/2017 | Yeh et al. | C12P 7/6409 |
| 9,862,973 B2 | 1/2018 | Botes et al. | C12P 5/007 |
| 2003/0148416 A1 | 8/2003 | Berry | |
| 2008/0311640 A1 | 12/2008 | Cox et al. | 435/168 |
| 2009/0117629 A1 | 5/2009 | Schmidt-Dannert et al. | 435/134 |
| 2011/0053216 A1 | 3/2011 | Vermass | 435/69.1 |
| 2011/0160501 A1 | 6/2011 | Martin et al. | 585/14 |
| 2011/0165644 A1 | 7/2011 | Marliere | 435/167 |
| 2011/0300597 A1 | 12/2011 | Burk et al. | 435/167 |
| 2012/0015427 A1 | 1/2012 | Green et al. | 435/257.2 |
| 2012/0021478 A1 | 1/2012 | Osterhout et al. | 435/167 |
| 2012/0045807 A1 | 2/2012 | Simpson et al. | 435/148 |
| 2012/0055081 A1 | 3/2012 | Aravanis | |
| 2012/0164711 A1 | 6/2012 | Muir et al. | |
| 2012/0225466 A1 | 9/2012 | Burk et al. | 435/167 |
| 2012/0329119 A1 | 12/2012 | Burgard et al. | 435/167 |
| 2013/0189753 A1 | 7/2013 | Pearlman et al. | 435/167 |
| 2013/0210104 A1 | 8/2013 | Pearlman et al. | 435/167 |
| 2013/0252300 A1 | 9/2013 | Green et al. | 435/161 |
| 2013/0323820 A1 | 12/2013 | Chen et al. | 435/252.3 |
| 2013/0330709 A1 | 12/2013 | Beatty et al. | 435/4 |
| 2014/0065686 A1 | 3/2014 | Marliere | 435/167 |
| 2014/0141482 A1 | 5/2014 | Pearlman et al. | 435/167 |
| 2014/0148622 A1 | 5/2014 | Nair | |
| 2014/0186913 A1 | 7/2014 | Botes et al. | 435/167 |
| 2014/0206901 A1 | 7/2014 | Koepke et al. | 562/577 |
| 2014/0234926 A1 | 8/2014 | Beck et al. | |
| 2014/0242649 A1 | 8/2014 | Yeh et al. | 435/134 |
| 2014/0335576 A1 | 11/2014 | Chotani et al. | 435/131 |
| 2015/0037860 A1 | 2/2015 | Botes et al. | 435/167 |
| 2015/0037869 A1 | 2/2015 | Savile et al. | 435/193 |
| 2015/0079654 A1 | 3/2015 | Botes et al. | 435/167 |
| 2015/0140640 A1 | 5/2015 | Reed | |
| 2015/0191747 A1 | 7/2015 | Chen et al. | 435/131 |
| 2015/0210987 A1 | 7/2015 | Nagaraju et al. | C12N 9/0006 |
| 2015/0284742 A1 | 10/2015 | Furutani et al. | C12P 5/007 |
| 2015/0291981 A1 | 10/2015 | Marliere et al. | C12P 5/026 |
| 2016/0002672 A1 | 1/2016 | Beck et al. | C12P 5/007 |

(Continued)

FOREIGN PATENT DOCUMENTS

| | | |
|---|---|---|
| CN | 103602626 | 2/1916 |
| EP | 2336340 | 6/2011 |

(Continued)

OTHER PUBLICATIONS

Zhou et al Biosynthesis of isoprene in *Escherichia coli* via methylerythritol phosphate (MEP) pathway. Appl Microbiol Biotechnol (2011) 90:1915-1922 (Year: 2011).*

Kuzuyama, Tomohisa, "Mevalonate and Nonmevalonate Pathways for the Biosynthesis of Isoprene Units", Bioscience Biotechnology Biochemistry, vol. 66, No. 8, 2002, pp. 1619-1627.

Whited et al., "Development of a Gas-Phase Bioprocess for Isoprene-Monomer Production Using Metabolic Pathway Engineering", Peer Review, Technology Update, Industrial Biotechnology, vol. 6, No. 3, 2010, pp. 152-163.

(Continued)

*Primary Examiner* — Kagnew H Gebreyesus

(57) ABSTRACT

Systems, networks, methods, compositions and recombinant hosts for biosynthesizing hydrocarbons from a feedstock, such as gas, are provided.

31 Claims, 4 Drawing Sheets

Specification includes a Sequence Listing.

(56) References Cited

U.S. PATENT DOCUMENTS

| | | | |
|---|---|---|---|
| 2016/0017374 A1 | 1/2016 | Leonard et al. | 585/16 |
| 2016/0130618 A1 | 5/2016 | Hara et al. | |
| 2017/0051314 A1 | 2/2017 | Conradie | C12P 5/007 |
| 2017/0106054 A1 | 4/2017 | Summar et al. | A61K 38/44 |
| 2017/0145441 A1 | 5/2017 | Conradie | |
| 2018/0094282 A1 | 4/2018 | Cartman et al. | C12P 5/007 |
| 2018/0127788 A1 | 5/2018 | Kamionka et al. | C12P 5/007 |
| 2018/0291401 A1 | 10/2018 | Conradie | C12P 5/007 |
| 2019/0002926 A1 | 1/2019 | Cartman et al. | C12P 5/007 |
| 2019/0017076 A1 | 1/2019 | Conradie | C12P 5/007 |
| 2019/0093130 A1 | 3/2019 | Pearlman et al. | C12P 5/007 |
| 2019/0218577 A1 | 7/2019 | Cartman et al. | C12P 5/007 |
| 2019/0271009 A1 | 9/2019 | Conradie | C12P 5/007 |

FOREIGN PATENT DOCUMENTS

| | | |
|---|---|---|
| EP | 2336341 | 6/2011 |
| EP | 12190039 | 10/2012 |
| EP | 2913392 | 9/2015 |
| KR | 20150006097 | 1/2015 |
| WO | 2006/014837 | 2/2006 |
| WO | 2009/064910 | 5/2009 |
| WO | 2009/111513 | 9/2009 |
| WO | 2009/132220 | 10/2009 |
| WO | WO 2009/132220 | 10/2009 |
| WO | 2009/155382 | 12/2009 |
| WO | 2010/001078 | 1/2010 |
| WO | 2010/031062 | 3/2010 |
| WO | 2010/099201 | 9/2010 |
| WO | 2010/115838 A1 | 10/2010 |
| WO | 2011/011689 | 1/2011 |
| WO | 2011/076261 | 6/2011 |
| WO | 2011/076689 | 6/2011 |
| WO | 2011/076691 | 6/2011 |
| WO | 2011/079314 | 6/2011 |
| WO | 2011/140171 | 11/2011 |
| WO | 2012/018624 | 2/2012 |
| WO | 2012/052427 | 4/2012 |
| WO | 2012/174439 | 12/2012 |
| WO | 2013/007786 | 1/2013 |
| WO | 2013/020118 | 2/2013 |
| WO | 2013/028519 | 2/2013 |
| WO | 2013/036812 | 3/2013 |
| WO | 2013/040383 | 3/2013 |
| WO | 2013/057194 | 4/2013 |
| WO | 2013/082542 | 6/2013 |
| WO | 2013/090915 | 6/2013 |
| WO | 2013/092567 | 6/2013 |
| WO | 2013096863 A1 | 6/2013 |
| WO | 2013/119340 | 8/2013 |
| WO | 2013/150100 | 10/2013 |
| WO | 2013/173437 | 11/2013 |
| WO | 2013/180584 | 12/2013 |
| WO | 2013/181647 | 12/2013 |
| WO | 2013/188546 | 12/2013 |
| WO | 2013/192183 | 12/2013 |
| WO | 2014/001517 | 1/2014 |
| WO | 2014/015210 | 1/2014 |
| WO | 2014/033129 | 3/2014 |
| WO | 2014/064198 | 5/2014 |
| WO | 2014/085612 | 6/2014 |
| WO | 2014/100726 | 6/2014 |
| WO | 2014/193473 | 12/2014 |
| WO | WO 2014/193473 | 12/2014 |
| WO | 2017/029549 | 2/2017 |
| WO | 2017/029553 | 2/2017 |
| WO | 2018/064105 | 4/2018 |
| WO | 2019/006255 | 1/2019 |
| WO | 2019/006257 | 1/2019 |

OTHER PUBLICATIONS

Makkar, et al., "*Cupriavidus necator* gen. nov., sp. nov.: a Nonobligate Bacterial Predator of Bacteria in Soil", International Journal of Sysytematic Bacteriology, vol. 37, No. 4, Oct. 1987, p. 323-326.

Byrd, et al., "Bacterial control of Agromyces ramosus in soil", Can. J. Microbiol., vol. 31, 1985, p. 1157-1163.

Sillman, et al., "Isolation of nonobligate bacterial predators of bacteria from soil", Can. J. Microbiol., vol. 32, 1986, p. 760-762.

Zeph, et al., "Gram-negative versus gram-positive (actinomycete) bacterial predators of bacteria in soil", Appl. Environ. Microbiol., vol. 522, 1986, p. 319-823.

Akatsuka et al. "The Serratia marcescens bioH gene encodes an esterase" Gene 2003 302:185-192.

Barta et al. "Structural basis for nucleotide binding and reaction catalysis in mevalonate diphosphate decarboxylase" Biochemistry 2012 51(28):5611-5621.

Becker et al. "Metabolic flux engineering of L-lysine production in Corynebacterium glutamicum—over expression and modification of G6P dehydrogenase" Journal of Biotechnology 2007 132:99-109.

Bischoff, K.M & Rodwell, V.W. "Biosynthesis and characterization of (S)-and (R)-3-hydroxy-3-methylglutaryl coenzyme A" Biochem Med Metab Biol 1992 48(2):149-58.

Boucher et al. "Bacterial origin for the isoprenoid biosynthesis enzyme HMG-CoA reductase of the archaeal orders Thermoplasmatales and Archaeoglobales" Mol. Biol. Evol. 2011 18(7):1378-1388.

Brigham et al. Advanced Biofuels and Bioproducts, Springer New York, Chapter 39 2013 pp. 1065-1090.

Brodkorb et al. "Linalool dehydratase-isomerase, a bifunctional enzyme in the anaerobic degradation of monoterpenes" J Biol Chem 285(40):30436-30442.

Buckel et al. "Glutaconate CoA-transferase from Acidaminococcus fermentans" Eur J Biochem 1981 118(2):315-321.

Buckel et al. "2-Hydroxyl-CoA Dehydratases, a novel family of moybdeum enzymes" J Inorganic Biochemistry 2003 96(1):53.

Bugg et al. "The emerging role for bacteria in lignin degradation and bio-product formation" Current Opinion in Biotechnology 2011 22:394-400.

Chayabutra & Ju "Degradation of n-hexadecane and its metabolites by Pseudomonas aeruginosa under microaerobic and anaerobic denitrifying conditions" Appl Environ Microbiol 2000 66(2):493-498.

Chica et al. "Semi-rational approaches to engineering enzyme activity: combining the benefits of directed evolution and rational design" Current Opinion in Biotechnology 2005 16:378-384.

Chung & Rhee "Overexpression of the (R)-specific enoyl-CoA hydratase gene from Pseudomonas chlororaphis HS21 in Pseudomonas strains for the biosynthesis of polyhydroxyalkanoates of altered monomer composition" Biosci Biotechnol Biochem 2012 76(3):613-616.

Daniel et al. "Biochemistry of coenzyme B12-dependent glycerol and diol dehydratases and organization of the encoding genes" FEMS Microbiology Reviews 1999 22:553-566.

Devos & Valencia "Practical Limits of Function Prediction" Proteins: Structure, Function and Genetics 2000 41:98-107.

Demain et al. "Manual of Industrial Microbiology and Biotechnology", 2nd Edition, Scale-Up of Microbial Process, ASM Press, 1999, 5 pages.

Dhe-Paganon et al. "Mechanism of mevalonate pyrophosphate decarboxylase: evidence for a carbocationic transition state" Biochemistry 1994 33(45):13355-1336.

Eikmanns & Buckel "Crystalline green 5-hydroxyvaleryl-CoA dehydratase from Clostridium aminovalericum" Eur J Biochem 1991 197(3):661-668.

Eriksen et al. "Protein design for pathway engineering" Journal of Structural Biology 2013 185(2):234-242.

Ferrandez et al. "Genetic characterization and expression in heterologous hosts of the 3-(3-hydroxyphenyl)propionate catabolic pathway of *Escherichia coli* K-12" J Bacteriol 1997 179(8):2573-2581.

Forster-Fromme et al. "Biochemical characterization of isovaleryl-CoA dehydrogenase (LiuA) of Pseudomonas aeruginosa and the importance of liu genes fora functional catabolic pathway of methyl-branched compounds" FEMS Microbiol Lett 2008 286(1):78-8.

Fukui et al. "Expression and characterization of (R)-specific enoyl coenzyme A hydratase involved in polyhydroxyalkanoate biosynthesis by Aeromonas caviae" J Bacteriology 1998 180(3):667-673.

(56) References Cited

OTHER PUBLICATIONS

Gehret et al. "Terminal alkene formation by the thioesterase of curacin A biosynthesis: structure of a decarboxylating thioesterase" J Biol Chem 2011 186(16):14445-14454.
Genbank Accession No. AAD44196.1, Oct. 15, 1999 1 page.
Genbank Accession No. AAG02436.1, Aug. 29, 2000, 1 page.
Genbank Accession No. AAG05403.1, Jan. 31, 2014 2 pages.
Genbank Accession No. AAK99143.1, Jan. 30, 2014, 2 pages.
Genbank Accession No. AAV40818.1, Feb. 4, 2005, 1 page.
Genbank Accession No. AAV40819.1, Feb. 4, 2005, 1 page.
Genbank Accession No. AAV40820.1, Feb. 4, 2005, 1 page.
Genbank Accession No. ABX19602.1, Dec. 11, 2013, 2 pages.
Genbank Accession No. BAA21816.1, Aug. 19, 1997, 2 pages.
Genbank Accession No. BAA92740.1, Aug. 1, 2007, 2 pages.
Genbank Accession No. BAB56752.1, Oct. 7, 2016, 2 pages.
Genbank Accession No. BAB56754.1, Oct. 7, 2016, 1 page.
Genbank Accession No. BAB58707.1, Oct. 7, 2016, 2 pages.
Genbank Accession No. BAD98243.1, May 10, 2005, 2 pages.
Genbank Accession No. CAA32465.1, Jul. 26, 1995, 1 page.
Genbank Accession No. CAA32466.1, Jul. 26, 1995, 1 page.
Genbank Accession No. CAA42196.1, Oct. 16, 1995, 1 page.
Genbank Accession No. CAA99573.1, Nov. 14, 2006, 2 pages.
UniProtKB/Swiss-Prot. E1XUJ2.1, Sep. 5, 2012, 2 pages.
NCBI Reference Sequence NP 746661, Jun. 27, 2013, 2 pages.
Gogerty & Bobik "Formation of isobutene from 3-hydroxy-3-methylbutyrate by diphosphomevalonate decarboxylase" Appl Environ Microbiol 2010 76(24):8004-8010.
Gu et al. "Polyketide decarboxylative chain termination preceded by o-sulfonation in curacin a biosynthesis" Am J Chem Soc 2009 131(44):16033-1603.
Guan et al. "Cytochrome P450-dependent desaturation of lauric acid: isoform selectivity and mechanism of formation of 11-dodecenoic acid" Chem Biol Interact 1998 110(1-2):103-12.
Gupta et al. "Phylogenomics and signature proteins for the alpha Protobacteria and its main groups" BMC Microbiol. 2007 7:106:1-2.
He & Spain "A novel 2-aminomuconate deaminase in the nitrobenzene degradation pathway of Pseudomonas pseudoalcaligenes JS45" J Bacteriol 1998 180(9):2502-2506.
Hermann, T. "Industrial production of amino acids by coryneform bacteria" Journal of Biotechnology 2003 104:155-172.
Ishizaki et al. "Microbial production of poly-D-3-hydroxybutyrate from CO2" Appl Microbiol Biotechnol 2001 57(1-2):6-12.
Jang et al. "Bio-based production of C2-C6 platform chemicals" Biotechnol Bioeng 2012 109(10)::2437-2459.
Jaremko et al. "The initial metabolic conversion of levulinic acid in Cupriavidus necator" Journal of Biotechnology 2011 155:293-298.
Jin et al. "The selective addition of water to C=C bonds; enzymes are the best chemists" Chem Commun. 2011 47:2502-2510.
Kasai et al. "Uncovering the protocatechuate 2,3-cleavage pathway genes" J Bacteriol 2009 191(21):6758-6768.
Kelada et al. "Delta-aminolevulinic acid dehydratase genotype and lead toxicity: a HuGE review" Am. J. Epidemiology 2001 154(1):1-1.
Kim et al. "An allylic ketyl radical intermediate in clostridial amino-acid fermentation" Nature 2008 452(7184):239-24.
Kim et al. :Dehydration of (R)-2-hydroxyacyl-CoA to enoyl-CoA in the fermentation of α-amino acids by anaerobic bacteria FEMS Microbiol Rev 2004 28(4):445-468.
Kim, "On the enzymatic mechanism of 2-hydroxyisocaproyl-CoA dehydratase from Clostridium difficile" 2004 Ph.D. dissertation, Phillipps-Universitat, Marburg, 200.
Kisselev "Polypeptide release factors in prokaryotes and eukaryotes: same function, different structure" Structure 2002 10:8-9.
Kizer et al. "Application of functional genomics to pathway optimization for increased isoprenoid production" Applied and Environmental Microbiology 2008 74(10):3229-3241.
Kneen et al. "Characterization of a thiamin diphosphate-dependent phenylpyruvate decarboxylase from Saccharomyces cerevisiae" FEBS J. 2011 278:1842-1853.
Kopke et al. "2,3-butanediol production by acetogenic bacteria, an alternative route to chemical synthesis, using industrial waste gas" Applied and Environmental Microbiology 2011 77(15):5467-5475.
Kuzma et al. "Bacteria produce the volatile hydrocarbon isoprene" Curr Microbiol 1995 30(2):97-103.
Lan et al. "ATP drives direct photosynthetic production of 1-butanol in cyanobacteria" PNAS 2012 109(16):6018-6023.
Lee et al. "Conversion of β-Methylbutyrinc Acid to β-Hydroxy-β-Methylbutyrin Acid by Galactomyces reessii" Applied and Environmental Microbiology 1997 63(11):4191-4195.
Lee et al. "Synthesis of pure meso-2,3-butanediol from crude glycerol using an engineered metabolic pathway in Escherichia coli" Applied Biochemistry and Biotechnology 2012 166(7):1801-1813.
Li et al. "Cupriavidus necator JMP134 rapidly reduces furfural with a Zn-dependent alcohol dehydrogenase" Biodegradation 2011 22(6):1215-122.
Lim et al. "Amplification of the NADPH-related genes zwf and gnd for the oddball biosynthesis of PHB in an E. coli transformant harboring a cloned phbCAB operon" Journal of Bioscience and Bioengineering 2002 93(6):543-54.
Lin et al. "The BioC O-methyltransferase catalyzes methyl esterification of malonyl-acyl carrier protein, an essential step in biotin synthesis" Journal of Biological Chemistry 2012 287(440::37010-37020.
Lin et al. "Biotin synthesis begins by hijacking the fatty acid synthetic pathway" Nature Chem Biol 2010 6:682-68.
Liu et al. "Microbial production of R-3-hydroxybutyric acid by recombinant E. coli harboring genes of phbA, phbB, and tesB" Appl Microbiol Biotechnol 2007 76(4):811-181.
Liu et al. "Zirconia microbial hollow fibre bioreactor for Esherichia coli culture" Ceramics International 2010 36:2087-2093.
Lo, H. & Chen, Y.J. "Gene cloning and biochemical characterization of a NAD(P)+-dependent aldehyde dehydrogenase from Bacillus licheniformis" Mol. Biotechnol 2010 46(2):157-67.
Luddeke et al. "Geraniol and geranial dehydrogenases induced in anaerobic monoterpene degradation by Castellaniella defragrans" Appl and Environmental Microbiology 2012 78(7):2128-2136.
Luddeke et al. "Enantiospecific (S)-(+)-linalool formation from beta-myrcene by linalool dehydratase-isomerase" Z. Naturforsch C 2011 66(708):409-412.
Luo et al. "Production of 3-hydroxypropionic acid through propionaldehyde dehydrogenase PduP mediated biosynthetic pathway in Klebsiella pneumonia" Bioresour Technol 2011 103(1):1-6.
Martin et al. "High-titer production of monomeric hydroxyvalerates from levulinic acid in Pseudomonas putida" Journal of Biotechnology 2009 139(1):61-67.
Martin et al. "Engineering a mevalonate pathway in Escherichia coli for production of terpenoids" Nature Biotechnology 2003 21:796-802.
McCarthy et al. "Structural basis of functional group activation by sulfotransferases in complex metabolic pathways" ACS Chem Biol 2012 7:1994-2003.
Meijnen et al. "Improved p-hydroxybenzoate production by engineered Pseudomonas putida S12 by using a mixed-substrate feeding strategy" Applied Microbiology and Biotechnology 2011 90(3):885-893.
Mo et al. "Biosynthesis of the Allylmalonyl-CoA Extended Unit for the FK506 Polyketide Synthase (PKS) Proceeds Through a Dedicated PKS and Faciliates the Mutasynthesis of Novel Analogs" J Am Chem Soc 2010 1333(4):976-985.
Morrone et al. "Increasing diterpene yield with a modular metabolic engineering system in E. coli: comparison of MEV and MEP isoprenoid precursor pathway engineering" Applied Microbiology and Biotechnology 2010 85:1893-1906.
Muraki et al. "Prokaryotic homologs of the eukaryotic 3-hydroxyanthranilate 3,4-dioxygenase and 2-amino-3-carboxymuconate-6-semialdehyde decarboxylase in the 2-nitrobenzoate degradation pathway of Pseudomonas fluorescens strain KU-7" Appl Environ Microbiol 2003 69(3):1564-1572.

(56) References Cited

OTHER PUBLICATIONS

Ohashi et al. "Continuous production of lactic acid from molasses by perfusion culture of Lactococcus lactis using a stirred ceramic membrane reactor" Journal of Bioscience and Bioengineering 1999 87(5): 647-654.
Papanikolaou et al. "Citric acid production by Yarrowia lipolytica cultivated on olive-mill wastewater-based media" Bioresource Technology 2008 99(7):2419-2428.
Perez-Pantoja et al. "Metabolic reconstruction of aromatic compounds degradation from the genome of the amazing pollutant-degrading bacterium *Cupriavidus necator* JMP134" FEMS Microbiology Reviews 2008 32:736-794.
Pitera et al. "Balancing a heterologous mevalonate pathway for improved isoprenoid production in *Escherichia coli*" Metabolic Engineering 2007 9:193-207.
Prather et al. "De novo biosynthetic pathways: rational design of microbial chemical factories" Curr Opin Biotechnol 2008 19:468-474.
"Production of Butadiene" China Synthetic Rubber Industry, Special Issue of 1978, 21 pages (with partial English translation).
Przybylski et al. "Third-generation feed stocks for the clean and sustainable biotechnological production of bulk chemicals: Synthesis of 2-hydroxyisobutyric acid" Energy, Sustainability and Society 2012 2(11):1-9.
Ramsay et al. "Use of a nylon manufacturing waste as an industrial fermentation substrate" Applied and Environmental Microbiology 1986 52(1):152-156.
Rettie et al. "CYP4 isozyme specificity and the relationship between omega-hydroxylation and terminal desaturation of valproic acid" Biochemistry 1995 34(24):7889-7895.
Rodruguez-Zavala et al. "Characterization of *E. coli* tetrameric aldehyde dehydrogenases with atypical properties compared to other aldehyde dehydrogenases" Protein Science 2006 15:1387-1396.
Rude et al. "Terminal olefin (1-alkene) biosynthesis by a novel p450 fatty acid decarboxylase from *Jeotgalicoccus* species" Appl Environ Microbiol 2011 77(5):1718-1727.
Schafer et al. "Synthesis of short-chain diols and unsaturated alcohols from secondary alcohol substrates by the Rieske nonheme mononuclear iron oxygenase MdpJ" Appl Environ Microbiol 2012 78(17):6280-6284.
Scherf & Buckel "Purification and properties of an iron-sulfur and FAD-containing 4-hydroxybutyryl-CoA dehydratase/vinylacetyl-CoA delta 3-delta 2-isomerase from Clostridium aminobutyricum" Eur J Biochem 1993 215(2):421-429.
Scherf et al. "Succinate-ethanol fermentation in Clostridium kluyveri: purification and characterisation of 4-hydroxybutyryl-CoA dehydratase/vinylacetyl-CoA delta 3-delta 2-isomerase" Arch Microbiol 1994 161(3):239-245.
Seedorf et al. "The genome of Clostridium kluyveri, a strict anaerobe with unique metabolic features" PNAS USA 2008 105:2128-2133.
Sen et al. "Developments in directed evolution for improving enzyme functions" Appl Biochem Biotechnol 2007 143:212-223.
Shen et al. "Driving forces enable high-titer anaerobic 1-butanol synthesis in *Escherichia coli*" Appl Environ Microbiol 2011 77(9):2905-2915.
Silver & Fall "Characterization of aspen isoprene synthase, an enzyme responsible for leaf isoprene emission to the atmosphere" J Biol Chem 1995 270(22):13010-13016.
Slater et al. "Multiple beta-ketothiolases mediate poly(beta-hydroxyalkanoate) copolymer synthesis in Ralstonia eutropha" J. Bacter. 1998 180(8):1979-1987.
Studier "Protein production by auto-induction in high density shaling cultures" Protein Expression and Purification 2005 41:207-234.
Sweeney et al. "Physiologically based pharmacokinetic modeling of 1,3-butadiene, 1,2-epoxy-3-butene, and 1,2:3,4-diepoxybutane toxicokinetics in mice and rats" Carcinogenesis 1997 18(4):611-625.

Toraya et al. "Radical catalysis of B12 enzymes: structure, mechanism, inactivation, and reactivation of diol and glycerol dehydratases" Cellular and Molecular Life Sciences 2000 57:106-127.
Tseng et al. "Biosynthesis of chiral 3-hydroxyvalerate from single propionate-unrelated carbon sources in metabolically engineered *E. coli*" Microb Cell Fact 2010 9:96.
Tsuge et al. "Molecular characterization and properties of (R)-specific enoyl-CoA hydratases from Pseudomonas aeruginosa: metabolic tools for synthesis of polyhydroxyalkanoates via fatty acid beta-oxidation" Int J. Biol Macromol 2003 31(4-5):195-205.
Ulmer et al. "Bacterial Production of Poly($\beta$-hydroxyalkanoates) Contaning Unsaturated Repeating Units by Rhodospirillum rubrum" Macromolecules 1994 27(7):1675-1679.
Uniprot Accession No. 032472, Jun. 11, 2014, 2 pages.
Uniprot Accession No. B8ZLF3, Jun. 15, 2010, 2 pages.
Uniprot Accession No. I3RA72, Sep. 5, 2012, 2 pages.
Uniprot Accession No. P0A6RO, May 14, 2014, 5 pages.
Uniprot Accession No. P0A8Z0, Jun. 11, 2014, 3 pages.
Uniprot Accession No. P0AGG2, Jun. 11, 2014, 3 pages.
Uniprot Accession No. P0AEK4, Jun. 11, 2014, 6 pages.
Uniprot Accession No. P0A6Q6, Jun. 11, 2014, 3 pages.
Uniprot Accession No. P0A953, Jun. 11, 2014, 4 pages.
Uniprot Accession No. P0AEK2, May 14, 2014, 4 pages.
Uniprot Accession No. P13001, Jun. 11, 2014, 4 pages.
Uniprot Accession No. P32377, Jun. 15, 2010, 4 pages.
Uniprot Accession No. Q5EU90, Feb. 19, 2014, 2 pages.
Uniprot Accession No. Q73A47, May 14, 2014, 2 pages.
Uniprot Accession No. Q7CCL9, Jun. 15, 2010, 2 pages.
Uniprot Accession No. Q818X2, Jun. 11, 2014, 2 pages.
Upton & McKinney "Role of the methylcitrate cycle in propionate metabolism and detoxification in *Mycobacterium smegmatis*" Microbiology 2007 153(Pt 12):3973-3982.
Van Leeuwen et al. "Fermentative production of isobutene" Appl Microbiol Biotechnol 2012 93(4):1377-1387.
Wang & Liao "Alteration of product specificity of Rhodobacter sphaeroides phytoene desaturase by directed evolution" J Biol Chem 2001 276(44):41161-41164.
Wee et al. "Biotechnological Production of Lactic Acid and Its Recent Applications" Food Technology and Biotechnology 2006 44(2):163-172.
Wendt et al. "Crystal structure of the carboxyltransferase subunit of the bacterial sodium ion pump glutaconyl-coenzyme A decarboxylase" EMBO J 2003 22(14):3493-3502.
Westin et al. "The identification of a succinyl-CoA thioesterase suggests a novel pathway for succinate production in peroxisomes" J Biol Chem 2005 280:38125-38132.
Whisstock et al. "Prediction of protein function from protein sequence and structure" Quarterly Reviews of BioPhysics 2003 36(3):307-340.
White "Butadiene production process overview" Chem Biol Interact 2007 166(1-3):10-14.
Witkowski et al. "Conversion of a beta-ketoacyl synthase to a malonyl decarboxylase by replacement of the active-site cysteine with glutamine" Biochemistry 1999 38:11643-1165.
Yang et al. Enhancing Production of Bio-Isoprene Using Hybrid MVA Pathway and Isoprene Synthase in *E. coli*: PLoS One 2012 7:1-7.
Yang et al. "Value-added uses for crude glycerol—a byproduct of biodiesel production" Biotechnology for Biofuels 2012 5(10):1-10.
Zhang et al. "Genes encoding acyl-CoA dehydrogenase (AcdH) homologues from Streptomyces coelicolor and Streptomyces avermitilis provide insights into the metabolism of small branched-chain fatty acids and macrolide antibiotic production" Microbiology 1999 145(9):2323-2334.
Zhao et al. "Biosynthesis of isoprene in *Escherichia coli* via methylerythritol phosphate (MEP) pathway" Applied Microbiology and Biotechnology 2011 90:1915-1922.
Zhou et al. "Isopentenyl diphosphate and dimethylallyl diphosphate/isopentenyl diphosphate ratio measured with recombinant isopentenyl diphosphate isomerase and isoprene synthase" Analytical Biochemistry 2013 440:130-136.

(56) References Cited

OTHER PUBLICATIONS

Zhuang et al. "Structure of YciA from Haemophilus influenzae (HI0827), a hexameric broad specificity acyl-coenzyme A thioesterase" Biochemistry 2008 47(9):2789-2796.
Chinese Office Action in Chinese Application No. 201280040122.2 dated Jul. 17, 2015.
Office Communication in CN201280068870.1 dated Aug. 23, 2016.
Office Communication in CN201280040122.2 dated Jun. 8, 2016.
Office Communication in CN201380043586.3 dated Nov. 8, 2016.
European Communication pursuant to Rules 161(1) and 162 EPC in application No. EP 12799032.3 dated Jun. 25, 2014.
Office Communication in EP 12799032.3 dated Dec. 10, 2015.
Office Communication in EP 12799032.3 dated Mar. 3, 2016.
Office Communication in EP 12799032.3 dated Jun. 16, 2016.
Office Communication in EP12731825.1 dated Nov. 17, 2015.
Office Communication in EP12731825.1 dated Feb. 4, 2019.
Office Communication in EP 13812263.5 dated Jan. 12, 2017.
Office Communication in EP 13812263.5 dated Sep. 26, 2018.
Office Communication in U.S. Appl. No. 13/524,973 dated Jun. 11, 2014.
Office Communication in U.S. Appl. No. 13/524,973 dated Dec. 22, 2014.
Office Communication in U.S. Appl. No. 13/524,973 dated Jul. 23, 2015.
Office Communication in U.S. Appl. No. 13/524,973 dated Apr. 20, 2016.
Office Communication in U.S. Appl. No. 13/524,973 dated Aug. 30, 2016.
Office Communication in U.S. Appl. No. 13/524,973 dated Jan. 26, 2017.
Office Communication in U.S. Appl. No. 13/691,623 dated Mar. 4, 2014.
Office Communication in U.S. Appl. No. 13/691,623 dated Jun. 25, 2014.
Office Communication in U.S. Appl. No. 13/691,623 dated Dec. 9, 2014.
Office Communication in U.S. Appl. No. 13/691,623 dated Mar. 16, 2015.
Office Communication in U.S. Appl. No. 13/691,623 dated Apr. 23, 2015.
Office Communication in U.S. Appl. No. 13/691,623 dated Jul. 17, 2015.
Office Communication in U.S. Appl. No. 13/691,623 dated Dec. 7, 2015.
Office Communication in U.S. Appl. No. 13/691,623 dated May 4, 2016.
Office Communication in U.S. Appl. No. 13/916,156 dated Jan. 9, 2015.
Office Communication in U.S. Appl. No. 13/916,156 dated Jul. 14, 2015.
Office Communication in U.S. Appl. No. 13/916,156 dated Dec. 3, 2015.
Office Communication in U.S. Appl. No. 13/916,156 dated Mar. 15, 2016.
Office Communication in U.S. Appl. No. 13/916,156 dated Apr. 7, 2016.
Office Communication in U.S. Appl. No. 13/916,156 dated Apr. 20, 2016.
Office Communication in U.S. Appl. No. 13/916,156 dated May 17, 2016.
Office Communication in U.S. Appl. No. 14/092,115 dated Apr. 1, 2015.
Office Communication in U.S. Appl. No. 14/092,115 dated Oct. 27, 2015.
Office Communication in U.S. Appl. No. 14/092,115 dated Feb. 2, 2016.
Office Communication in U.S. Appl. No. 14/092,115 dated Mar. 21, 2016.
Office Communication in U.S. Appl. No. 14/092,115 dated Jul. 12, 2016.
Office Communication in U.S. Appl. No. 14/092,115 dated Oct. 12, 2016.
Office Communication in U.S. Appl. No. 14/092,115 dated Apr. 6, 2017.
Office Communication in U.S. Appl. No. 14/092,115 dated Jul. 27, 2017.
Office Communication in U.S. Appl. No. 14/334,190 dated Feb. 5, 2016.
Office Communication in U.S. Appl. No. 14/334,190 dated Jul. 27, 2016.
Office Communication in U.S. Appl. No. 14/334,190 dated Jan. 20, 2017.
Office Communication in U.S. Appl. No. 14/334,190 dated May 9, 2017.
Office Communication in U.S. Appl. No. 14/334,190 dated Oct. 5, 2017.
Office Communication in U.S. Appl. No. 14/334,190 dated Mar. 13, 2018.
Office Communication in U.S. Appl. No. 14/334,190 dated Apr. 25, 2018.
Office Communication in U.S. Appl. No. 14/334,190 dated Jul. 30, 2018.
Office Communication in U.S. Appl. No. 14/334,190 dated Sep. 10, 2018.
Office Communication in U.S. Appl. No. 14/334,190 dated Sep. 28, 2018.
Office Communication in U.S. Appl. No. 14/334,190 dated Nov. 16, 2018.
Office Communication in U.S. Appl. No. 14/334,190 dated Jan. 9, 2019.
Office Communication in U.S. Appl. No. 14/452,201 dated May 20, 2016.
Office Communication in U.S. Appl. No. 14/452,201 dated Oct. 28, 2016.
Office Communication in U.S. Appl. No. 14/452,201 dated Apr. 5, 2017.
Office Communication in U.S. Appl. No. 14/452,201 dated Aug. 30, 2017.
Office Communication in U.S. Appl. No. 14/914,741 dated Nov. 17, 2016.
Office Communication in U.S. Appl. No. 14/914,741 dated Feb. 7, 2017.
Office Communication in U.S. Appl. No. 14/914,741 dated Aug. 17, 2017.
Office Communication in U.S. Appl. No. 14/914,741 dated Jul. 24, 2018.
Office Communication in U.S. Appl. No. 14/914,741 dated Apr. 19, 2019.
Office Communication in U.S. Appl. No. 14/914,741 dated Sep. 16, 2019.
Office Communication in U.S. Appl. No. 15/238,225 dated Dec. 18, 2018.
Office Communication in U.S. Appl. No. 15/238,225 dated Mar. 11, 2019.
Office Communication in U.S. Appl. No. 15/238,225 dated Oct. 10, 2019.
Office Communication in U.S. Appl. No. 15/238,225 dated Feb. 27, 2020.
Office Communication in U.S. Appl. No. 15/238,234 dated Nov. 30, 2017.
Office Communication in U.S. Appl. No. 15/238,234 dated May 2, 2018.
Office Communication in U.S. Appl. No. 15/238,234 dated Aug. 13, 2018.
Office Communication in U.S. Appl. No. 15/238,234 dated Nov. 16, 2018.
Office Communication in U.S. Appl. No. 15/717,065 dated Nov. 8, 2018.
Office Communication in U.S. Appl. No. 15/717,065 dated Feb. 13, 2019.
Office Communication in U.S. Appl. No. 15/717,065 dated Jun. 19, 2019.

(56) References Cited

OTHER PUBLICATIONS

Office Communication in U.S. Appl. No. 15/717,065 dated Oct. 1, 2019.
Office Communication in U.S. Appl. No. 15/808,409 dated May 8, 2019.
Office Communication in U.S. Appl. No. 15/808,409 dated Sep. 5, 2019.
Office Communication in U.S. Appl. No. 15/932,217 dated Jun. 10, 2019.
Office Communication in U.S. Appl. No. 15/932,217 dated Sep. 13, 2019.
Office Communication in U.S. Appl. No. 15/932,189 dated Dec. 5, 2019.
Office Communication in U.S. Appl. No. 16/188,673 dated Dec. 10, 2019.
Office Communication in U.S. Appl. No. 16/022,878 dated Feb. 12, 2019.
Office Communication in U.S. Appl. No. 16/022,878 dated Aug. 28, 2019.
Office Communication in U.S. Appl. No. 16/022,878 dated Apr. 16, 2020.
International Search Report in PCT/US2012/042757 dated Mar. 6, 2013.
International Preliminary Report on Patentability in PCT/US2012/042757 dated Dec. 17, 2013.
International Search Report in PCT/US2012/064407 dated Feb. 7, 2013.
International Preliminary Report on Patentability in PCT/US2012/064407 dated May 13, 2014.
International Search Report in PCT/US2012/067463 dated Jun. 17, 2013.
International Preliminary Report on Patentability in PCT/US2012/067463 dated Jun. 3, 2014.
International Search Report and Written Opinion in PCT/US2013/045430 dated Feb. 3, 2014.
International Preliminary Report on Patentability in PCT/US2013/045430 dated Dec. 16, 2014.
International Search Report and Written Opinion in PCT/US2013/072275 dated Mar. 6, 2014.
International Preliminary Report on Patentability in PCT/US2013/072275 dated Jun. 2, 2015.
International Search Report and Written Opinion in PCT/US2014/048606 dated Oct. 31, 2014.
International Preliminary Report on Patentability in PCT/US2014/048606 dated Feb. 2, 2016.
International Search Report and Written Opinion in PCT/US2014/049786 dated Sep. 11, 2015.
International Preliminary Report on Patentability in PCT/US2014/049786 dated Feb. 9, 2016.
International Search Report and Written Opinion in PCT/US2014/049807 dated Nov. 5, 2014.
International Preliminary Report on Patentability in PCT/US2014/049807 dated Feb. 9, 2016.
International Search Report and Written Opinion in PCT/IB2016/001233 dated Feb. 28, 2017.
International Report on Patentability in PCT/IB2016/001233 dated Feb. 20, 2018.
International Search Report and Written Opinion in PCT/IB2016/001245 dated Feb. 27, 2017.
International Report on Patentability in PCT/IB2016/001245 dated Feb. 20, 2018.
International Search Report and Written Opinion in PCT/US2017/053607 dated Dec. 22, 2017.
International Report on Patentability in PCT/ US2017/053607 dated Apr. 2, 2019.
International Search Report and Written Opinion in PCT/US2018/040213 dated Sep. 21, 2018.
International Report on Patentability in PCT/US2018/040213 dated Dec. 31, 2019.
International Report on Patentability in PCT/US2018/040218 dated Dec. 31, 2019.
Office Communication in U.S. Appl. No. 16/144,035 dated Mar. 9, 2020.
Kuzuyuma & Seto "Two distinct pathways for essential metabolic precursors for isoprenoid biosynthesis" Proc Jap Acad. Ser B 88 2012 3:41-52.
Islam et al. "Investigating Moorella thermoacetica Metabolism with a Genome-Scale Constraint0based Metabolic Model" Integrative Biology 2015 26 pages.
Marcellin et al. "Low Carbon Fuels and Commodity Chemicals from Waste Gases—Systematic Approach to Understand Energy Metabolism in a Model Acetogen" Green Chemistry Royal Society of Chemistry, 2016 10 pages.
Nagarajan et al. "Characterizing Acetogenic Metabolism Using a Genome-Scale Metabolic Reconstruction of Clostridium ljungdahili" Microbial Cell Factories 2013 pp. 1-13.
Pereira et al. "Improving the Flux Distributions Simulated with Genome-Scale Metabolic Models of Saccaromy cescerevisiae" Metabolic Engineering Communications 3 2016 153-163.
Valgepea et al. "Maintenance of ATP Homeostasis Triggers Metabolic Shifts in Gas-Fermenting Acetogens" Cell Systems 2017 4:505-515.
Office Communication in U.S. Appl. No. 16/144,035 dated Aug. 10, 2020.
Tan et al. "Activating Phosphenolpyruvate Carboxylase and Phosphoenolpyruvate Carboxykinase in Combination for Improvement of Succinate Production" Applied and Environmental Microbiolgy 2013 79(16):4838-4844.
Office Communication in U.S. Appl. No. 16/144,035 dated Dec. 24, 2020.
Office Communication in U.S. Appl. No. 16/022,878 dated Sep. 30, 2020.
International Search Report and Written Opinion in PCT/US2018/040218 dated Oct. 3, 2018.
Non Final Office Action received for U.S. Appl. No. 15/238,225, dated Dec. 14, 2020, 17 Pages.
Non Final Rejection received for U.S. Appl. No. 16/022,878, dated Jul. 28, 2021, 17 Pages.

\* cited by examiner

METHODS, SYNTHETIC HOSTS AND REAGENTS FOR THE BIOSYNTHESIS OF HYDROCARBONS

This patent application claims the benefit of priority from U.S. Provisional Patent Application Ser. No. 62/527,551 filed Jun. 30, 2017, teachings of which are herein incorporated by reference in their entirety.

FIELD

The present invention relates to biological systems, recombinant host cells, polynucleotides and polypeptides, methods for their production, and methods for their use in the production of hydrocarbons.

BACKGROUND

Hydrocarbons are important monomers for the production of specialty elastomers useful in making a variety of products, including motor mounts/fittings, surgical gloves, rubber bands, golf balls and shoes. For example, styrene-isoprene-styrene block copolymers form a key component of hot-melt pressure-sensitive adhesive formulations and cis-poly-isoprene is utilized in the manufacture of tires (Whited et al. Industrial Biotechnology 2010 6(3):152-163). Manufacturers of rubber goods depend on either imported natural rubber from the Brazilian rubber tree or petroleum-based synthetic rubber polymers (Whited et al. 2010, supra).

Given an over-reliance on petrochemical feedstocks, biotechnology offers an alternative approach to the generation of industrially relevant products, via biocatalysis.

Construction of recombinant microorganisms and methods of their use to produce isoprene is known in the art. However, many of these methods and processes are unsatisfactory because they rely on agricultural commodities such as sugar cane and corn which can be volatile in supply and cost from time to time. The use of sugar derived from agricultural waste, often called 'biomass' has been proposed. However, these processes are still nascent, and assured supply and cost is not possible.

There are known metabolic pathways leading to the synthesis of isoprene in eukaryotes such as *Populus alba* and some prokaryotes such as *Bacillus subtilis* have been reported to emit isoprene (Whited et al. 2010, supra). Isoprene production in prokaryotes is however rare, and no prokaryotic isoprene synthase (hereafter ISPS) has been described to date.

Generally, two metabolic routes have been described incorporating the molecule dimethylallyl-pyrophosphate, the precursor to isoprene. These are known as the mevalonate and the non-mevalonate pathways (Kuzuyama Biosci. Biotechnol. Biochem. 2002 66(8):1619-1627), both of which function in terpenoid synthesis in vivo. Both require the introduction of a non-native ISPS in order to divert carbon to isoprene production.

The mevalonate pathway generally occurs in higher eukaryotes and Archaea and incorporates a decarboxylase enzyme, mevalonate diphosphate decarboxylase (hereafter MDD), that introduces the first vinyl-group into the precursors leading to isoprene. The second vinyl-group is introduced by isoprene synthase in the final step in synthesizing isoprene. The non-mevalonate pathway or 2-C-methyl-D-erythritol 4-phosphate (MEP) pathway occurs in many bacteria and dimethylallyl-PP is generated alongside isopentenyl-PP, two molecules which are interconvertible via the action of isopentenyl pyrophosphate isomerase or isopentyl diphosphate isomerase (hereafter IDI).

SUMMARY

Biotechnology offers more sustainable methods for producing industrial intermediates, in particular pentahydrocarbons such as isoprene. Disclosed herein are methods, compositions and hosts for synthesizing hydrocarbons and derivatives thereof.

In one nonlimiting embodiment, the methods, compositions and hosts are used to synthesize hydrocarbons comprising one or more isoprene units as depicted in Formula I

as well as salts or derivatives thereof.

An aspect of the present invention thus relates to a method for biosynthesizing hydrocarbons in a recombinant host. In one nonlimiting embodiment, the invention relates to a method of synthesis of a hydrocarbon comprising one or more isoprene units as depicted in Formula I

or a salt or derivative thereof. This method comprises providing a gaseous stream to a fermentation reactor or reactors. This method further comprises providing a recombinant host to the fermentation reactor. In one nonlimiting embodiment, the recombinant host comprises an exogenous nucleic acid sequence encoding a polypeptide having an activity of EC 2.2.1.7. In one nonlimiting embodiment, the recombinant host comprises exogenous nucleic acid sequences encoding a polypeptide having an activity of EC 2.2.1.7 and a polypeptide having an activity of EC 4.2.3.27. In one nonlimiting embodiment, an activity of EC 2.2.1.7 is 1-deoxy-D-xylulose-5-phosphate synthase (DXS) activity. In one nonlimiting embodiment, the activity of EC 4.2.3.27 is isoprene synthase enzyme activity. The fermentation reactor(s) is then operated at conditions under which the recombinant host metabolizes the gaseous stream and produces a hydrocarbon. In one nonlimiting embodiment the hydrocarbon produced comprises one or more isoprene units as depicted in Formula I

or a salt or derivative thereof.

Another aspect of the present invention relates to a method for synthesizing a hydrocarbon in a host having one or more properties of *Cupriavidus necator*. In one nonlimiting embodiment, the hydrocarbon produced comprises one or more isoprene units as depicted in Formula I

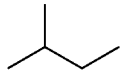
(I)

or a salt or derivative thereof. In one nonlimiting embodiment, the method comprises enzymatically converting glyceraldehyde-3-phosphate and pyruvate to 1 deoxy-d-xylulose-phosphate using a polypeptide having an activity of EC 2.2.1.7. In one nonlimiting embodiment, the activity of EC 2.2.1.7 is 1-deoxy-D-xylulose-5-phosphate synthase (DXS) activity. In this embodiment, the method may further comprise enzymatically converting dimethylallylpyrophosphate to a hydrocarbon comprising one or more isoprene units as depicted in Formula I

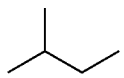
(I)

or a salt or derivative thereof using a polypeptide having an activity of EC 4.2.3.27. In one nonlimiting embodiment, the activity of EC 4.2.3.27 is isoprene synthase enzyme activity.

Another aspect of the present invention relates to a method for synthesizing a hydrocarbon in a host selected from non-pathogenic members of the genera *Ralstonia, Wausteria, Cupriavidus, Alcaligenes, Burkholderia* or *Pandoraea*. In one nonlimiting embodiment, the hydrocarbon produced comprises one or more isoprene units as depicted in Formula I

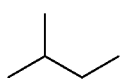
(I)

or a salt or derivative thereof. In one nonlimiting embodiment, the method comprises enzymatically converting glyceraldehyde-3-phosphate and pyruvate to 1 deoxy-d-xylulose-phosphate using a polypeptide having an activity of EC 2.2.1.7. In one nonlimiting embodiment, the activity of EC 2.2.1.7 is 1-deoxy-D-xylulose-5-phosphate synthase (DXS) activity. In this embodiment, the method may further comprise enzymatically converting dimethylallylpyrophosphate to a hydrocarbon comprising one or more isoprene units as depicted in Formula I

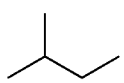
(I)

or a salt or derivative thereof using a polypeptide having an activity of EC 4.2.3.27. In one nonlimiting embodiment, the activity of EC 4.2.3.27 is isoprene synthase enzyme activity. Another aspect of the present invention relates to a recombinant host capable of producing a hydrocarbon from a gas stream. In one nonlimiting embodiment, the hydrocarbon produced comprises one or more isoprene units as depicted in Formula I

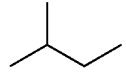
(I)

or a salt or derivative thereof.

In one nonlimiting embodiment, the recombinant host is capable of producing the hydrocarbon via a methylerythritol phosphate (MEP) pathway.

In one nonlimiting embodiment, the recombinant host comprises an exogenous nucleic acid sequence encoding a polypeptide having an activity of EC 4.2.3.27. In one nonlimiting embodiment, the activity of EC 4.2.3.27 is isoprene synthase enzyme activity.

In one nonlimiting embodiment, the recombinant host comprises an exogenous nucleic acid sequence encoding a polypeptide having an activity of EC 2.2.1.7 and an exogenous nucleic acid sequence encoding a polypeptide having an activity of EC 4.2.3.27.

Another aspect of the present invention relates to a host having one or more properties of *Cupriavidus necator* capable of producing a hydrocarbon from a gas stream. In one nonlimiting embodiment, the hydrocarbon produced comprises one or more isoprene units as depicted in Formula I

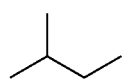
(I)

or a salt or derivative thereof.

Another aspect of the present invention relates to a recombinant *Cupriavidus necator* host capable of producing a hydrocarbon from a gas stream. In one nonlimiting embodiment, the hydrocarbon produced comprises one or more isoprene units as depicted in Formula I

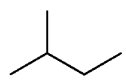
(I)

or a salt or derivative thereof.

Another aspect of the present invention relates to a method for producing a recombinant host capable of producing a hydrocarbon from a gas stream. In one nonlimiting embodiment, the hydrocarbon produced comprises one or more isoprene units as depicted in Formula I

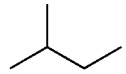
(I)

or a salt or derivative thereof. In one nonlimiting embodiment, the recombinant host is transfected with an exogenous nucleic acid encoding a polypeptide having an activity of EC 2.2.1.7. In one nonlimiting embodiment, the activity of EC 2.2.1.7 is 1-deoxy-D-xylulose-5-phosphate synthase (DXS) activity. In one nonlimiting embodiment of this method, a host cell is transfected with an exogenous nucleic acid sequence encoding a polypeptide having an activity of EC 4.2.3.27. In one nonlimiting embodiment, the activity of EC 4.2.3.27 is isoprene synthase enzyme activity. In one nonlimiting embodiment of this method, a host cell is transfected with an exogenous nucleic acid sequence encoding a polypeptide having an activity of EC 2.2.1.7 and an exogenous nucleic acid encoding a polypeptide having an activity of EC 4.2.3.27.

Another aspect of the present invention relates to a hydrocarbon, such as a bioderived hydrocarbon, produced in or obtainable from a recombinant host described herein. In one nonlimiting embodiment, the hydrocarbon produced comprises one or more isoprene units as depicted in Formula I

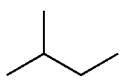
(I)

or a salt or derivative thereof.

Another aspect of the present invention relates to products such as bio-derived, bio-based, or fermentation-derived products, produced from or obtainable from any of the methods or hosts described herein.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and the drawings, and from the claims. The word "comprising" in the claims may be replaced by "consisting essentially of" or with "consisting of," according to standard practice in patent law.

DETAILED DESCRIPTION

Figure 1A:
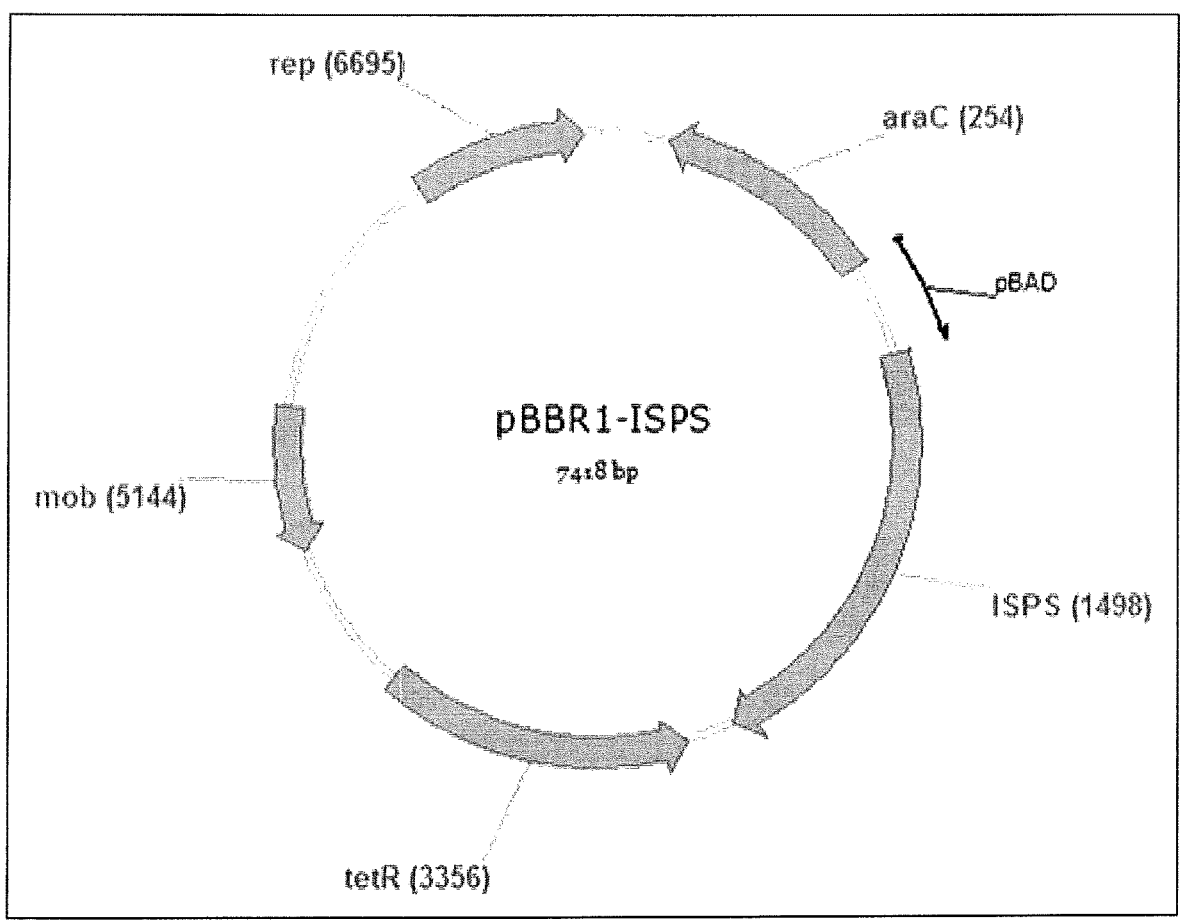
FIGS. 1A-1C are images of vectors pBBR1-ISPS (FIG. 1A), pBBR1-*E. coli* DXS-ISPS (FIG. 1B) and pBBR1-*B. subtilis* DXS-ISPS (FIG. 1C). Nucleic acid sequences of these vectors are set forth herein in SEQ ID NOs: 7 through 9, respectively.

Disclosed herein are biological systems, networks, and recombinant cells comprising an engineered enzymatic pathway that catalyze the conversion of a gas to a hydrocarbon, compositions and methods for their production, and methods for their use in production of hydrocarbons. The compositions and methods disclosed herein provide low cost processes for conversion of industrial gases to chemicals in a fermenter. In the methods of the present invention, recombinant cells are introduced into a fermenter, mixed with gas feedstocks which are enzymatically converted to a hydrocarbon by the recombinant cells, and the hydrocarbon is then separated from the off-gases from the fermenter.

By "recombinant cell" or "recombinant host" as used herein, it is meant to encompass any genetically engineered cell or host as described herein and such terms as recombinant, engineered, and genetically engineered are used interchangeably herein.

By "hydrocarbon" or "hydrocarbons" as used herein, it is meant to encompass any organic compound comprised of carbons and hydrogens which can be enzymatically synthesized from a gas and is inclusive of saturated as well as unsaturated structures with double or triple bonds formed between carbon atoms, ring structures, salts and derivatives thereof. In one nonlimiting embodiment, the hydrocarbon comprises one or more isoprene units as depicted in Formula I

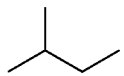
(I)

or a salt or derivative thereof.

By the phrase "one or more isoprene units as depicted in Formula I" it is meant to encompass any saturated or unsaturated 5 carbon branched structure derived from an isoprenoid including, isoprene as well as isoprenoids, terpenes and terpenoids as well as derivatives such as, but not limited to isoprenols, and salts thereof.

Nonlimiting examples of hydrocarbons comprising one or more isoprene units produced in accordance with the present invention include isoprene as well as any isoprenoid, terpene or terpenoid derivative of 5, including C5, C10, C15, C20, C25, C30, C35, C40, C45, C50, etc. Nonlimiting examples include hemiterpene, monoterpene, diterpene, triterpene, tetraterpene, polyterpene, lycopene, abietadiene, amorphadiene, carene, alpha-farnesene, beta-farnesene, farnesol, geraniol, geranylgeraniol, isoprene, linalool, limonene, myrcene, nerolidol, ocimene, patchoulol, beta-pinene, sabinene, gamma-terpinene, terpinolene and valencene, as well as derivatives and salts thereof.

In one nonlimiting embodiment, the present invention relates to methods for the design and subsequent introduction of non-native DNA into *Cupriavidus necator*, to produce the recombinant cells. In some non-limiting embodiments, the host of the present invention is *Cupriavidus necator*, such as a genetically engineered strain of *Cupriavidus necator* capable of stable hydrocarbon production. In one nonlimiting embodiment, the present invention relates to a *Cupriavidus necator* host capable of producing hydrocarbons via a methylerythritol phosphate (MEP) pathway. *Cupriavidus necator* is a Gram-negative, flagellated soil bacterium of the Betaproteobacteria class. This hydrogen-oxidizing bacterium is capable of growing at the interface of anaerobic and aerobic environments and easily adapts between heterotrophic and autotrophic lifestyles. Sources of energy for the bacterium include both organic compounds and hydrogen. *C. necator* does not naturally contain genes for isoprene synthase (ISPS) and therefore does not express this enzyme. Additional properties of *Cupriavidus necator* include microaerophilicity, copper resistance (Makar and Casida; 1987), bacterial predation (Byrd et al., 1985; Sillman & Casida, 1986; Zeph & Casida, 1986) and polyhydrobutyrate (PHB) synthesis. In addition, the cells have been reported to be capable of both aerobic and nitrate dependent anaerobic growth.

In another nonlimiting embodiment, the present invention relates to methods for the design and subsequent introduction of non-native DNA into a recombinant host having one or more of the above-mentioned properties of *Cupriavidus necator*.

In yet another nonlimiting embodiment, the present invention relates to methods for the design and subsequent introduction of non-native DNA into a recombinant host selected from non-pathogenic members of the genera *Ralstonia, Wausteria, Cupriavidus, Alcaligenes, Burkholderia* or *Pandoraea*.

The present invention provides methods and compositions for synthesizing hydrocarbons in these recombinant cells. In the methods and compositions of the present invention, a host of the invention, such as organisms such as *C. necator*, as well as non-pathogenic members of the genera *Ralstonia, Wausteria, Alcaligenes, Burkholderia* and *Pandoraea*, and other organisms having one or more of the above-mentioned properties of *Cupriavidus necator* can be used to synthesize hydrocarbons via a methylerythritol phosphate (MEP) pathway.

Surprisingly, the inventors herein have found that expression of a polypeptide having an activity of EC 2.2.1.7 and a polypeptide having an activity of EC 4.2.3.27 in *C. necator* resulted in the production of isoprene, via the MEP pathway. Specifically, recombinant *Cupriavidus necator* cells were transformed with novel non-native DNA encoding enzymes that catalyze the conversion of glyceraldehyde-3-phosphate and pyruvate to 1 deoxy-d-xylulose-phosphate, and dimethylallylpyrophosphate (DMAPP) to isoprene, in a plasmid, along with standard regulatory DNA elements. The effect of the addition of non-native gene encoding a polypeptide having an activity of EC 2.2.1.7 from *B. subtilis* and *E. coli* into *Cupriavidus necator* was to increase the flux through the native metabolic MEP pathway, which ultimately increases the flux of an added raw material to DMAPP. The addition of the non-native gene encoding a polypeptide having an activity of EC 4.2.3.27 allowed the recombinant cell to convert DMAPP to isoprene. Testing of the recombinant organism, referred to herein as DXS+/ISPS+, showed that isoprene was produced by the recombinant organism. Moreover, this recombinant organism produced more isoprene than a recombinant *Cupriavidus necator* in which only a non-native gene encoding a polypeptide having an activity of EC 4.2.3.27 was introduced (referred to herein ISPS+). *Cupriavidus necator* cells in which the non-native gene encoding a polypeptide having an activity of EC 4.2.3.27 is not added did not produce isoprene.

A nonlimiting example of a *C. necator* host useful in the present invention is a *C. necator* of the H16 strain. In one nonlimiting embodiment, a *C. necator* host of the H16 strain with the phaCAB gene locus knocked out (ΔphaCAB) is used.

In one nonlimiting embodiment, the method comprises enzymatically converting glyceraldehyde-3-phosphate and pyruvate to 1 deoxy-d-xylulose-phosphate using a polypeptide having an activity of EC 2.2.1.7, such as an enzyme with classification EC 2.2.1.7. In one nonlimiting embodiment, the activity of EC 2.2.1.7 is 1-deoxy-D-xylulose-5-phosphate synthase (DXS) activity. In one nonlimiting embodiment, the polypeptide is a 1-deoxy-D-xylulose-5-phosphate synthase (DXS). Polypeptides having DXS enzyme activity have been identified from various organisms and are readily available in publicly available databases such as GenBank or EMBL. Nonlimiting examples are the DXS of *E. coli* and *B. subtilis*. In one nonlimiting embodiment, the polypeptide having DXS enzyme activity has at least 70%, 75%, 80, 85, 90%, 91%, 92%, 93%, 94%, 95%, 96%, 97%, 98%, 99% or 99.5% sequence identity to the amino acid sequences set forth in SEQ ID NO: 1 or 2 or a functional fragment thereof. In one nonlimiting embodiment, the polypeptide having DXS enzyme activity comprises the amino acid sequence set forth in SEQ ID NO: 1 or 2 or a functional fragment thereof. In one nonlimiting embodiment, the polypeptide having DXS enzyme activity is encoded by a nucleic acid sequence having at least 70%, 75%, 80, 85, 90%, 91%, 92%, 93%, 94%, 95%, 96%, 97%, 98%, 99% or 99.5% sequence identity to the nucleic acid sequence set forth in SEQ ID NO: 4 or 5 or a functional fragment thereof. In one nonlimiting embodiment, the polypeptide having DXS enzyme activity is encoded by a nucleic acid sequence comprising the nucleic acid sequence set forth in SEQ ID NOs: 4 or 5 or a functional fragment thereof. In one nonlimiting embodiment, the nucleic acid sequence is codon optimized for *Cupriavidus necator*.

In one nonlimiting embodiment, the method further comprises enzymatically converting dimethylallylpyrophosphate to a hydrocarbon using a polypeptide having an activity of EC 4.2.3.27, such as an enzyme with classification EC 4.2.3.27. In one nonlimiting embodiment, the activity of EC 4.2.3.27 is isoprene synthase enzyme activity. In one nonlimiting embodiment, the polypeptide is an isoprene synthase enzyme Polypeptides having ISPS enzyme activity and nucleic acids encoding ISPSs have been identified from various organisms and are readily available in publicly available databases such as GenBank or EMBL. A nonlimiting example is the ISPS of *Populus alba*. In one nonlimiting embodiment, the polypeptide having ISPS enzyme activity has at least 49%, 50%, 55%, 60%, 65%, 70%, 75%, 80, 85, 90%, 91%, 92%, 93%, 94%, 95%, 96%, 97%, 98%, 99% or 99.5% sequence identity to the amino acid sequence set forth in SEQ ID NO: 3 or a functional fragment thereof. In one nonlimiting embodiment, the polypeptide having ISPS enzyme activity comprises the amino acid sequence set forth in SEQ ID NO: 3 or a functional fragment thereof. In one nonlimiting embodiment, the polypeptide having ISPS enzyme activity is encoded by a nucleic acid sequence having at least 49%, 50%, 55%, 60%, 65%, 70%, 75%, 80, 85, 90%, 91%, 92%, 93%, 94%, 95%, 96%, 97%, 98%, 99% or 99.5% sequence identity to the nucleic acid sequence set forth in SEQ ID NO: 6 or a functional fragment thereof. In one nonlimiting embodiment, the polypeptide having ISPS enzyme activity is encoded by a nucleic acid sequence comprising the nucleic acid sequence set forth in SEQ ID NO: 6 or a functional fragment thereof.

Figure 1B:
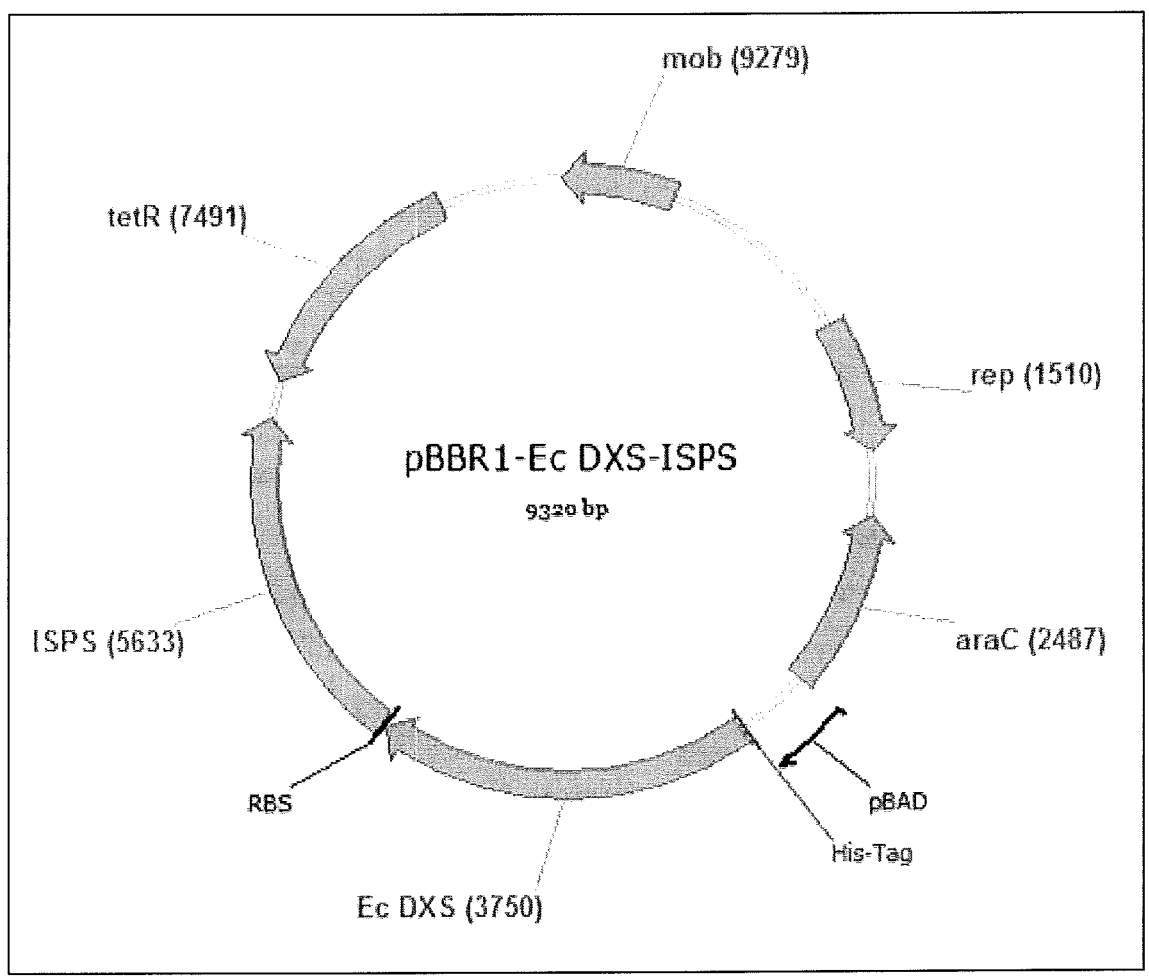
Figure 1C:
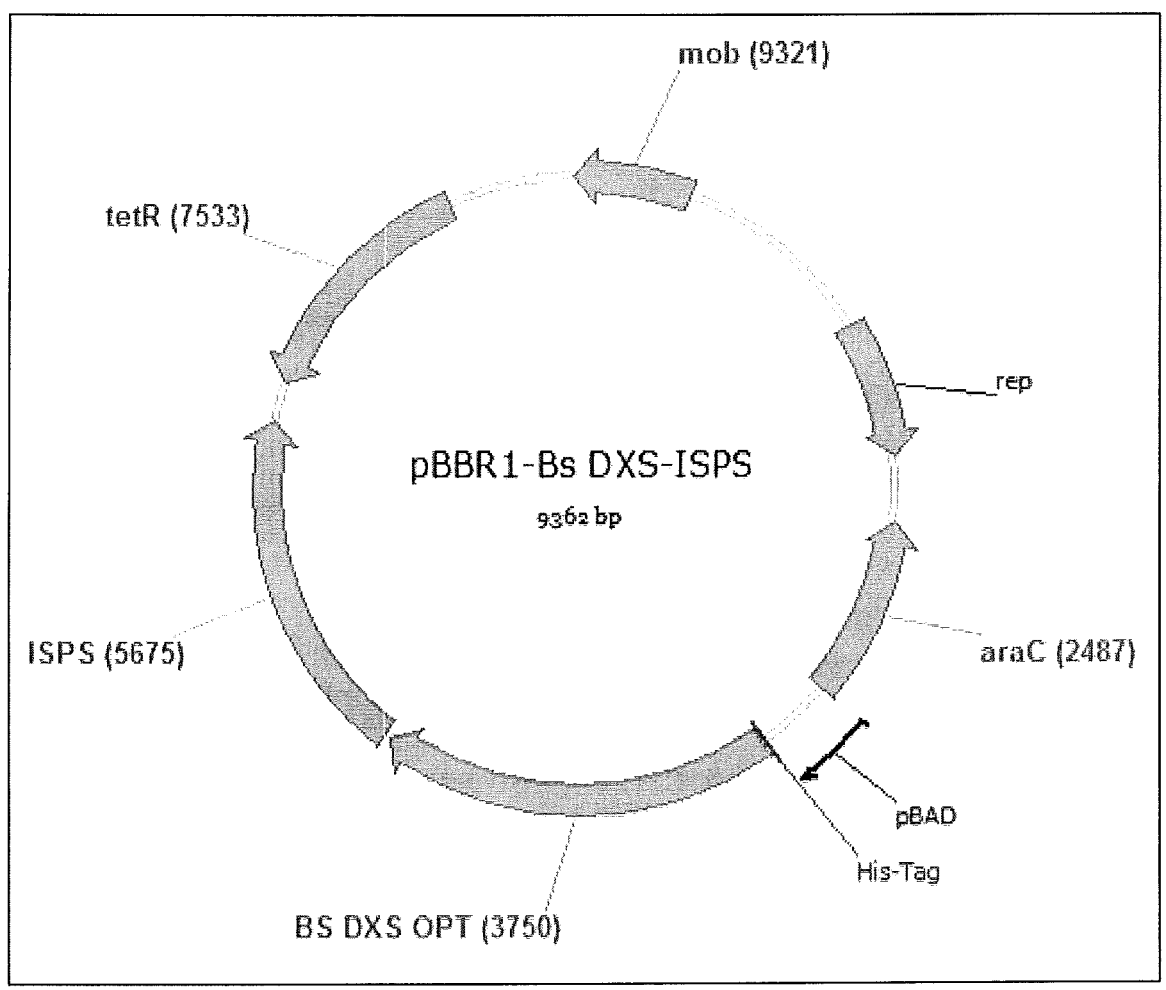
Figure 2:
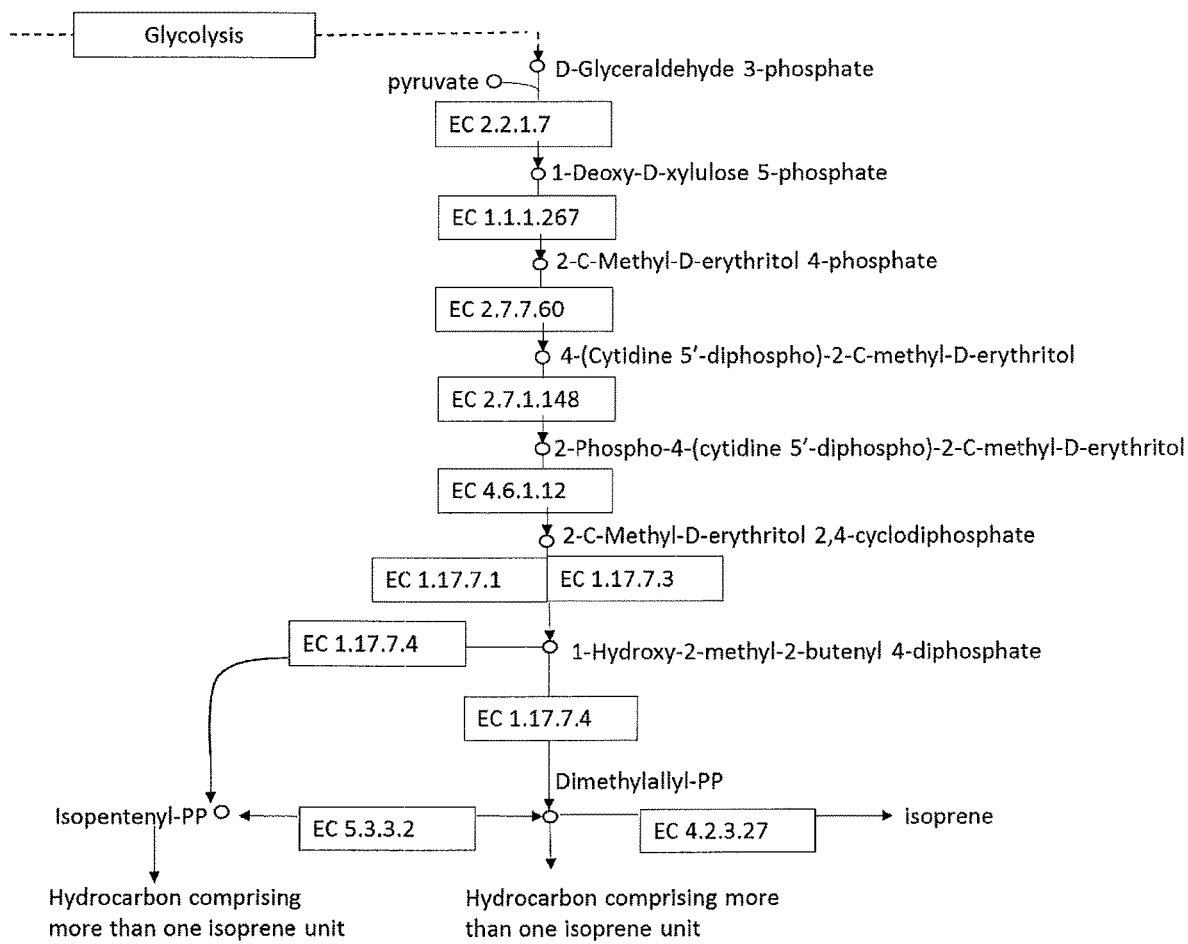
FIG. 2 is a schematic depicting biosynthesis of a hydrocarbon comprising one or more isoprene units via the MEP pathway.

Various vectors have been constructed for use in the present invention and confirmed by sequencing. Vectors constructed included pBBR1-ISPS, pBBR1-*E. coli* DXD-ISPS, and pBBR1-*B. subtilis* DXD-ISPS. Images of the constructed vectors are set forth in FIGS. 1A through 1C, respectively and their nucleic acid sequences are SEQ ID NOs: 7 through 9, respectively.

In one nonlimiting embodiment, the method for synthesizing a hydrocarbon in a recombinant host as described herein comprises enzymatically converting glyceraldehyde-3-phosphate and pyruvate to 1 deoxy-d-xylulose-phosphate using a polypeptide having an enzyme activity of EC 2.2.1.7 and enzymatically converting dimethylallylpyrophosphate to a hydrocarbon using a polypeptide having an enzyme activity of EC 4.2.3.27. In one nonlimiting embodiment, the enzyme activity of EC 2.2.1.7 is 1-deoxy-D-xylulose-5-phosphate synthase (DXS) activity. In one nonlimiting embodiment, the enzyme activity of EC 4.2.3.27 is ISPS enzyme activity. In one nonlimiting embodiment, the hydrocarbon comprises one or more isoprene units as depicted in Formula I

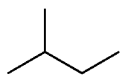

(I)

or a salt or derivative thereof. In this embodiment, any of the polypeptides having an EC 2.2.1.7 enzyme activity or EC 4.2.3.27 enzyme activity described supra can be used.

The percent identity (homology) between two amino acid sequences can be determined as follows. First, the amino acid sequences are aligned using the BLAST 2 Sequences (B12seq) program from the stand-alone version of BLAST containing BLASTP version 2.0.14. This stand-alone version of BLAST can be obtained from the U.S. government's National Center for Biotechnology Information web site (www with the extension ncbi.nlm.nih.gov). Instructions explaining how to use the B12seq program can be found in the readme file accompanying BLASTZ. B12seq performs a comparison between two amino acid sequences using the BLASTP algorithm. To compare two amino acid sequences, the options of B12seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\B12seq-i c:\seq1.txt-j c:\seq2.txt-p blastp-o c:\output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity (or homology) is determined by dividing the number of matches by the length of the full-length polypeptide amino acid sequence followed by multiplying the resulting value by 100. It is noted that the percent identity (or homology) value is rounded to the nearest tenth. For example, 90.11, 90.12, 90.13, and 90.14 is rounded down to 90.1, while 90.15, 90.16, 90.17, 90.18, and 90.19 is rounded up to 90.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the polypeptides or nucleic acid sequences described herein can also be used in the methods of the document. The term "functional fragment" as used herein refers to a peptide fragment of a polypeptide or a nucleic acid sequence fragment encoding a peptide fragment of a polypeptide that has at least 25% (e.g., at least: 30%; 40%; 50%; 60%; 70%; 75%; 80%; 85%; 90%; 95%; 98%; 99%; 100%; or even greater than 100%) of the activity of the corresponding mature, full-length, polypeptide. The functional fragment can generally, but not always, be comprised of a continuous region of the polypeptide, wherein the region has functional activity.

In one nonlimiting embodiment, methods of the present invention are performed in a recombinant *Cupriavidus necator* host.

In another nonlimiting embodiment, methods of the present invention are performed in a recombinant host having one or more of the above-mentioned properties of *Cupriavidus necator*.

In yet another nonlimiting embodiment, methods of the present invention are performed in a recombinant host selected from non-pathogenic members of the genera *Ralstonia, Wausteria, Cupriavidus, Alcaligenes, Burkholderia* or *Pandoraea*.

Recombinant hosts can naturally express none or some (e.g., one or more, two or more) of the enzymes of the pathways described herein. Endogenous genes of the recombinant hosts also can be disrupted to prevent the formation of undesirable metabolites or prevent the loss of intermediates in the pathway through other enzymes acting on such intermediates. Recombinant hosts can be referred to as recombinant host cells, engineered cells, or engineered hosts. Thus, as described herein, recombinant hosts can include exogenous nucleic acids encoding one or more of IDIs and/or ISPSs, as described herein.

The term "exogenous" as used herein with reference to a nucleic acid (or a protein) and a host refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. An exogenous sequence may therefore be integrated into the genome of the host. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

In a non-limiting embodiment, a method of hydrocarbon production as described herein is carried out using any host of the invention.

In a non-limiting embodiment is provided the use of a host of the invention, such as a recombinant or genetically engineered host as described herein, for the production of a hydrocarbon. The use may involve any method of hydrocarbon production as described herein.

In one nonlimiting embodiment of the present invention, the method for hydrocarbon production is performed in a recombinant host comprising an exogenous nucleic acid sequence encoding a polypeptide having an enzyme activity of EC 2.2.1.7. In one nonlimiting embodiment, the enzyme activity of EC 2.2.1.7 is DXS enzyme activity. In this embodiment, any of the nucleic acid sequences encoding a polypeptide having an EC 2.2.1.7 enzyme activity as described supra can be used.

In another nonlimiting embodiment, the method is performed using a recombinant host comprising an exogenous nucleic acid encoding a polypeptide having an enzyme activity of EC 2.2.1.7 and an exogenous nucleic acid encoding a polypeptide having an enzyme activity of EC 4.2.3.27. In one nonlimiting embodiment, the enzyme activity of EC 2.2.1.7 is DXS enzyme activity. In one nonlimiting embodiment, the enzyme activity of EC 4.2.3.27 is ISPS enzyme activity. In this embodiment, any of the nucleic acid sequences encoding a polypeptide having an EC 2.2.1.7 enzyme activity and any of the nucleic acid sequences having an EC 4.2.3.27 enzyme activity as described supra can be used.

In another nonlimiting embodiment, the method for hydrocarbon production of the present invention is performed in a recombinant host which has been transformed with a vector comprising any of SEQ ID NOs:7, 8 or 9.

In some non-limiting embodiments, the method comprises contacting a host of the invention with a suitable substrate under conditions such that the host is capable of producing a hydrocarbon from the substrate via a MEP pathway. Such a method may comprise culturing a host of the invention in the presence of a suitable substrate. In some non-limiting embodiments, the substrate comprises glyceraldehyde-3-phosphate and/or pyruvate, or the substrate can be converted to form glyceraldehyde-3-phosphate and/or pyruvate by the host.

In some non-limiting embodiments, the method of the invention comprises a fermentation reaction and the method is carried out in a fermentation reactor. In any of the methods described herein, a fermentation strategy can be used that entails anaerobic, micro-aerobic or aerobic cultivation. A variety of fermentation strategies can be employed with the present invention, and are familiar to one skilled in the art. Examples include batch, fed batch and continuous systems including chemostat, auxostat and may utilize cell retention or concentration systems to increase biomass, for example. Retention/concentration systems can include hydrocyclones, cross flow/tangential flow filtration, inclined settlers and process centrifuges. A fermentation strategy can entail nutrient limitation such as nitrogen, phosphate or oxygen limitation. The substrate, or the principal carbon source fed to the fermentation, can be or can derive from a biological or non-biological feedstock. The biological feedstock can be, or can derived from, monosaccharides, disaccharides, lignocellulose, hemicellulose, cellulose, lignin, levulinic acid and formic acid, triglycerides, glycerol, fatty acids, agricultural waste, condensed distillers' solubles or municipal waste. The non-biological feedstock can be, or can derive from, natural gas, syngas, $CO_2/H_2$, methanol, ethanol, non-volatile residue, caustic wash from cyclohexane oxidation processes, or waste stream, or derivative thereof, optionally obtained from a chemical or petrochemical industry.

In one nonlimiting embodiment, at least one of the enzymatic conversions of the hydrocarbon production method comprises gas fermentation within the recombinant host. In this embodiment, a gaseous stream is provided to a fermentation reactor, also known as a bioreactor. A recombinant host as described supra is also added to the fermentation reactor. The fermentation reactor is then operated at conditions under which the recombinant host metabolizes the gaseous stream and produces the hydrocarbon. In this embodiment, the gas fermentation may comprise at least one of natural gas, syngas, $CO_2/H_2$, methanol, ethanol, non-volatile residue, caustic wash from cyclohexane oxidation processes, or waste stream, or derivative thereof, optionally obtained from a chemical or petrochemical industry. In one nonlimiting embodiment, the gas fermentation comprises $CO_2/H_2$ or syngas.

In some non-limiting embodiments the substrate is a gas. In some non-limiting embodiments, the method comprises contacting the host with a gas. In some of these embodiments, the gas comprises at least one of natural gas, syngas, $CO_2/H_2$, methanol, ethanol, non-volatile residue, caustic wash from cyclohexane oxidation processes, or waste stream, or derivative thereof, optionally obtained from a chemical or petrochemical industry. In one non-limiting embodiment, the gas comprises $CO_2/H_2$ or syngas.

In one nonlimiting embodiment, the fermentation reactor is fed at least one growth rate limiting nutrient such as described in PCT/EP2010/054401, teachings of which are incorporated herein by reference. In one nonlimiting embodiment, the fermentation reactor is operated under phosphate limiting conditions such as described in U.S. Pat. No. 4,605,620, teachings of which are herein incorporated by reference. More specifically, the information in the Examples of U.S. Pat. No. 4,605,620 is hereby incorporated by reference in its entirety.

The methods of the present invention may further comprise recovering produced hydrocarbon from the recombinant host. In these embodiments, the hydrocarbons may comprise one or more isoprene units, as described herein.

In some non-limiting embodiments, the hydrocarbon produced by a method of the invention is a gas. In some non-limiting embodiments the method further comprises recovering produced gaseous hydrocarbon from the host.

Once produced, any method can be used to isolate the hydrocarbon. For example, the hydrocarbon isoprene can be recovered from the fermenter off-gas stream as a volatile product as the boiling point of isoprene is 34.1° C. One nonlimiting example of a fermentation range of the present invention is about 20° C. to 60° C. One nonlimiting example of a preferred fermentation range is about 25° C. to 42° C.

Isoprene has a high vapor pressure and can be stripped by the gas flow rate through the broth for recovery from the off-gas. Isoprene can be selectively adsorbed onto, for example, an adsorbent and separated from the other off-gas components. Similar isolated methods can be adapted routinely for other hydrocarbons produced in accordance with the present invention.

Membrane separation technology may also be employed to separate the hydrocarbon from the other off-gas compounds. For example, the hydrocarbon isoprene may be desorbed from an adsorbent using, for example, nitrogen and condensed at low temperature and high pressure.

Because of the gaseous nature of isoprene, in embodiments of the present invention wherein the hydrocarbon produced is isoprene, an advantage is easy separation of the product.

Compositions for synthesizing hydrocarbons in recombinant hosts also provided by the present invention.

In one nonlimiting embodiment, a recombinant host capable of producing a hydrocarbon via a methylerythritol phosphate (MEP) pathway is provided. The host may be any host as described herein that capable of producing a hydrocarbon via a MEP pathway. In one nonlimiting embodiment, the recombinant host is a substantially pure culture.

As used herein, a "substantially pure culture" of a recombinant host microorganism is a culture of that microorganism in which less than about 40% (i.e., less than about 35%; 30%; 25%; 20%; 15%; 10%; 5%; 2%; 1%; 0.5%; 0.25%; 0.1%; 0.01%; 0.001%; 0.0001%; or even less) of the total number of viable cells in the culture are viable cells other than the recombinant microorganism, e.g., bacterial, fungal (including yeast), mycoplasmal, or protozoan cells. The term "about" in this context means that the relevant percentage can be 15% of the specified percentage above or below the specified percentage. Thus, for example, about 20% can be 17% to 23%. Such a culture of recombinant microorganisms includes the cells and a growth, storage, or transport medium. Media can be liquid, semi-solid (e.g., gelatinous media), or frozen. The culture includes the cells growing in the liquid or in/on the semi-solid medium or being stored or transported in a storage or transport medium, including a frozen storage or transport medium. The cultures are in a culture vessel or storage vessel or substrate (e.g., a culture dish, flask, or tube or a storage vial or tube).

In one nonlimiting embodiment, the recombinant host comprises an exogenous nucleic acid sequence encoding a polypeptide having an enzyme activity of EC 2.2.1.7. In one nonlimiting embodiment, the enzyme activity of EC 2.2.1.7 is DXS enzyme activity. Any nucleic acid sequence encoding a polypeptide having an enzyme activity of EC 2.2.1.7 as described supra can be used in this embodiment.

In another nonlimiting embodiment, the recombinant host comprises an exogenous nucleic acid encoding a polypeptide having an enzyme activity of EC 2.2.1.7 and an exogenous nucleic acid encoding a polypeptide having an enzyme activity of EC 4.2.3.27. In one nonlimiting embodiment, the enzyme activity of EC 2.2.1.7 is DXS enzyme activity. In one nonlimiting embodiment, the enzyme activity of EC 4.2.3.27 is ISPS enzyme activity. Any of the nucleic acid sequences encoding a polypeptide having an enzyme activity of EC 2.2.1.7 or an enzyme activity of EC 4.2.3.27 as described supra can be used.

In one nonlimiting embodiment, at least one of the exogenous nucleic acid sequences in the recombinant host is contained within a plasmid.

In one nonlimiting embodiment, at least one of the exogenous nucleic acid sequences is integrated into a chromosome of the host.

In one nonlimiting embodiment, the recombinant host has been transfected with a vector comprising any of SEQ ID NOs:7, 8 or 9.

Also provided by the present invention are hydrocarbons bioderived from, produced by, or obtainable from, a recombinant host according to any of methods described herein. In one nonlimiting embodiment, the hydrocarbon has carbon isotope ratio that reflects an atmospheric carbon dioxide uptake source. Examples of such ratios include, but are not limited to, carbon-12, carbon-13, and carbon-14 isotopes.

In addition, the present invention provides a product such as a bio-derived, bio-based, or fermentation-derived product produced using the methods and/or compositions disclosed herein. Examples of such products include, but are not limited to, compositions comprising at least one bio-derived, bio-based, or fermentation-derived compound or any combination thereof, as well as polymers, rubbers such as cis-polyisoprene rubber, trans-polyisoprene rubber, or liquid polyisoprene rubber, molded substances, formulations and semi-solid or non-semi-solid streams comprising one or more of the bio-derived, bio-based, or fermentation-derived compounds or compositions, combinations or products thereof.

In addition, the present invention provides methods of producing such a product. In some non-limiting embodiments, the method comprises producing a hydrocarbon by a method of the invention and converting the hydrocarbon to said product. In one non-limiting embodiment, a method of producing a polymer comprises the steps of producing a hydrocarbon by a method as described herein and forming a polymer from said hydrocarbon.

Although specific advantages have been enumerated above, various embodiments may include some, none, or all of the enumerated advantages. Further, other technical advantages may become readily apparent to one of ordinary skill in the art after review of the figures and description herein. It should be understood at the outset that, although exemplary embodiments are illustrated in the figures and described herein, the principles of the present disclosure may be implemented using any number of techniques, whether currently known or not. The present disclosure should in no way be limited to the exemplary implementations and techniques illustrated in the drawings and described herein.

Unless otherwise specifically noted, articles depicted in the drawings are not necessarily drawn to scale.

Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

The following section provides further illustration of the methods and compositions of the present invention. These working examples are illustrative only and are not intended to limit the scope of the invention in any way.

EXAMPLES

Example 1: Primers

Primers as listed in Table 1 were used in the following disclosed experiments.

TABLE 1

| Primer | Sequence |
|---|---|
| 1 | 5' GGAAGGAGCGAAGCATGCGTTGTAGCGTTAGC 3' (SEQ ID NO: 10) |
| 2 | 5' GGGCTTTGTTAGCAGGCTTAGCGTTCGAACGGCAGAAT 3' (SEQ ID NO: 11) |
| 3 | 5' GCCTGCTAACAAAGCCCGAAA 3' (SEQ ID NO: 12) |
| 4 | 5' GCTTCGCTCCTTCCTTAAAG 3' (SEQ ID NO: 13) |
| 5 | 5' GCCGCCCTATACCTTGTCT 3' (SEQ ID NO: 14) |
| 6 | 5' ACGGCGTCACACTTTGCTAT 3' (SEQ ID NO: 15) |
| 7 | 5' CGCGTCGCGAACGCCAGCAA 3' (SEQ ID NO: 16) |
| 8 | 5' ACGGGGCCTGCCACCATACC 3' (SEQ ID NO: 17) |
| 9 | 5' CTTATCGATGATAAGCTGTC 3' (SEQ ID NO: 18) |
| 10 | 5' CAGCCCTAGATCGGCCACAG 3' (SEQ ID NO: 19) |
| 11 | 5' TGCCTGCCCCTCCCTTTTGG 3' (SEQ ID NO: 20) |
| 12 | 5' GCGGCGAGTGCGGGGGTTCC 3' (SEQ ID NO: 21) |
| 13 | 5' GGAAACCCACGGCGGCAATG 3' (SEQ ID NO: 22) |
| 14 | 5' ATCGGCTGTAGCCGCCTCTAGATT 3' (SEQ ID NO: 23) |
| 15 | 5' AGTAACAATTGCTCAAGCAG 3' (SEQ ID NO: 24) |
| 16 | 5' ATTCAGAGAAGAAACCAATT 3' (SEQ ID NO: 25) |
| 17 | 5' GCTAGAAATAATTTTGAGCTCAGGAAGGAGCGAAGCATGGGCCATCATCATCATCATCACATGAGTTTTGATATTGCC 3' (SEQ ID NO: 26) |
| 18 | 5' GCTTCGCTCCTTCCTTAAAGTTATGCCAGCCAGGCCTT 3' (SEQ ID NO: 27) |
| 19 | 5' GCTAGAAATAATTTTGAGCTCAGGAAGGAGCGAAGCATGGGCCATCATCATCATCATCACATGCTGGATCTGCTGTCGATC 3' (SEQ ID NO: 28) |
| 20 | 5' GCTTCGCTCCTTCCTTAAAGTCACGAGCCGATGCCCTT 3' (SEQ ID NO: 29) |
| 21 | 5' CACTTTGCTATGCCATAGC 3' (SEQ ID NO: 30) |
| 22 | 5' CTGCGGCGAGCTTCGGTTTC 3' (SEQ ID NO: 31) |
| 23 | 5' GACTCCCTGAAGTACATGCTCG 3' (SEQ ID NO: 32) |

Example 2: Genes

Genes as listed in Table 2 were used in the following disclosed experiments.

TABLE 2

| Gene name | Species of origin | Database identifier |
|---|---|---|
| Isoprene synthase | *Populus alba* | BAD98243.1 |
| 1-deoxy-D-xylulose-5-phosphate synthase | *Escherichia coli* BL21 | NC_012892.2 |
| 1-deoxy-D-xylulose-5-phosphate synthase | *Bacillus subtilis* subsp. *subtilis* str. 168 | NP_390307.1 |

Example 3: Cloning of Poplar ISPS for Expression in *C. necator* spp.

The protein sequence for the *Populus alba* was obtained from GenBank and the full gene, codon optimized for *E. coli* was purchased from Eurofins MWG. This DNA was used as a template for amplification of the gene using primers 1 and 2 (see Table 1) and Phusion polymerase (NEB) with an annealing temperature of 45° C. The vector backbone of pBBR1MCS3-pBAD was generated with primer 3 and 4 (see Table 1) and with Merck Millipore KOD polymerase with annealing temperatures of 50-55° C. The two fragments were ligated using NEB Gibson Assembly reaction master mix as per the manufacturer's recommended protocol. The ligation mix was transformed into chemically competent *E. coli* NEB5α and correct clones verified via a combination of colony PCR and sequencing with primers 5 and 6 (see Table 1). Subsequently the whole construct was sequenced by MWG-Eurofins using primers 7-16 (see Table 1). A single verified construct was taken forward for further work and designated pBBR1-ISPS.

Example 4: Cloning of DXS-ISPS Bicistrons for Expression in *C. necator* spp.

A unique SacI restriction site was identified in pBBR1-ISPS, upstream of the ribosome binding site and downstream of the predicted transcriptional start site. pBBR1-ISPS was purified from NEB5α alpha using the Qiagen plasmid Midi prep kit, cut with SacI (NEB) and purified using the Qiagen PCR purification kit as per the recommended protocol. Nucleic acid sequences for DXSs from *E. coli* and *B. subtilis* were obtained from GenBank. *E. coli* DXS was amplified from genomic DNA. *B. subtilis* DXS was amplified from a codon optimized (*C. necator*) synthetic operon purchased from Eurofins MWG.

PCR products were generated with Merck Millipore KOD polymerase and an annealing temperature of 55° C. and using primers 17-20 (see Table 1) and purified by gel extraction using the Qiagen Gel Extraction kit and the recommended protocol. The purified DNA fragments were then used in a Gibson assembly with the SacI digested and purified pBBR1-ISPS and individual ligations transformed to E. coli NEB5α. Clones were verified via a combination of colony PCR with Taq polymerase (NEB) and sequencing with primers 21 to 23 (see Table 1). Single verified constructs representing each DXS coupled to ISPS were designated pBBR1-EC DXS-ISPS and pBBR1-BS DXS-ISPS.

Example 5: Vector Preparation and Transference to C. Necator H16 ΔphaCAB

Vectors pBBR1-EC DXS-ISPS and pBBR1-BS DXS-ISPS were prepared from their respective NEB5α hosts using the Qiagen Midi prep kit and appropriate culture volumes. A C. necator H16 strain with the phaCAB gene locus knocked out (ΔphaCAB) was grown to mid/late exponential phase in tryptic soy broth (TSB) media at 30° C. Cells were made competent with glycerol washes and used immediately. Competent cells were transformed with at least 1 μg of vector DNA via electroporation and recovered in TSB medium. Transformants were identified on TSB agar with 10 μg/ml tetracycline. Single transformants representative of each DXS-ISPS clone were further examined.

Example 6: Fermentation

Fermentations were by continuous cultivation with cell dilution rate of D=0.05 h$^{-1}$ and employed cell retention. Limitation was on phosphate with feeds being supplied at a total of 120 g/h. The pH was controlled at 6.6±0.05 and temperature at 30° C. DO (dissolved oxygen) is maintained by traditional methods such as cascading to the mixing speed and/or controlling oxygen/air sparge. Alternatively, DO is maintained using methods employed for gas fermentations. The DO uses three systems; (i) controlling the airflow and DO directly below 10% through an autotrophic start-up phase followed by (ii) bespoke off-gas control whereby an off-gas controller cascades to DO and sparge below a 5% DO setpoint. Alternatively, (iii) the DO can be controlled by a pre-determined gas blend below the flammability limits that is sparged and may be recirculated in the system. In such an approach oxygen/air can be supplemented to maintain DO required for growth and productivity.

The mass of the cultivations was maintained at 1.1 kg by removal of the permeate. The vectors were maintained by the addition of Tetracycline Hydrochloride at 20 μg/ml to the feeds and media. Fermentations were inoculated by 100 g shake flask culture grown on a rich media at 30° C. (15 g/L Neutralized soya peptone and 5 g/L Yeast extract) into 1 kg of fermentation media. Broth samples were taken during the course of the fermentation, 2 mL being analyzed for isoprene by GC-MS headspace analysis. Induction was by 0.2% w/v Arabinose. Fermentation media and feed are shown in Table 3 and components of the trace metal solution are shown in Table 4.

TABLE 3

| Main components | Initial Charge g/kg | Mineral feed (100 g/h) g/kg | phosphate feed (pH 7) (20 g/h) g/kg |
|---|---|---|---|
| Citric acid | 0.5 | | |
| KH$_2$PO$_4$ | 0.383 | | 0.953 |
| Na$_2$HPO$_4$ | 0.383 | | 1.556 |
| (NH$_4$)$_2$SO$_4$ | 1.24 | 1.24 | |
| MgSO$_4$•7H$_2$O | 0.5 | 0.5 | |
| CaCl$_2$•2H$_2$O | 0.01 | 0.01 | |
| Fe(NH$_4$)-citrate | 0.05 | 0.05 | |
| D-Fructose | 5 | 50 | |

| | mL/kg | mL/kg | |
|---|---|---|---|
| Trace metal solution | 10 | 10 | |

| Vitamins | g/kg | g/kg | |
|---|---|---|---|
| Thiamine-HCl | 0.01 | 0.001 | |
| Nicotinic acid | 0.01 | 0.001 | |
| Ca pantothenate | 0.03 | 0.003 | |
| Pyridoxine-HCl | 0.01 | 0.001 | |
| Biotin | 0.006 | 0.0006 | |

| | mL/kg | mL/kg | |
|---|---|---|---|
| Antifoam 204 | 0.1 | 0.1 | |
| Tetracycline Hydrochloride (20 mg/mL) | 1 | 1 | 1 | pH 6.6 with 1M NaOH/Ammonium Hydroxide

TABLE 4

| Component | Unit [g/L] |
|---|---|
| ZnSO$_4$•7H$_2$O | 0.1 |
| MnCl$_2$•4H$_2$O | 0.03 |
| H$_3$B$_3$O$_3$ | 0.3 |
| CoCl$_2$•6H$_2$O | 0.2 |
| NiSO$_4$•6H$_2$O | 0.025 |
| Na$_2$MoO$_4$•2H$_2$O | 0.03 |
| CuSO$_4$•5H$_2$O | 0.015 | pH 2 with HCl Made up to volume with deionised water

Example 7: GC MS-Based *Cupriavidus necator* In Vivo Isoprene Assay

To test *Cupriavidus necator* strains, DXS+/ISPS+, DXS−/ISPS+, DXS−/ISPS−, 20 ml Tryptic Soy Broth without dextrose (TSB-D) medium supplied with respective antibiotics were inoculated for each strain in 250 ml flasks and incubated at 30° C. for 48 hours with 230 rpm shaking. These pre-cultures were used to inoculate (1:50) 50 ml cultures in 250 ml flasks (TSB-D with antibiotics) and incubation followed for 7 hours after which time the cultures were induced with 1% arabinose and left again overnight at 30° C. at 230 rpm. Cultures were harvested (20 min, RT, 6000G) and the produced wet cell weight (WCW) was estimated. Cell pellets were subsequently resuspended in fresh TSB-D medium supplemented with antibiotic and inducer to achieve final cell density preferably 0.2 g WCW/ml. 2 ml of fresh TSB-D medium with antibiotic and inducer were distributed in duplicate to clean GC vials. 20 μl of the respective cell suspensions were used to inoculate the medium directly in the GC vials. The vials were closed and incubated 24 h at 30° C. with 160 rpm. Samples were analyzed with GC MS for the presence of isoprene. Results are shown in Table 5.

TABLE 5

| strain | isoprene detected [ppm] | std dev |
| --- | --- | --- |
| DXS+/ISPS+ | 1.709 | 0.156 |
| DXS−/ISPS+ | 0.082 | 0.002 |
| DXS−/ISPS− | 0.011 | 0.002 |

Example 8: Stock Solution of Isoprene and Standards 1000 ppm of Isoprene in methanol was prepared in ice. The 20, 100, 200, 300 and 600 ppm standards were also prepared in methanol on ice. 1990 ul of broth spiked with 10 ul Isoprene in methanol to give the corresponding:
 0.1 ppm (10 ul of 20 ppm)
 0.5 ppm (10 ul of 100 ppm)
 1.0 ppm (10 ul of 200 ppm)
 1.5 ppm (10 ul of 300 ppm)
 3.0 ppm (10 ul of 600 ppm)
 5.0 ppm (10 ul of 1000 ppm)

Example 9: GCMS Equipment and General Conditions

Two GCMS Agilent equipment were used.

The gas chromatograph 7890A (Agilent) equipped with an electronically controlled split/split-less injection port was interfaced to a single quadropule 5975C inert XLMSD (Agilent) with Triple Axis detector with an electron impact ionization chamber. The instrument was equipped with a MultiPurposeSampler MPS (Gerstel) equipped with Head Space (HS) injection mono head device with a 2.5 ml syringe (010055-025-00, Gerstel). GC separation was performed on DB-624 capillary column, 30 m, 0.25 mm i.d., 0.25 µm film thickness, for dimensions (122-1334, J&W Scientific, Agilent). The gas chromatograph 7890A (Agilent) equipped with an electronically controlled split/split-less injection port was interfaced to a single quadropule 5977A MSD (Agilent) detector with an electron impact ionization chamber. The instrument was equipped with a MultiPurposeSampler MPS (Gerstel) equipped with Head Space (HS) injection dual head device with a 2.5 ml syringe (010055-025-00, Gerstel). GC separation was performed on DB-624 capillary column, 60 m, 0.25 mm i.d., 0.25 µm film thickness, for dimensions (122-1364, J&W Scientific, Agilent).
The liners used were Ultra Inert glass. (5190-3983, Agilent). The septa used was Premium Inlet (5183-4757, Agilent). Liner and septa were replaced before each analytical run.

Helium was the carrier gas with a constant flow of 2 ml/min. The initial pressure was constant but increasing along the chromatographic run. The septum purge flow was 3 ml/min and the gas saver was on at 20 ml/min after 2 minutes.
The MS transfer line temperature was held at 260° C. Mass spectrometer was set with a set an electron impact ionization energy of 70 eV. The instrument was tuned daily with PFTBA to check its performance and quality of signal. The tune file was selected as atune.u from the corresponding tuning folder.
Agilent Chemstation and/or Mass Hunter were the acquisition software used for data collection/processing. A summary of GCMS specific conditions is provided in Tables 6A through 6C.

TABLE 6A

| GCMS CONDITIONS (7890A-5975C) MPS Gerstel | | |
| --- | --- | --- |
| PARAMETER | | VALUE |
| Carrier Gas | | Helium at constant flow (2.0 ml/min) |
| Injector | Split ratio | 1:10 |
| | Temperature | 150° C. |
| Detector | Source Temperature | 230° C. |
| | Quad Temperature | 150° C. |
| | Interface | 260° C. |
| | Gain | 2 |
| | Scan Range | m/z 28-200 |
| | Threshold | 150 |
| | Scan Speed | 4 |
| | 2^2(A/D samples) | |
| | Sampling Rate | |
| | 2^n = 2^2 | |
| | Mode | SCAN and SIM |
| Solvent delay * | 1.83 min | |
| Oven Temperature | Initial T: 40° C. × 3.1 min | |
| Oven Temperature | Initial T: 40° C. × 3.1 min | |
| Oven Ramp | 120° C./min to 260° C. for 5 min | |
| Injection volume | 500 µl from the Head Space | |
| Gas saver | On after 2 min | |
| Range | 0.1 ppm-5.0 ppm | |
| GC Column | DB-624 30 m × 250 µm × 1.4 µm | |

TABLE 6B

| GCMS CONDITIONS (7890B-5977A) MPS Gerstel | | |
| --- | --- | --- |
| PARAMETER | | VALUE |
| Carrier Gas | | Helium at constant flow (2.0 ml/min) |
| Injector | Split ratio | Splitless |
| | Temperature | 250° C. |
| Detector | Source Temperature | 230° C. |
| | Quad Temperature | 150° C. |
| | Interface | 260° C. |
| | Gain | 2 |
| | Scan Range | m/z 28-200 |
| | Threshold | 150 |
| | Scan Speed | 4 |
| | 2^2(A/D samples) | |
| | Sampling Rate | |
| | 2^n = 2^2 | |
| | Mode | SCAN and SIM |
| Solvent delay * | 5.50 min | |
| Oven Temperature | Initial T: 40° C. × 7.5 min | |
| Oven Ramp | 120° C./min to 260° C. for 5 min | |
| Injection volume | 500 µl from the Head Space | |
| Gas saver | On after 2 min | |
| Range | 0.1-5.0 ppm | |
| GC Column | DB-624 60 m × 250 µm × 1.4 µm | |

TABLE 6C

| Compound | Ions monitored in SIM Mode (m/z) |
| --- | --- |
| Isoprene | 39, 53, 67 |

Ions monitored for Isoprene on SIM mode

What is claimed is:

1. A method for biosynthesising a hydrocarbon in a recombinant host, said method comprising:
   providing a fermentation reactor,
   adding to the fermentation reactor a recombinant host consisting of a non-pathogenic member of the genera *Ralstonia, Wausteria, Cupriavidus, Alcaligenes, Burkholderia* or *Pandoraea* modified to comprise a non-native, exogenous nucleic acid sequence encoding a polypeptide having an enzyme activity of EC 2.2.1.7 which increases flux through a native metabolic 2-C-methyl-D-erythritol 4-phosphate (MEP) pathway of said host, and
   providing a stream comprising a gas comprising at least one of natural gas, methanol, ethanol, non-volatile residue, caustic wash from cyclohexane oxidation processes, or waste stream, or derivative thereof, optionally obtained from a chemical or petrochemical industry or a biological or nonbiological feedstock to the fermentation reactor, and
   operating the fermentation reactor at conditions for said recombinant host consisting of the non-pathogenic member of the genera *Ralstonia, Wausteria, Cupriavidus, Alcaligenes, Burkholderia* or *Pandoraea* modified to comprise the non-native, exogenous nucleic acid sequence encoding the polypeptide having an enzyme activity of EC 2.2.1.7 to metabolize the gas or feedstock and produce the hydrocarbon.

2. The method according to claim 1, wherein said hydrocarbon comprises one or more isoprene units as depicted in Formula I

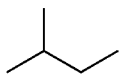
(I)

or a salt or derivative thereof.

3. The method according to claim 1, wherein said polypeptide having an enzyme activity of EC 2.2.1.7 converts glyceraldehyde-3-phosphate and pyruvate to 1 deoxy-d-xylulose-phosphate.

4. The method according to claim 1, wherein said polypeptide having an enzyme activity of EC 2.2.1.7:
   (i) is encoded by a nucleic acid sequence having at least 49% sequence identity to the nucleic acid sequence set forth in SEQ ID NO:4 or 5 or a functional fragment thereof;
   (ii) is encoded by a nucleic acid sequence comprising the nucleic acid sequence set forth in SEQ ID NO:4 or 5 or a functional fragment thereof;
   (iii) has at least 49% sequence identity to the amino acid sequence set forth in SEQ ID NO:1 or 2 or a functional fragment thereof; or
   (iv) comprises the amino acid sequence set forth in SEQ ID NO: 1 or 2 or a functional fragment thereof.

5. The method according to claim 1, wherein the recombinant host further comprises an exogenous nucleic acid sequence encoding a polypeptide having an enzyme activity of EC 4.2.3.27.

6. The method according to claim 5, wherein said polypeptide having an enzyme activity of EC 4.2.3.27 converts dimethylallylpyrophosphate to a hydrocarbon comprising one or more isoprene units as depicted in Formula I

(I)

or a salt or derivative thereof.

7. The method according to claim 5, wherein said polypeptide having an enzyme activity of EC 4.2.3.27 is:
   (i) encoded by a nucleic acid sequence having at least 70% sequence identity to the nucleic acid sequence set forth in SEQ ID NO: 6 or a functional fragment thereof;

(ii) encoded by a nucleic acid sequence comprising the nucleic acid sequence set forth in SEQ ID NO:6 or a functional fragment thereof;
(iii) an amino acid sequence having at least 70% sequence identity to the amino acid sequence set forth in SEQ ID NO:3 or a functional fragment thereof; or
(iv) an amino acid sequence comprising the amino acid sequence set forth in SEQ ID NO:3 or a functional fragment thereof.

8. The method according to claim 1 wherein the recombinant host is *Cupriavidus necator*.

9. The method according to claim 1 wherein the exogenous nucleic acid sequence encoding a polypeptide having an enzyme activity of EC 2.2.1.7 is codon optimized for *Cupriavidus necator*.

10. The method according to claim 1 wherein the host is transfected with a vector selected from SEQ ID NOs: 7, 8 or 9.

11. The method according to claim 1 wherein the fermentation reactor is operated under phosphate limiting conditions.

12. The method according to claim 1, wherein the feedstock comprises a biological feedstock comprising monosaccharides, disaccharides, lignocellulose, hemicellulose, cellulose, lignin, levulinic acid and formic acid, triglycerides, glycerol, fatty acids, agricultural waste, condensed distillers' solubles or municipal waste.

13. A method for synthesizing a hydrocarbon in a recombinant host consisting of a non-pathogenic member of the genera *Ralstonia, Wausteria, Cupriavidus, Alcaligenes, Burkholderia* or *Pandoraea* modified to comprise a non-native, exogenous nucleic acid sequence encoding a polypeptide having an enzyme activity of EC 2.2.1.7 which increases flux through a native metabolic 2-C-methyl-D-erythritol 4-phosphate (MEP) pathway of said host and a non-native, exogenous nucleic acid sequence encoding a polypeptide having an enzyme activity of EC 4.2.3.27, said method comprising
enzymatically converting glyceraldehyde-3-phosphate and pyruvate to 1 deoxy-d-xylulose-phosphate using the polypeptide having the enzyme activity of EC 2.2.1.7 encoded by the non-native, exogenous gene; and
enzymatically converting dimethylallylpyrophosphate to isoprene using the polypeptide having the enzyme activity of EC 4.2.3.27 encoded by the non-native, exogenous gene.

14. The method according to claim 13 wherein the hydrocarbon comprises one or more isoprene units as depicted in Formula I

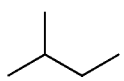

(I)

or a salt or derivative thereof.

15. The method according to claim 13 wherein the polypeptide having an enzyme activity of EC 2.2.1.7:
(i) is encoded by a nucleic acid sequence having at least 70% sequence identity to the nucleic acid sequence set forth in SEQ ID NO: 4 or SEQ ID NO:5 or a functional fragment thereof;
(ii) is encoded by a nucleic acid sequence comprising the nucleic acid sequence set forth in SEQ ID NO:4 or SEQ ID NO:5 or a functional fragment thereof;
(iii) has an amino acid sequence having at least 70% sequence identity to the amino acid sequence set forth in SEQ ID NO:1 or SEQ ID NO:2 or a functional fragment thereof; or
(iv) comprises an amino acid sequence comprising the amino acid sequence set forth in SEQ ID NO:1 or SEQ ID NO:2 or a functional fragment thereof.

16. The method according to claim 13, wherein said polypeptide having an enzyme activity of EC 4.2.3.27:
(i) is encoded by a nucleic acid sequence having at least 49% sequence identity to the nucleic acid sequence set forth in SEQ ID NO:6 or a functional fragment thereof;
(ii) is encoded by a nucleic acid sequence comprising the nucleic acid sequence set forth in SEQ ID NO:6 or a functional fragment thereof;
(iii) has at least 49% sequence identity to the amino acid sequence set forth in SEQ ID NO:3 or a functional fragment thereof; or
(iv) comprises the amino acid sequence set forth in SEQ ID NO: 3 or a functional fragment thereof.

17. The method according to claim 13 wherein the recombinant host is transfected with a vector selected from SEQ ID NOs: 7, 8 or 9.

18. The method of claim 1, further comprising recovering produced hydrocarbon.

19. The method of claim 18 wherein the hydrocarbon recovered is gaseous isoprene.

20. A recombinant host capable of producing a hydrocarbon via a methylerythritol phosphate (MEP) pathway, wherein said host is selected from non-pathogenic members of the genera *Ralstonia, Wausteria, Cupriavidus, Alcaligenes, Burkholderia* or *Pandoraea* and comprises a non-native exogenous nucleic acid sequence encoding a polypeptide having an enzyme activity of EC 2.2.1.7 which increases flux through a native metabolic MEP pathway of said host, and
wherein the host performs the enzymatic synthesis by gas fermentation of natural gas, methanol, ethanol, non-volatile residue, caustic wash from cyclohexane oxidation processes, or waste stream, or derivative thereof, optionally obtained from a chemical or petrochemical industry or on a biological or nonbiological feedstock.

21. The recombinant host of claim 20 further comprising an exogenous nucleic acid sequence encoding a polypeptide having an enzyme activity of EC 4.2.3.27.

22. The recombinant host according to claim 20 wherein the hydrocarbon comprises one or more isoprene units as depicted in Formula I

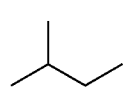

(I)

or a salt or derivative thereof.

23. The recombinant host according to claim 21, wherein said polypeptide having an enzyme activity of EC 4.2.3.27:
(i) is encoded by a nucleic acid sequence having at least 49% sequence identity to the nucleic acid sequence set forth in SEQ ID NO:6 or a functional fragment thereof;
(ii) is encoded by a nucleic acid sequence comprising the nucleic acid sequence set forth in SEQ ID NO:6 or a functional fragment thereof;
(iii) has at least 49% sequence identity to the amino acid sequence set forth in SEQ ID NO:3 or a functional fragment thereof; or (iv) comprises the amino acid sequence set forth in SEQ ID NO: 3 or a functional fragment thereof.

24. The recombinant host according to claim 20, wherein said polypeptide having an enzyme activity of EC 2.2.1.7 is:
    (i) encoded by a nucleic acid sequence having at least 70% sequence identity to the nucleic acid sequence set forth in SEQ ID NO: 4 or SEQ ID NO:5 or a functional fragment thereof;
    (ii) encoded by a nucleic acid sequence comprising the nucleic acid sequence set forth in SEQ ID NO:4 or SEQ ID NO:5 or a functional fragment thereof;
    (iii) an amino acid sequence having at least 70% sequence identity to the amino acid sequence set forth in SEQ ID NO:1 or SEQ ID NO:2 or a functional fragment thereof;
    (iv) an amino acid sequence comprising the amino acid sequence set forth in SEQ ID NO:1 or SEQ ID NO:2 or a functional fragment thereof.

25. The recombinant host according to claim 20 which is *Cupriavidus necator*.

26. The recombinant host according to claim 21, wherein at least one of the exogenous nucleic acid sequences is contained within a plasmid or is integrated into a chromosome of the host.

27. The recombinant host according to claim 20 transfected with a vector selected from SEQ ID NOs: 7, 8 or 9.

28. A method for producing a recombinant host capable of producing a hydrocarbon from a gas stream, said method comprising transfecting a host cell consisting of a non-pathogenic member of the genera *Ralstonia, Wausteria, Cupriavidus, Alcaligenes, Burkholderia* or *Pandoraea* with a non-native, exogenous nucleic acid sequence encoding a polypeptide having an enzyme activity of EC 2.2.1.7 which increases flux through a native metabolic MEP pathway of said host.

29. The method according to claim 28 further comprising transfecting the host with a non-native, exogenous nucleic acid sequence encoding a polypeptide having an enzyme activity of EC 4.2.3.27.

30. The method according to claim 28 wherein the hydrocarbon comprises one or more isoprene units as depicted in Formula I

(I)

or a salt or derivative thereof.

31. The method according to claim 28 wherein the host cell is *Cupriavidus* necator.

* * * * *

SEQUENCE LISTING

<160> NUMBER OF SEQ ID NOS: 32

<210> SEQ ID NO 1
<211> LENGTH: 620
<212> TYPE: PRT
<213> ORGANISM: E. coli

<400> SEQUENCE: 1

```
Met Ser Phe Asp Ile Ala Lys Tyr Pro Thr Leu Ala Leu Val Asp Ser
1               5                   10                  15

Thr Gln Glu Leu Arg Leu Leu Pro Lys Glu Ser Leu Pro Lys Leu Cys
            20                  25                  30

Asp Glu Leu Arg Arg Tyr Leu Leu Asp Ser Val Ser Arg Ser Ser Gly
        35                  40                  45

His Phe Ala Ser Gly Leu Gly Thr Val Glu Leu Thr Val Ala Leu His
    50                  55                  60

Tyr Val Tyr Asn Thr Pro Phe Asp Gln Leu Ile Trp Asp Val Gly His
65                  70                  75                  80

Gln Ala Tyr Pro His Lys Ile Leu Thr Gly Arg Arg Asp Lys Ile Gly
                85                  90                  95

Thr Ile Arg Gln Lys Gly Gly Leu His Pro Phe Pro Trp Arg Gly Glu
            100                 105                 110

Ser Glu Tyr Asp Val Leu Ser Val Gly His Ser Ser Thr Ser Ile Ser
        115                 120                 125

Ala Gly Ile Gly Ile Ala Val Ala Ala Glu Lys Glu Gly Lys Asn Arg
    130                 135                 140

Arg Thr Val Cys Val Ile Gly Asp Gly Ala Ile Thr Ala Gly Met Ala
145                 150                 155                 160

Phe Glu Ala Met Asn His Ala Gly Asp Ile Arg Pro Asp Met Leu Val
                165                 170                 175

Ile Leu Asn Asp Asn Glu Met Ser Ile Ser Glu Asn Val Gly Ala Leu
            180                 185                 190

Asn Asn His Leu Ala Gln Leu Leu Ser Gly Lys Leu Tyr Ser Ser Leu
        195                 200                 205

Arg Glu Gly Gly Lys Lys Val Phe Ser Gly Val Pro Pro Ile Lys Glu
    210                 215                 220

Leu Leu Lys Arg Thr Glu Glu His Ile Lys Gly Met Val Val Pro Gly
225                 230                 235                 240

Thr Leu Phe Glu Glu Leu Gly Phe Asn Tyr Ile Gly Pro Val Asp Gly
                245                 250                 255

His Asp Val Leu Gly Leu Ile Thr Thr Leu Lys Asn Met Arg Asp Leu
            260                 265                 270

Lys Gly Pro Gln Phe Leu His Ile Met Thr Lys Lys Gly Arg Gly Tyr
        275                 280                 285

Glu Pro Ala Glu Lys Asp Pro Ile Thr Phe His Ala Val Pro Lys Phe
    290                 295                 300

Asp Pro Ser Ser Gly Cys Leu Pro Lys Ser Ser Gly Gly Leu Pro Ser
305                 310                 315                 320

Tyr Ser Lys Ile Phe Gly Asp Trp Leu Cys Glu Thr Ala Ala Lys Asp
                325                 330                 335

Asn Lys Leu Met Ala Ile Thr Pro Ala Met Arg Glu Gly Ser Gly Met
            340                 345                 350

Val Glu Phe Ser Arg Lys Phe Pro Asp Arg Tyr Phe Asp Val Ala Ile
        355                 360                 365
```

```
Ala Glu Gln His Ala Val Thr Phe Ala Ala Gly Leu Ala Ile Gly Gly
    370                 375                 380

Tyr Lys Pro Ile Val Ala Ile Tyr Ser Thr Phe Leu Gln Arg Ala Tyr
385                 390                 395                 400

Asp Gln Val Leu His Asp Val Ala Ile Gln Lys Leu Pro Val Leu Phe
                405                 410                 415

Ala Ile Asp Arg Ala Gly Ile Val Gly Ala Asp Gly Gln Thr His Gln
            420                 425                 430

Gly Ala Phe Asp Leu Ser Tyr Leu Arg Cys Ile Pro Glu Met Val Ile
        435                 440                 445

Met Thr Pro Ser Asp Glu Asn Glu Cys Arg Gln Met Leu Tyr Thr Gly
    450                 455                 460

Tyr His Tyr Asn Asp Gly Pro Ser Ala Val Arg Tyr Pro Arg Gly Asn
465                 470                 475                 480

Ala Val Gly Val Glu Leu Thr Pro Leu Glu Lys Leu Pro Ile Gly Lys
                485                 490                 495

Gly Ile Val Lys Arg Arg Gly Glu Lys Leu Ala Ile Leu Asn Phe Gly
            500                 505                 510

Thr Leu Met Pro Glu Ala Ala Lys Val Ala Glu Ser Leu Asn Ala Thr
        515                 520                 525

Leu Val Asp Met Arg Phe Val Lys Pro Leu Asp Glu Ala Leu Ile Leu
    530                 535                 540

Glu Met Ala Ala Ser His Glu Ala Leu Val Thr Val Glu Glu Asn Ala
545                 550                 555                 560

Ile Met Gly Gly Ala Gly Ser Gly Val Asn Glu Val Leu Met Ala His
                565                 570                 575

Arg Lys Pro Val Pro Val Leu Asn Ile Gly Leu Pro Asp Phe Phe Ile
            580                 585                 590

Pro Gln Gly Thr Gln Glu Met Arg Ala Glu Leu Gly Leu Asp Ala
        595                 600                 605

Ala Gly Met Glu Ala Lys Ile Lys Ala Trp Leu Ala
    610                 615                 620

<210> SEQ ID NO 2
<211> LENGTH: 634
<212> TYPE: PRT
<213> ORGANISM: B. subtilis

<400> SEQUENCE: 2

Met Leu Asp Leu Leu Ser Ile Gln Asp Pro Ser Phe Leu Lys Asn Met
1               5                   10                  15

Ser Ile Asp Glu Leu Glu Lys Leu Ser Asp Glu Ile Arg Gln Phe Leu
                20                  25                  30

Ile Thr Ser Leu Ser Ala Ser Gly Gly His Ile Gly Pro Asn Leu Gly
            35                  40                  45

Val Val Glu Leu Thr Val Ala Leu His Lys Glu Phe Asn Ser Pro Lys
        50                  55                  60

Asp Lys Phe Leu Trp Asp Val Gly His Gln Ser Tyr Val His Lys Leu
65                  70                  75                  80

Leu Thr Gly Arg Gly Lys Glu Phe Ala Thr Leu Arg Gln Tyr Lys Gly
                85                  90                  95

Leu Cys Gly Phe Pro Lys Arg Ser Glu Ser Glu His Asp Val Trp Glu
            100                 105                 110

Thr Gly His Ser Ser Thr Ser Leu Ser Gly Ala Met Gly Met Ala Ala
        115                 120                 125
```

```
Ala Arg Asp Ile Lys Gly Thr Asp Glu Tyr Ile Ile Pro Ile Ile Gly
    130                 135                 140

Asp Gly Ala Leu Thr Gly Gly Met Ala Leu Glu Ala Leu Asn His Ile
145                 150                 155                 160

Gly Asp Glu Lys Lys Asp Met Ile Val Ile Leu Asn Asp Asn Glu Met
                165                 170                 175

Ser Ile Ala Pro Asn Val Gly Ala Ile His Ser Met Leu Gly Arg Leu
            180                 185                 190

Arg Thr Ala Gly Lys Tyr Gln Trp Val Lys Asp Glu Leu Glu Tyr Leu
        195                 200                 205

Phe Lys Lys Ile Pro Ala Val Gly Gly Lys Leu Ala Ala Thr Ala Glu
    210                 215                 220

Arg Val Lys Asp Ser Leu Lys Tyr Met Leu Val Ser Gly Met Phe Phe
225                 230                 235                 240

Glu Glu Leu Gly Phe Thr Tyr Leu Gly Pro Val Asp Gly His Ser Tyr
                245                 250                 255

His Glu Leu Ile Glu Asn Leu Gln Tyr Ala Lys Lys Thr Lys Gly Pro
            260                 265                 270

Val Leu Leu His Val Ile Thr Lys Lys Gly Lys Gly Tyr Lys Pro Ala
        275                 280                 285

Glu Thr Asp Thr Ile Gly Thr Trp His Gly Thr Gly Pro Tyr Lys Ile
    290                 295                 300

Asn Thr Gly Asp Phe Val Lys Pro Lys Ala Ala Ala Pro Ser Trp Ser
305                 310                 315                 320

Gly Leu Val Ser Gly Thr Val Gln Arg Met Ala Arg Glu Asp Gly Arg
                325                 330                 335

Ile Val Ala Ile Thr Pro Ala Met Pro Val Gly Ser Lys Leu Glu Gly
            340                 345                 350

Phe Ala Lys Glu Phe Pro Asp Arg Met Phe Asp Val Gly Ile Ala Glu
        355                 360                 365

Gln His Ala Ala Thr Met Ala Ala Met Ala Met Gln Gly Met Lys
    370                 375                 380

Pro Phe Leu Ala Ile Tyr Ser Thr Phe Leu Gln Arg Ala Tyr Asp Gln
385                 390                 395                 400

Val Val His Asp Ile Cys Arg Gln Asn Ala Asn Val Phe Ile Gly Ile
                405                 410                 415

Asp Arg Ala Gly Leu Val Gly Ala Asp Gly Glu Thr His Gln Gly Val
            420                 425                 430

Phe Asp Ile Ala Phe Met Arg His Ile Pro Asn Met Val Leu Met Met
        435                 440                 445

Pro Lys Asp Glu Asn Glu Gly Gln His Met Val His Thr Ala Leu Ser
    450                 455                 460

Tyr Asp Glu Gly Pro Ile Ala Met Arg Phe Pro Arg Gly Asn Gly Leu
465                 470                 475                 480

Gly Val Lys Met Asp Glu Gln Leu Lys Thr Ile Pro Ile Gly Thr Trp
                485                 490                 495

Glu Val Leu Arg Pro Gly Asn Asp Ala Val Ile Leu Thr Phe Gly Thr
            500                 505                 510

Thr Ile Glu Met Ala Ile Glu Ala Ala Glu Leu Gln Lys Glu Gly
        515                 520                 525

Leu Ser Val Arg Val Val Asn Ala Arg Phe Ile Lys Pro Ile Asp Glu
530                 535                 540
```

```
Lys Met Met Lys Ser Ile Leu Lys Glu Gly Leu Pro Ile Leu Thr Ile
545                 550                 555                 560

Glu Glu Ala Val Leu Glu Gly Gly Phe Gly Ser Ser Ile Leu Glu Phe
                565                 570                 575

Ala His Asp Gln Gly Glu Tyr His Thr Pro Ile Asp Arg Met Gly Ile
            580                 585                 590

Pro Asp Arg Phe Ile Glu His Gly Ser Val Thr Ala Leu Leu Glu Glu
595                 600                 605

Ile Gly Leu Thr Lys Gln Gln Val Ala Asn Arg Ile Arg Leu Leu Met
610                 615                 620

Pro Pro Lys Thr His Lys Gly Ile Gly Ser
625                 630

<210> SEQ ID NO 3
<211> LENGTH: 560
<212> TYPE: PRT
<213> ORGANISM: Populus alba

<400> SEQUENCE: 3

Met Arg Cys Ser Val Ser Thr Glu Asn Val Ser Phe Thr Glu Thr Glu
1               5                   10                  15

Thr Glu Ala Arg Arg Ser Ala Asn Tyr Glu Pro Asn Ser Trp Asp Tyr
                20                  25                  30

Asp Tyr Leu Leu Ser Ser Asp Thr Asp Glu Ser Ile Glu Val Tyr Lys
            35                  40                  45

Asp Lys Ala Lys Lys Leu Glu Ala Glu Val Arg Arg Glu Ile Asn Asn
        50                  55                  60

Glu Lys Ala Glu Phe Leu Thr Leu Leu Glu Leu Ile Asp Asn Val Gln
65                  70                  75                  80

Arg Leu Gly Leu Gly Tyr Arg Phe Glu Ser Asp Ile Arg Gly Ala Leu
                85                  90                  95

Asp Arg Phe Val Ser Ser Gly Gly Phe Asp Ala Val Thr Lys Thr Ser
            100                 105                 110

Leu His Gly Thr Ala Leu Ser Phe Arg Leu Leu Arg Gln His Gly Phe
        115                 120                 125

Glu Val Ser Gln Glu Ala Phe Ser Gly Phe Lys Asp Gln Asn Gly Asn
130                 135                 140

Phe Leu Glu Asn Leu Lys Glu Asp Ile Lys Ala Ile Leu Ser Leu Tyr
145                 150                 155                 160

Glu Ala Ser Phe Leu Ala Leu Glu Gly Glu Asn Ile Leu Asp Glu Ala
                165                 170                 175

Lys Val Phe Ala Ile Ser His Leu Lys Glu Leu Ser Glu Glu Lys Ile
            180                 185                 190

Gly Lys Glu Leu Ala Glu Gln Val Asn His Ala Leu Glu Leu Pro Leu
        195                 200                 205

His Arg Arg Thr Gln Arg Leu Glu Ala Val Trp Ser Ile Glu Ala Tyr
210                 215                 220

Arg Lys Lys Glu Asp Ala Asn Gln Val Leu Leu Glu Leu Ala Ile Leu
225                 230                 235                 240

Asp Tyr Asn Met Ile Gln Ser Val Tyr Gln Arg Asp Leu Arg Glu Thr
                245                 250                 255

Ser Arg Trp Trp Arg Arg Val Gly Leu Ala Thr Lys Leu His Phe Ala
            260                 265                 270

Arg Asp Arg Leu Ile Glu Ser Phe Tyr Trp Ala Val Gly Val Ala Phe
        275                 280                 285
```

```
Glu Pro Gln Tyr Ser Asp Cys Arg Asn Ser Val Ala Lys Met Phe Ser
    290                 295                 300
Phe Val Thr Ile Ile Asp Ile Tyr Asp Val Tyr Gly Thr Leu Asp
305                 310                 315                 320
Glu Leu Glu Leu Phe Thr Asp Ala Val Glu Arg Trp Asp Val Asn Ala
                325                 330                 335
Ile Asn Asp Leu Pro Asp Tyr Met Lys Leu Cys Phe Leu Ala Leu Tyr
                340                 345                 350
Asn Thr Ile Asn Glu Ile Ala Tyr Asp Asn Leu Lys Asp Lys Gly Glu
                355                 360                 365
Asn Ile Leu Pro Tyr Leu Thr Lys Ala Trp Ala Asp Leu Cys Asn Ala
                370                 375                 380
Phe Leu Gln Glu Ala Lys Trp Leu Tyr Asn Lys Ser Thr Pro Thr Phe
385                 390                 395                 400
Asp Asp Tyr Phe Gly Asn Ala Trp Lys Ser Ser Gly Pro Leu Gln
                405                 410                 415
Leu Val Phe Ala Tyr Phe Ala Val Val Gln Asn Ile Lys Lys Glu Glu
                420                 425                 430
Ile Glu Asn Leu Gln Lys Tyr His Asp Thr Ile Ser Arg Pro Ser His
                435                 440                 445
Ile Phe Arg Leu Cys Asn Asp Leu Ala Ser Ala Ser Ala Glu Ile Ala
                450                 455                 460
Arg Gly Glu Thr Ala Asn Ser Val Ser Cys Tyr Met Arg Thr Lys Gly
465                 470                 475                 480
Ile Ser Glu Glu Leu Ala Thr Glu Ser Val Met Asn Leu Ile Asp Glu
                485                 490                 495
Thr Trp Lys Lys Met Asn Lys Gly Lys Leu Gly Gly Ser Leu Phe Ala
                500                 505                 510
Lys Pro Phe Val Glu Thr Ala Ile Asn Leu Ala Arg Gln Ser His Cys
                515                 520                 525
Thr Tyr His Asn Gly Asp Ala His Thr Ser Pro Asp Glu Leu Thr Arg
                530                 535                 540
Lys Arg Val Leu Ser Val Ile Thr Glu Pro Ile Leu Pro Phe Glu Arg
545                 550                 555                 560

<210> SEQ ID NO 4
<211> LENGTH: 1863
<212> TYPE: DNA
<213> ORGANISM: E. coli

<400> SEQUENCE: 4
atgagttttg atattgccaa atacccgacc ctggcactgg tcgactccac ccaggagtta      60
cgactgttgc cgaaagagag tttaccgaaa ctctgcgacg aactgcgccg ctatttactc     120
gacagcgtga ccgttccag cgggcacttc gcctccgggc tggcacggt cgaactgacc      180
gtggcgctgc actatgtcta caacacccg tttgaccaat tgatttggga tgtgggcat      240
caggcttatc gcataaaaat tttgaccgga cgccgcgaca aaatcggcac atccgtcag     300
aaaggcggtc tgcacccgtt cccgtggcgc ggcgaaagcg aatatgacgt attaagcgtc     360
gggcattcat caacctccat cagtgccgga attggtattg cggttgctgc gaaaaagaa     420
ggcaaaaatc gccgcaccgt ctgtgtcatt ggcgatggcg cgattaccgc aggcatggcg     480
tttgaagcga tgaatcacgc gggcgatatc cgtcctgata tgctggtgat tctcaacgac     540
aatgaaatgt cgatttccga aaatgtcggc gcgctcaaca accatctggc acagctgctt     600
```

-continued

```
tccggtaagc tttactcttc actgcgcgaa ggcgggaaaa aagtttctc tggcgtgccg      660 ccaattaaag agctgctcaa acgcaccgaa gaacatatta aaggcatggt agtgcctggc     720
acgttgtttg aagagctggg cttaactac atcggcccgg tggacggtca cgatgtgctg     780
gggcttatca ccacgctaaa gaacatgcgc gacctgaaag ccccgcagtt cctgcatatc    840
atgaccaaaa aaggtcgtgg ttatgaaccg gcagaaaaag acccgatcac tttccacgcc    900
gtgcctaaat ttgatccctc cagcggttgt ttgccgaaaa gtagcggcgg tttgccgagc    960
tattcaaaaa tctttggcga ctggttgtgc gaaacggcag cgaaagacaa caagctgatg   1020
gcgattactc cggcgatgcg tgaaggttcc ggcatggtcg agttttcacg taaattcccg   1080
gatcgctact tcgacgtggc aattgccgag caacacgcgg tgacctttgc tgcgggtctg   1140
gcgattggtg ggtacaaacc cattgtcgcg atttactcca ctttcctgca acgcgcctat   1200
gatcaggtgc tgcatgacgt ggcgattcaa aagcttccgg tcctgttcgc catcgaccgc   1260
gcgggcattg ttggtgctga cggtcaaacc catcagggtg cttttgatct ctcttacctg   1320
cgctgcatac cggaaatggt cattatgacc ccgagcgatg aaaacgaatg tcgccagatg   1380
ctctataccg gctatcacta taacgatggc cgtcagcgg tgcgctaccc gcgtggcaac    1440
gcggtcggcg tggaactgac gccgctggaa aaactaccaa ttggcaaagg cattgtgaag   1500
cgtcgtggcg agaaactggc gatccttaac tttggtacgc tgatgccaga agcggcgaaa   1560
gtcgccgaat cgctgaacgc cacgctggtc gatatgcgtt ttgtgaaacc gcttgatgaa   1620
gcgttaattc tggaaatggc cgccagccat gaagcgctgg tcaccgtaga agaaaacgcc   1680
attatgggcg gcgcaggcag cggcgtgaac gaagtgctga tggcccatcg taaaccagta   1740
cccgtgctga acattggcct gccggacttc tttattccgc aaggaactca ggaagaaatg   1800
cgcgccgaac tcggcctcga tgccgctggt atggaagcca aaatcaaggc ctggctggca   1860
taa                                                                   1863
```

<210> SEQ ID NO 5
<211> LENGTH: 1905
<212> TYPE: DNA
<213> ORGANISM: B. subtilis

<400> SEQUENCE: 5

```
atgctggatc tgctgtcgat ccaggacccg tccttcctga gaacatgag catcgacgag      60 ctggagaagc tgtccgacga gatccgccag ttcctgatca cctcgctcag cgcctcgggc   120
ggccatatcg gccccaacct gggcgtcgtg gaactgacgg tggccctgca caaggaattc   180
aactcgccga aggacaagtt cctgtgggat gtgggccatc agtcgtatgt ccacaagctg   240
ctgaccggcc gcgcaagga attgccacg ctgcgccaat acaagggcct gtgcggcttt     300
ccgaagcgct cggaatcgga acatgacgtc tgggaaacgg ccacagctc gaccagcctg    360 agcggcgcca tgggtatggc ggccgcccgc gacatcaagg gcacgacga gtatatcatc    420 ccgatcatcg gcgacggcgc cctgacgggc ggcatggcgc tcgaagccct caaccacatc    480
ggtgatgaga agaaggacat gatcgtgatc ctgaacgaca acgaaatgag catcgcgccg    540
aatgtgggcg ccattcattc gatgctggc cgcctgcgta ccgcgggtaa gtatcagtgg     600
gtgaaggatg agctggagta cctgttcaag aagatcccgg cggtgggcgg caagctggcc    660 gccacggcg agcgcgtgaa ggactccctg aagtacatgc tcgtcagcgg catgtttttc    720
gaggaactgg gcttcaccta tctgggcccg gtggatggcc actcctacca tgagctcatc     780
```

-continued

| | |
|---|---|
| gaaaatctgc aatacgccaa aaagacgaag ggccccgtcc tcctccacgt catcacgaag | 840 |
| aagggcaagg gctacaagcc cgccgaaacc gacaccatcg gcacgtggca tggcaccggc | 900 |
| ccctacaaga tcaacacggg cgactttgtg aagccgaagg ccgccgcgcc gtcctggagc | 960 |
| ggcctggtga gcggcaccgt ccagcgtatg gcccgcgaag atggccggat cgtggcgatc | 1020 |
| accccggcga tgccggtcgg cagcaagctg gaaggcttcg ccaaggaatt cccggaccgc | 1080 |
| atgttcgacg tgggcatcgc ggagcagcac gccgccacga tggcggcggc catggccatg | 1140 |
| cagggtatga agccgttcct ggcgatctac tccacgttcc tgcagcgcgc ctacgaccag | 1200 |
| gtcgtgcacg atatctgccg ccagaatgcg aatgtgttca tcggcatcga ccgcgcgggc | 1260 |
| ctggtgggcg cggacggcga aacccaccag ggcgtgttcg atatcgcgtt tatgcgtcac | 1320 |
| atcccgaaca tggtcctgat gatgccgaag gatgagaacg aaggccagca catggtccat | 1380 |
| accgccctga gctatgatga aggcccgatc gccatgcgct tccccgtgg taacggcctg | 1440 |
| ggtgtgaaga tggacgagca gctcaagacc atcccgattg gcacctggga agtgctgcgc | 1500 |
| ccgggtaatg acgcggtgat cctgaccttc ggcacgacca tcgagatggc catcgaagcg | 1560 |
| gccgaggaac tgcagaagga aggcctgtcg gtgcgcgtcg tcaacgcccg cttcattaag | 1620 |
| ccgatcgacg agaagatgat gaagtcgatc ctgaaggagg gcctgcccat cctgaccatc | 1680 |
| gaagaagccg tgctggaggg cggcttcggt tcgtcgatcc tggaattcgc gcacgaccag | 1740 |
| ggcgagtacc acacgccgat cgaccgcatg ggcatcccgg accggttcat cgagcacggc | 1800 |
| tcggtcaccg ccctgctgga agaaattggc ctcaccaagc aacaagtggc caaccggatt | 1860 |
| cggctcctga tgccccccaa gacccacaag ggcatcggct cgtga | 1905 |

<210> SEQ ID NO 6
<211> LENGTH: 1881
<212> TYPE: DNA
<213> ORGANISM: Populus alba

<400> SEQUENCE: 6

| | |
|---|---|
| ataggatcct aatacgactc actatagggt tttgtttaac tttaagaagg agatatacca | 60 |
| tggctactga actgctgtgt ttgcatcgcc cgatttcact tacacataaa ctgtttcgca | 120 |
| atccactgcc gaaggttatt caggcgaccc ctctgacgtt aaaactgcgt tgtagcgtta | 180 |
| gcaccgaaaa tgtgtcgttt acggaaacgg aaaccgaagc tcgccgcagc gcaaactatg | 240 |
| aaccgaactc gtgggattac gattacctcc ttagcagcga tacggatgaa agcattgaag | 300 |
| tgtataaaga caaagccaag aaactggagg ccgaagtccg tcgcgaaatc aacaatgaga | 360 |
| aagcggagtt tcttacgtta ctggaattga tcgataacgt gcaacggtta ggcctcggct | 420 |
| accgctttga gagcgatatc cgtggtgcac tggaccgctt cgtatcgtct ggtggttttg | 480 |
| acgccgttac gaaaacgagc ctgcatggta cagcattgtc ttttcggctg ttgcgccagc | 540 |
| atggatttga agtgtcacag gaggcatttt caggcttcaa agaccagaac gggaattttt | 600 |
| tggagaattt gaaagaagat atcaaagcga tcttatctct gtatgaggcg tcatttctcg | 660 |
| ctctggaagg ggaaaatatt ctggacgaag cgaaagtgtt cgcaatttcc catctgaaag | 720 |
| aactttccga agaaaagatt gggaaagaat tggccgaaca ggtgaaccat gcgctggaac | 780 |
| tgccactgca ccgtcgcacc caacgcctcg aagcggtatg gtcgattgaa gcgtatcgca | 840 |
| aaaaagagga tgcaaatcag gttctgctgg aactggccat tctcgactat aacatgattc | 900 |
| agtccgtcta tcaacgtgat ctgcgcgaaa ctagtcgttg gtggcgccgt gtaggacttg | 960 |
| ccactaaact gcattttgca cgtgatcgtc tgattgagtc gttctattgg gcggttggtg | 1020 |

```
tagcgtttga gccgcagtat tctgattgcc gcaatagtgt ggcgaaaatg ttctcctttg    1080
tgaccatcat tgacgatatt tacgacgtgt atggcaccct ggatgaactg gaattattca    1140
ccgatgcagt agaacgctgg gacgtcaacg cgatcaatga tttgccggat tacatgaaac    1200
tgtgttttct ggccctgtat aacaccatta acgaaattgc ctatgacaac ctcaaagaca    1260
agggtgaaaa tatcctgccc tatctgacta agcttgggc tgatctgtgt aacgcgttct    1320
tacaggaagc caaatggctc tacaacaaga gtacgcctac tttcgatgac tactttggca    1380
acgcttggaa aagctctagc ggccctttac aactggtgtt cgcgtatttc gccgttgttc    1440
agaatatcaa gaaagaagag attgagaacc tccaaaagta ccacgatacg atttcgcgtc    1500
cgtcacacat ctttcgcctt tgcaatgatt tggccagtgc atctgcagag attgcgcgcg    1560
gtgaaactgc caactccgtc agttgctaca tgcgtaccaa aggcatcagc gaggaactgg    1620
ctaccgagtc ggtgatgaac ttaatcgatg aaacctggaa gaagatgaac aaagagaaac    1680
ttggtggcag tctgtttgct aaaccgttcg ttgagacagc gattaatctg gcgcgtcaaa    1740
gccactgcac ctaccacaat ggcgatgccc acacatcccc agacgaatta acccggaaac    1800
gtgtcctgag tgtcatcacc gaacccattc tgccgttcga acgccatcat caccatcacc    1860
attaatagcc tagggtgtta a                                              1881
```

<210> SEQ ID NO 7
<211> LENGTH: 7399
<212> TYPE: DNA
<213> ORGANISM: artificial sequence
<220> FEATURE:
<223> OTHER INFORMATION: Synthetic

<400> SEQUENCE: 7

```
tagattaatt aacctccagc gcggggatct catgctggag ttcttcgccc accccccagac    60 aagctgtgac cgtctccggg agctgcatgt gtcagaggtt ttcaccgtca tcaccgaaac    120
gcgcgaggca gcagatcaat tcgcgcgcga aggcgaagcg gcatgcataa tgtgcctgtc    180
aaatggacga agcagggatt ctgcaaaccc tatgctactc cgtcaagccg tcaattgtct    240
gattcgttac caattatgac aacttgacgg ctacatcatt cacttttct tcacaaccgg    300 cacggaactc gctcgggctg gccccggtgc attttttaaa tacccgcgag aaatagagtt    360
gatcgtcaaa accaacattg cgaccgacgg tggcgatagg catccgggtg gtgctcaaaa    420
gcagcttcgc ctggctgata cgttggtcct cgcgccagct taagacgcta atccctaact    480
gctggcggaa aagatgtgac agacgcgacg gcgacaagca acatgctgt gcgacgctgg    540 cgatatcaaa attgctgtct gccaggtgat cgctgatgta ctgacaagcc tcgcgtaccc    600
gattatccat cggtggatgg agcgactcgt taatcgcttc catgcgccgc agtaacaatt    660
gctcaagcag atttatcgcc agcagctccg aatagcgccc ttcccttgc ccggcgttaa    720 tgattgccc aaacaggtcg ctgaaatgcg gctggtgcgc ttcatccggg cgaaagaacc    780
ccgtattggc aaatattgac ggccagttaa gccattcatg ccagtaggcg cgcggacgaa    840
agtaaaccca ctggtgatac cattcgcgag cctccggatg acgaccgtag tgatgaatct    900
ctcctggcgg gaacagcaaa atatcacccg gtcggcaaac aaattctcgt ccctgatttt    960
tcaccacccc ctgaccgcga atggtgagat tgagaatata acctttcatt cccagcggtc    1020
ggtcgataaa aaaatcgaga taaccgttgg cctcaatcgg cgttaaaccc gccaccagat    1080
gggcattaaa cgagtatccc ggcagcaggg gatcattttg cgcttcagcc atacttttca    1140
```

```
tactcccgcc attcagagaa gaaaccaatt gtccatattg catcagacat tgccgtcact   1200
gcgtctttta ctggctcttc tcgctaacca aaccggtaac cccgcttatt aaaagcattc   1260
tgtaacaaag cgggaccaaa gccatgacaa aaacgcgtaa caaaagtgtc tataatcacg   1320
gcagaaaagt ccacattgat tatttgcacg gcgtcacact ttgctatgcc atagcatttt   1380
tatccataag attagcggat cctacctgac gctttttatc gcaactctct actgtttctc   1440
catacccgtt ttttgggcta gaaataattt tgagctcctt taaggaagga gcgaagcatg   1500
cgttgtagcg ttagcaccga aaatgtgtcg tttacggaaa cggaaaccga agctcgccgc   1560
agcgcaaact atgaaccgaa ctcgtgggat tacgattacc tccttagcag cgatacggat   1620
gaaagcattg aagtgtataa agacaaagcc aagaaactgg aggccgaagt ccgtcgcgaa   1680
atcaacaatg agaaagcgga gtttcttacg ttactggaat tgatcgataa cgtgcaacgg   1740
ttaggcctcg gctaccgctt tgagagcgat atccgtggtg cactggaccg cttcgtatcg   1800
tctggtggtt ttgacgccgt tacgaaaacg agcctgcatg gtacagcatt gtcttttcgg   1860
ctgttgcgcc agcatggatt tgaagtgtca caggaggcat tttcaggctt caaagaccag   1920
aacgggaatt ttttggagaa tttgaaagaa gatatcaaag cgatcttatc tctgtatgag   1980
gcgtcatttc tcgctctgga aggggaaaat attctggacg aagcgaaagt gttcgcaatt   2040
tcccatctga aagaactttc cgaagaaaag attgggaaag aattggccga acaggtgaac   2100
catgcgctgg aactgccact gcaccgtcgc acccaacgcc tcgaagcggt atggtcgatt   2160
gaagcgtatc gcaaaaaaga ggatgcaaat caggttctgc tggaactggc cattctcgac   2220
tataacatga ttcagtccgt ctatcaacgt gatctgcgcg aaactagtcg ttggtggcgc   2280
cgtgtaggac ttgccactaa actgcatttt gcacgtgatc gtctgattga gtcgttctat   2340
tgggcggttg gtgtagcgtt tgagccgcag tattctgatt gccgcaatag tgtggcgaaa   2400
atgttctcct ttgtgaccat cattgacgat atttacgacg tgtatggcac cctggatgaa   2460
ctggaattat tcaccgatgc agtagaacgc tgggacgtca acgcgatcaa tgatttgccg   2520
gattacatga aactgtgttt tctggccctg tataacacca ttaacgaaat tgcctatgac   2580
aacctcaaag acaagggtga aaatatcctg ccctatctga ctaaagcttg gctgatctg   2640
tgtaacgcgt tcttacagga agccaaatgg ctctacaaca agagtacgcc tactttcgat   2700
gactactttg gcaacgcttg gaaaagctct agcggcccctt tacaactggt gttcgcgtat   2760
ttcgccgttg ttcagaatat caagaaagaa gagattgaga acctccaaaa gtaccacgat   2820
acgatttcgc gtccgtcaca catctttcgc ctttgcaatg atttggccag tgcatctgca   2880
gagattgcgc gcggtgaaac tgccaactcc gtcagttgct acatgcgtac caaaggcatc   2940
agcgaggaac tggctaccga gtcggtgatg aacttaatcg atgaaacctg gaagaagatg   3000
aacaaagaga acttggtgg cagtctgttt gctaaaccgt tcgttgagac agcgattaat   3060
ctggcgcgtc aaagccactg cacctaccac aatggcgatg cccacacatc cccagacgaa   3120
ttaacccgga aacgtgtcct gagtgtcatc accgaaccca ttctgccgtt cgaacgctaa   3180
gcctgctaac aaagcccgaa aggaagctga gttggctgct gccaccgctg agcactagtg   3240
cggccgcttt gcgcattcac agttctccgc aagaattgat tggctccaat tcttggagtg   3300
gtgaatccgt tagcgaggtg ccgccggctt ccattcaggt cgaggtggcc cggctccatg   3360
caccgcgacg caacgcgggg aggcagacaa ggtataggc ggcgcctaca atccatgcca   3420
acccgttcca tgtgctcgcc gaggcggcat aaatcgccgt gacgatcagc ggtccagtga   3480
tcgaagttag gctggtaaga gccgcgagcg atccttgaag ctgtccctga tggtcgtcat   3540
```

```
ctacctgcct ggacagcatg gcctgcaacg cgggcatccc gatgccgccg gaagcgagaa      3600
gaatcataat ggggaaggcc atccagcctc gcgtcgcgaa cgccagcaag acgtagccca      3660
gcgcgtcggc cgccatgccg gcgataatgg cctgcttctc gccgaaacgt ttggtggcgg      3720
gaccagtgac gaaggcttga gcgagggcgt gcaagattcc gaataccgca agcgacaggc      3780
cgatcatcgt cgcgctccag cgaaagcggt cctcgccgaa aatgacccag agcgctgccg      3840
gcacctgtcc tacgagttgc atgataaaga agacagtcat aagtgcgcg acgatagtca       3900 tgccccgcgc ccaccggaag gagctgactg ggttgaaggc tctcaagggc atcggtcgac      3960
gctctccctt atgcgactcc tgcattagga agcagcccag tagtaggttg aggccgttga      4020
gcaccgccgc cgcaaggaat ggtgcatgca aggagatggc gcccaacagt cccccggcca      4080
cggggcctgc caccatacec acgccgaaac aagcgctcat gagcccgaag tggcgagccc      4140
gatcttcccc atcggtgatg tcggcgatat aggcgccagc aaccgcacct gtggcgccgg      4200
tgatgccggc cacgatgcgt ccggcgtaga ggatccacag gacgggtgtg gtcgccatga      4260
tcgcgtagtc gatagtggct ccaagtagcg aagcgagcag gactgggcgg cggccaaagc      4320
ggtcggacag tgctccgaga acgggtgcgc atagaaattg catcaacgca tatagcgcta      4380
gcagcacgcc atagtgactg gcgatgctgt cggaatggac gatatcccgc aagaggcccg      4440
gcagtaccgg cataaccaag cctatgccta cagcatccag ggtgacggtg ccgaggatga      4500
cgatgagcgc attgttagat ttcatacacg gtgcctgact gcgttagcaa tttaactgtg      4560
ataaactacc gcattaaagc ttatcgatga taagctgtca aacatgagaa ttcttgaaga      4620
cgaaagggcc tcgtgatacg cctatttta taggttaatg tcatgataat aatggtttct      4680
tagacgtcag gtggcacttt tcggggaaat gtgcgcgccc gcgttcctgc tggcgctggg      4740
cctgtttctg gcgctggact tcccgctgtt ccgtcagcag cttttcgccc acggccttga      4800
tgatcgcggc ggccttggcc tgcatatccc gattcaacgg ccccagggcg tccagaacgg      4860
gcttcaggcg ctcccgaagg tctcgggccg tctcttgggc ttgatcggcc ttcttgcgca      4920
tctcacgcgc tcctgcggcg gcctgtaggg caggctcata cccctgccga accgcttttg      4980
tcagccggtc ggccacggct tccggcgtct caacgcgctt tgagattccc agcttttcgg      5040
ccaatccctg cggtgcatag gcgcgtggct cgaccgcttg cgggctgatg gtgacgtggc      5100
ccactggtgg ccgctccagg gcctcgtaga acgcctgaat gcgcgtgtga cgtgccttgc      5160
tgccctcgat gccccgttgc agccctagat cggccacagc ggccgcaaac gtggtctggt      5220
cgcgggtcat ctgcgctttg ttgccgatga actccttggc cgacagcctg ccgtcctgcg      5280
tcagcggcac cacgaacgcg gtcatgtgcg ggctggtttc gtcacggtgg atgctggccg      5340
tcacgatgcg atccgccccg tacttgtccg ccagccactt gtgcgccttc tcgaagaacg      5400
ccgcctgctg ttcttggctg gccgacttcc accattccgg gctggccgtc atgacgtact      5460
cgaccgccaa cacagcgtcc ttgcgccgct tctctggcag caactcgcgc agtcggccca      5520
tcgcttcatc ggtgctgctg gccgcccagt gctcgttctc tggcgtcctg ctggcgtcag      5580
cgttgggcgt ctcgcgctcg cggtaggcgt gcttgagact ggccgccacg ttgcccattt      5640
tcgccagctt cttgcatcgc atgatcgcgt atgccgccat gcctgcccct cccttttggt      5700
gtccaaccgg ctcgacgggg gcagcgcaag gcggtgcctc cggcgggcca ctcaatgctt      5760
gagtatactc actagacttt gcttcgcaaa gtcgtgaccg cctacggcgg ctgcggcgcc      5820
ctacgggctt gctctccggg cttcgccctg cgcggtcgct gcgctccctt gccagcccgt      5880
```

-continued

| | |
|---|---|
| ggatatgtgg acgatggccg cgagcggcca ccggctggct cgcttcgctc ggcccgtgga | 5940 |
| caaccctgct ggacaagctg atggacaggc tgcgcctgcc cacgagcttg accacaggga | 6000 |
| ttgcccaccg gctacccagc cttcgaccac atacccaccg gctccaactg cgcggcctgc | 6060 |
| ggccttgccc catcaatttt tttaattttc tctggggaaa agcctccggc ctgcggcctg | 6120 |
| cgcgcttcgc ttgccggttg acaccaagt ggaaggcggg tcaaggctcg cgcagcgacc | 6180 |
| gcgcagcggc ttggccttga cgcgcctgga acgacccaag cctatgcgag tgggggcagt | 6240 |
| cgaagggcga agcccgcccg cctgcccccc gagcctcacg gcggcgagtg cgggggttcc | 6300 |
| aaggggcag cgccaccttg ggcaaggccg aaggccgcgc agtcgatcaa caagcccgg | 6360 |
| aggggccact ttttgccgga gggggagccg cgccgaaggc gtgggggaac cccgcagggg | 6420 |
| tgcccttctt tgggcaccaa agaactagat ataggggcgaa atgcgaaaga cttaaaaatc | 6480 |
| aacaacttaa aaaggggggg tacgcaacag ctcattgcgg caccccccgc aatagctcat | 6540 |
| tgcgtaggtt aaagaaaatc tgtaattgac tgccacttttt acgcaacgca taattgttgt | 6600 |
| cgcgctgccg aaaagttgca gctgattgcg catggtgccg caaccgtgcg gcaccccctac | 6660 |
| cgcatggaga taagcatggc cacgcagtcc agagaaatcg gcattcaagc caagaacaag | 6720 |
| cccggtcact gggtgcaaac ggaacgcaaa gcgcatgagg cgtgggccgg gcttattgcg | 6780 |
| aggaaaccca cggcggcaat gctgctgcat cacctcgtgg cgcagatggg ccaccagaac | 6840 |
| gccgtggtgg tcagccagaa gacactttcc aagctcatcg gacgttcttt gcggacggtc | 6900 |
| caatacgcag tcaaggactt ggtggccgag cgctggatct ccgtcgtgaa gctcaacggc | 6960 |
| cccggcaccg tgtcggccta cgtggtcaat gaccgcgtgg cgtggggcca gccccgcgac | 7020 |
| cagttgcgcc tgtcggtgtt cagtgccgcc gtggtggttg atcacgacga ccaggacgaa | 7080 |
| tcgctgttgg ggcatggcga cctgcgccgc atcccgaccc tgtatccggg cgagcagcaa | 7140 |
| ctaccgaccg gccccggcga ggagccgccc agccagcccg gcattccggg catggaacca | 7200 |
| gacctgccag ccttgaccga aacggaggaa tgggaacggc gcgggcagca gcgcctgccg | 7260 |
| atgcccgatg agccgtgttt tctggacgat ggcgagccgt tggagccgcc gacacgggtc | 7320 |
| acgctgccgc gccggtagca cttgggttgc gcagcaaccc gtaagtgcgc tgttccagac | 7380 |
| tatcggctgt agccgcctc | 7399 |

<210> SEQ ID NO 8
<211> LENGTH: 9320
<212> TYPE: DNA
<213> ORGANISM: artificial sequence
<220> FEATURE:
<223> OTHER INFORMATION: Synthetic

<400> SEQUENCE: 8

| | |
|---|---|
| ctcgatgccc cgttgcagcc ctagatcggc cacagcggcc gcaaacgtgg tctggtcgcg | 60 |
| ggtcatctgc gctttgttgc cgatgaactc cttggccgac agcctgccgt cctgcgtcag | 120 |
| cggcaccacg aacgcggtca tgtgcgggct ggtttcgtca cggtggatgc tggccgtcac | 180 |
| gatgcgatcc gccccgtact tgtccgccag ccacttgtgc gccttctcga agaacgccgc | 240 |
| ctgctgttct tggctggccg acttccacca ttccgggctg gccgtcatga cgtactcgac | 300 |
| cgccaacaca gcgtccttgc gccgcttctc tggcagcaac tcgcgcagtc ggcccatcgc | 360 |
| ttcatcggtg ctgctggccg cccagtgctc gttctctggc gtcctgctgg cgtcagcgtt | 420 |
| gggcgtctcg cgctcgcggt aggcgtgctt gagactggcc gccacgttgc ccattttcgc | 480 |
| cagcttcttg catcgcatga tcgcgtatgc cgccatgcct gccccctccct tttggtgtcc | 540 |

```
aaccggctcg acggggggcag cgcaaggcgg tgcctccggc gggccactca atgcttgagt    600
atactcacta gactttgctt cgcaaagtcg tgaccgccta cggcggctgc ggcgccctac    660
gggcttgctc tccgggcttc gccctgcgcg gtcgctgcgc tcccttgcca gcccgtggat    720
atgtggacga tggccgcgag cggccaccgg ctggctcgct tcgctcggcc cgtggacaac    780
cctgctggac aagctgatgg acaggctgcg cctgcccacg agcttgacca cagggattgc    840
ccaccggcta cccagccttc gaccacatac ccaccggctc caactgcgcg gcctgcggcc    900
ttgccccatc aattttttta attttctctg gggaaaagcc tccggcctgc ggcctgcgcg    960
cttcgcttgc cggttggaca ccaagtggaa ggcgggtcaa ggctcgcgca gcgaccgcgc   1020
agcggcttgg ccttgacgcg cctggaacga cccaagccta tgcgagtggg ggcagtcgaa   1080
ggcgaagccc gccgcctgc cccccgagcc tcacggcggc gagtgcgggg gttccaaggg    1140
ggcagcgcca ccttgggcaa ggccgaaggc cgcgcagtcg atcaacaagc cccggagggg   1200 ccacttttg ccggagggggg agccgcgccg aaggcgtggg ggaaccccgc aggggtgccc    1260
ttctttgggc accaaagaac tagatatagg gcgaaatgcg aaagacttaa aaatcaacaa   1320
cttaaaaaag gggggtacgc aacagctcat tgcggcaccc cccgcaatag ctcattgcgt   1380
aggttaaaga aaatctgtaa ttgactgcca cttttacgca acgcataatt gttgtcgcgc   1440
tgccgaaaag ttgcagctga ttgcgcatgg tgccgcaacc gtgcggcacc ctaccgcatg   1500
gagataagca tggccacgca gtccagagaa atcggcattc aagccaagaa caagcccggt   1560
cactgggtgc aaacggaacg caaagcgcat gaggcgtggg ccgggcttat tgcgaggaaa   1620
cccacggcgg caatgctgct gcatcacctc gtggcgcaga tgggccacca gaacgccgtg   1680
gtggtcagcc agaagacact ttccaagctc atcggacgtt ctttgcggac ggtccaatac   1740
gcagtcaagg acttggtggc cgagcgctgg atctccgtcg tgaagctcaa cggccccggc   1800
accgtgtcgg cctacgtggt caatgaccgc gtggcgtggg gccagccccg cgaccagttg   1860
cgcctgtcgg tgttcagtgc cgccgtggtg gttgatcacg acgaccagga cgaatcgctg   1920
ttggggcatg cgaccctgcg ccgcatcccg accctgtatc cgggcgagca gcaactaccg   1980
accggccccg gcgaggagcc gcccagccag cccggcattc cgggcatgga accagacctg   2040
ccagccttga ccgaaacgga ggaatgggaa cggcgcgggc agcagcgcct gccgatgccc   2100
gatgagccgt gttttctgga cgatggcgag ccgttggagc cgccgacacg ggtcacgctg   2160
ccgcgccggt agcacttggg ttgcgcagca acccgtaagt gcgctgttcc agactatcgg   2220
ctgtagccgc ctctagatta attaacctcc agcgcgggga tctcatgctg gagttcttcg   2280
cccaccccca gacaagctgt gaccgtctcc gggagctgca tgtgtcagag gttttcaccg   2340
tcatcaccga aacgcgcgag gcagcagatc aattcgcgcg cgaaggcgaa gcggcatgca   2400
taatgtgcct gtcaaatgga cgaagcaggg attctgcaaa ccctatgcta ctccgtcaag   2460
ccgtcaattg tctgattcgt taccaattat gacaacttga cggctacatc attcactttt   2520
tcttcacaac cggcacggaa ctcgctcggg ctggccccgg tgcattttt aaatacccgc    2580 gagaaataga gttgatcgtc aaaaccaaca ttgcgaccga cggtggcgat aggcatccgg   2640
gtggtgctca aaagcagctt cgcctggctg atacgttggt cctcgcgcca gcttaagacg   2700
ctaatcccta actgctggcg gaaaagatgt gacagacgcg acggcgacaa gcaaacatgc   2760
tgtgcgacgc tggcgatatc aaaattgctg tctgccaggt gatcgctgat gtactgacaa   2820
gcctcgcgta cccgattatc catcggtgga tggagcgact cgttaatcgc ttccatgcgc   2880
```

```
cgcagtaaca attgctcaag cagatttatc gccagcagct ccgaatagcg cccttcccct      2940
tgcccggcgt taatgatttg cccaaacagg tcgctgaaat gcggctggtg cgcttcatcc      3000
gggcgaaaga accccgtatt ggcaaatatt gacggccagt taagccattc atgccagtag      3060
gcgcgcggac gaaagtaaac ccactggtga taccattcgc gagcctccgg atgacgaccg      3120
tagtgatgaa tctctcctgg cgggaacagc aaaatatcac ccggtcggca aacaaattct      3180
cgtccctgat ttttcaccac cccctgaccg cgaatggtga gattgagaat ataacctttc      3240
attcccagcg gtcggtcgat aaaaaaatcg agataaccgt tggcctcaat cggcgttaaa      3300
cccgccacca gatgggcatt aaacgagtat cccggcagca gggatcatt ttgcgcttca       3360 gccatacttt tcatactccc gccattcaga gaagaaacca attgtccata ttgcatcaga      3420
cattgccgtc actgcgtctt ttactggctc ttctcgctaa ccaaaccggt aaccccgctt      3480
attaaaagca ttctgtaaca aagcgggacc aaagccatga caaaaacgcg taacaaaagt      3540
gtctataatc acggcagaaa agtccacatt gattatttgc acggcgtcac actttgctat      3600
gccatagcat ttttatccat aagattagcg gatcctacct gacgcttttt atcgcaactc      3660
tctactgttt ctccatacccc gttttttggg ctagaaataa ttttgagctc aggaaggagc      3720
gaagcatggg ccatcatcat catcatcaca tgagttttga tattgccaaa tacccgaccc      3780
tggcactggt cgactccacc caggagttac gactgttgcc gaaagagagt ttaccgaaac      3840
tctgcgacga actgcgccgc tatttactcg acagcgtgag ccgttccagc gggcacttcg      3900
cctccgggct gggcacggtc gaactgaccg tggcgctgca ctatgtctac aacaccccgt      3960
ttgaccaatt gatttgggat gtggggcatc aggcttatcc gcataaaatt ttgaccggac      4020
gccgcgacaa aatcggcacc atccgtcaga aaggcggtct gcacccgttc ccgtggcgcg      4080
gcgaaagcga atatgacgta ttaagcgtcg ggcattcatc aacctccatc agtgccggaa      4140
ttggtattgc ggttgctgcc gaaaaagaag gcaaaaatcg ccgcaccgtc tgtgtcattg      4200
gcgatggcgc gattaccgca ggcatggcgt ttgaagcgat gaatcacgcg ggcgatatcc      4260
gtcctgatat gctggtgatt ctcaacgaca atgaaatgtc gatttccgaa atgtcggcg      4320 cgctcaacaa ccatctggca cagctgcttt ccggtaagct ttactcttca ctgcgcgaag      4380
gcgggaaaaa agtttttctct ggcgtgccgc caattaaaga gctgctcaaa cgcaccgaag      4440
aacatattaa aggcatggta gtgcctggca cgttgtttga agagctgggc tttaactaca      4500
tcggcccggt ggacggtcac gatgtgctgg ggcttatcac cacgctaaag aacatgcgcg      4560
acctgaaagg cccgcagttc ctgcatatca tgaccaaaaa aggtcgtggt tatgaaccgg      4620
cagaaaaaga cccgatcact ttccacgccg tgcctaaatt tgatccctcc agcggttgtt      4680
tgccgaaaag tagcggcggt ttgccgagct attcaaaaat cttttggcgac tggttgtgcg      4740 aaacggcagc gaaagacaac aagctgatgg cgattactcc ggcgatgcgt gaaggttccg      4800
gcatggtcga gttttcacgt aaaattcccgg atcgctactt cgacgtggca attgccgagc      4860
aacacgcggt gaccttggct gcgggtctgg cgattggtgg gtacaaaccc attgtcgcga      4920
tttactccac tttcctgcaa cgcgcctatg atcaggtgct gcatgacgtg gcgattcaaa      4980
agcttccggt cctgttcgcc atcgaccgcg cgggcattgt tggtgctgac ggtcaaaccc      5040
atcagggtgc ttttgatctc tcttacctgc gctgcatacc ggaaatggtc attatgaccc      5100
cgagcgatga aaacgaatgt cgccagatgc tctataccgg ctatcactat aacgatggcc      5160
cgtcagcggt gcgctacccg cgtggcaacg cggtcggcgt ggaactgacg ccgctggaaa      5220
aactaccaat tggcaaaggc attgtgaagc gtcgtggcga gaaactggcg atccttaact      5280
```

```
ttggtacgct gatgccagaa gcggcgaaag tcgccgaatc gctgaacgcc acgctggtcg   5340
atatgcgttt tgtgaaaccg cttgatgaag cgttaattct ggaaatggcc gccagccatg   5400
aagcgctggt caccgtagaa gaaaacgcca ttatgggcgg cgcaggcagc ggcgtgaacg   5460
aagtgctgat ggcccatcgt aaaccagtac ccgtgctgaa cattggcctg ccggacttct   5520
ttattccgca aggaactcag gaagaaatgc gcgccgaact cggcctcgat gccgctggta   5580
tggaagccaa aatcaaggcc tggctggcat aactttaagg aaggagcgaa gcatgcgttg   5640
tagcgttagc accgaaaatg tgtcgtttac ggaaacggaa accgaagctc gccgcagcgc   5700
aaactatgaa ccgaactcgt gggattacga ttacctcctt agcagcgata cggatgaaag   5760
cattgaagtg tataaagaca aagccaagaa actggaggcc gaagtccgtc gcgaaatcaa   5820
caatgagaaa gcggagtttc ttacgttact ggaattgatc gataacgtgc aacggttagg   5880
cctcggctac cgctttgaga gcgatatccg tggtgcactg gaccgcttcg tatcgtctgg   5940
tggttttgac gccgttacga aaacgagcct gcatggtaca gcattgtctt ttcggctgtt   6000
gcgccagcat ggatttgaag tgtcacagga ggcattttca ggcttcaaag accagaacgg   6060
gaattttttg gagaatttga agaagatat caaagcgatc ttatctctgt atgaggcgtc   6120
atttctcgct ctggaagggg aaaatattct ggacgaagcg aaagtgttcg caatttccca   6180
tctgaaagaa ctttccgaag aaaagattgg gaaagaattg gccgaacagg tgaaccatgc   6240
gctggaactg ccactgcacc gtcgcaccca acgcctcgaa gcggtatggt cgattgaagc   6300
gtatcgcaaa aaagaggatg caaatcaggt tctgctggaa ctggccattc tcgactataa   6360
catgattcag tccgtctatc aacgtgatct gcgcgaaact agtcgttggt ggcgccgtgt   6420
aggacttgcc actaaactgc attttgcacg tgatcgtctg attgagtcgt tctattgggc   6480
ggttggtgta gcgtttgagc cgcagtattc tgattgccgc aatagtgtgg cgaaaatgtt   6540
ctcctttgtg accatcattg acgatattta cgacgtgtat ggcaccctgg atgaactgga   6600
attattcacc gatgcagtag aacgctggga cgtcaacgcg atcaatgatt tgccggatta   6660
catgaaactg tgttttctgg ccctgtataa caccattaac gaaattgcct atgacaacct   6720
caaagacaag ggtgaaaata tcctgcccta tctgactaaa gcttgggctg atctgtgtaa   6780
cgcgttctta caggaagcca aatggctcta caacaagagt acgcctactt tcgatgacta   6840
ctttggcaac gcttggaaaa gctctagcgg cccctttacaa ctggtgttcg cgtatttcgc   6900
cgttgttcag aatatcaaga agaagagat tgagaacctc caaaagtacc acgatacgat   6960
ttcgcgtccg tcacacatct ttcgcctttg caatgatttg gccagtgcat ctgcagagat   7020
tgcgcgcggt gaaactgcca actccgtcag ttgctacatg cgtaccaaag gcatcagcga   7080
ggaactggct accgagtcgg tgatgaactt aatcgatgaa acctggaaga agatgaacaa   7140
agagaaactt ggtggcagtc tgtttgctaa accgttcgtt gagacagcga ttaatctggc   7200
gcgtcaaagc cactgcacct accacaatgg cgatgcccac acatccccag acgaattaac   7260
ccggaaacgt gtcctgagtg tcatcaccga acccattctg ccgttcgaac gctaagcctg   7320
ctaacaaagc ccgaaaggaa gctgagttgg ctgctgccac cgctgagttg gctgctgcca   7380
ccgctgagca ctagtgcggc cgctttgcgc attcacagtt ctccgcaaga attgattggc   7440
tccaattctt ggagtggtga atccgttagc gaggtgccgc cggcttccat tcaggtcgag   7500
gtggcccggc tccatgcacc gcgacgcaac gcggggaggc agacaaggta tagggcggcg   7560
cctacaatcc atgccaaccc gttccatgtg ctcgccgagg cggcataaat cgccgtgacg   7620
```

| | |
|---|---|
| atcagcggtc cagtgatcga agttaggctg gtaagagccg cgagcgatcc ttgaagctgt | 7680 |
| ccctgatggt cgtcatctac ctgcctggac agcatggcct gcaacgcggg catcccgatg | 7740 |
| ccgccggaag cgagaagaat cataatgggg aaggccatcc agcctcgcgt cgcgaacgcc | 7800 |
| agcaagacgt agcccagcgc gtcggccgcc atgccggcga taatggcctg cttctcgccg | 7860 |
| aaacgtttgg tggcgggacc agtgacgaag gcttgagcga gggcgtgcaa gattccgaat | 7920 |
| accgcaagcg acaggccgat catcgtcgcg ctccagcgaa agcggcctc gccgaaaatg | 7980 |
| acccagagcg ctgccggcac ctgtcctacg agttgcatga taaagaagac agtcataagt | 8040 |
| gcggcgacga tagtcatgcc ccgcgcccac cggaaggagc tgactgggtt gaaggctctc | 8100 |
| aagggcatcg gtcgacgctc tcccttatgc gactcctgca ttaggaagca gcccagtagt | 8160 |
| aggttgaggc cgttgagcac cgccgccgca aggaatggtg catgcaagga gatggcgccc | 8220 |
| aacagtcccc cggccacggg gcctgccacc atacccacgc cgaaacaagc gctcatgagc | 8280 |
| ccgaagtggc gagcccgatc ttccccatcg gtgatgtcgg cgataggc gccagcaacc | 8340 |
| gcacctgtgg cgccggtgat gccggccacg atgcgtccgg cgtagaggat ccacaggacg | 8400 |
| ggtgtggtcg ccatgatcgc gtagtcgata gtggctccaa gtagcgaagc gagcaggact | 8460 |
| gggcggcggc caaagcggtc ggacagtgct ccgagaacgg gtgcgcatag aaattgcatc | 8520 |
| aacgcatata gcgctagcag cacgccatag tgactggcga tgctgtcgga atggacgata | 8580 |
| tcccgcaaga ggcccggcag taccggcata accaagccta tgcctacagc atccagggtg | 8640 |
| acggtgccga ggatgacgat gagcgcattg ttagatttca tacacggtgc ctgactgcgt | 8700 |
| tagcaattta actgtgataa actaccgcat taaagcttat cgatgataag ctgtcaaaca | 8760 |
| tgagaattct tgaagacgaa agggcctcgt gatacgccta ttttatagg ttaatgtcat | 8820 |
| gataataatg gtttcttaga cgtcaggtgg cacttttcgg ggaaatgtgc gcgcccgcgt | 8880 |
| tcctgctggc gctgggcctg tttctggcgc tggacttccc gctgttccgt cagcagcttt | 8940 |
| tcgcccacgg ccttgatgat cgcggcggcc ttggcctgca tatcccgatt caacggcccc | 9000 |
| agggcgtcca gaacgggctt caggcgctcc gaaggtctc gggccgtctc ttgggcttga | 9060 |
| tcggcctct tgcgcatctc acgcgctcct gcggcggcct gtagggcagg ctcatacccc | 9120 |
| tgccgaaccg cttttgtcag ccggtcggcc acggcttccg gcgtctcaac gcgctttgag | 9180 |
| attcccagct tttcggccaa tccctgcggt gcataggcgc gtggctcgac cgcttgcggg | 9240 |
| ctgatggtga cgtggcccac tggtggccgc tccagggcct cgtagaacgc ctgaatgcgc | 9300 |
| gtgtgacgtg ccttgctgcc | 9320 |

<210> SEQ ID NO 9
<211> LENGTH: 9362
<212> TYPE: DNA
<213> ORGANISM: artificial sequence
<220> FEATURE:
<223> OTHER INFORMATION: Synthetic

<400> SEQUENCE: 9

| | |
|---|---|
| ctcgatgccc cgttgcagcc ctagatcggc cacagcggcc gcaaacgtgg tctggtcgcg | 60 |
| ggtcatctgc gctttgttgc cgatgaactc cttggccgac agcctgccgt cctgcgtcag | 120 |
| cggcaccacg aacgcggtca tgtgcgggct ggtttcgtca cggtggatgc tggccgtcac | 180 |
| gatgcgatcc gccccgtact tgtccgccag ccacttgtgc gccttctcga agaacgccgc | 240 |
| ctgctgttct tggctggccg acttccacca ttccgggctg gccgtcatga cgtactcgac | 300 |
| cgccaacaca gcgtccttgc gccgcttctc tggcagcaac tcgcgcagtc ggcccatcgc | 360 |

```
ttcatcggtg ctgctggccg cccagtgctc gttctctggc gtcctgctgg cgtcagcgtt      420
gggcgtctcg cgctcgcggt aggcgtgctt gagactggcc gccacgttgc ccattttcgc      480
cagcttcttg catcgcatga tcgcgtatgc cgccatgcct gcccctccct tttggtgtcc      540
aaccggctcg acggggcag cgcaaggcgg tgcctccggc gggccactca atgcttgagt       600
atactcacta gactttgctt cgcaaagtcg tgaccgccta cggcggctgc ggcgccctac      660
gggcttgctc tccgggcttc gcccgcgcg gtcgctgcgc tcccttgcca gcccgtggat      720
atgtggacga tggccgcgag cggccaccgg ctggctcgct tcgctcggcc cgtggacaac     780
cctgctggac aagctgatgg acaggctgcg cctgcccacg agcttgacca cagggattgc      840
ccaccggcta cccagccttc gaccacatac ccaccggctc caactgcgcg gcctgcggcc      900
ttgccccatc aatttttta attttctctg gggaaaagcc tccggcctgc ggcctgcgcg      960
cttcgcttgc cggttggaca ccaagtggaa ggcgggtcaa ggctcgcgca gcgaccgcgc     1020
agcggcttgg ccttgacgcg cctggaacga cccaagccta tgcgagtggg ggcagtcgaa     1080
ggcgaagccc gcccgcctgc ccccgagcc tcacggcggc gagtgcgggg gttccaaggg     1140
ggcagcgcca ccttgggcaa ggccgaaggc cgcgcagtcg atcaacaagc cccgaggggg     1200 ccacttttg ccggaggggg agccgcgccg aaggcgtggg ggaaccccgc aggggtgccc      1260
ttctttgggc accaaagaac tagatatagg gcgaaatgcg aaagacttaa aaatcaacaa     1320 cttaaaaag ggggtacgc aacagctcat tgcggcaccc cccgcaatag ctcattgcgt      1380
aggttaaaga aaatctgtaa ttgactgcca cttttacgca acgcataatt gttgtcgcgc     1440
tgccgaaaag ttgcagctga ttgcgcatgg tgccgcaacc gtgcggcacc ctaccgcatg     1500
gagataagca tggccacgca gtccagagaa atcggcattc aagccaagaa caagcccggt     1560
cactgggtgc aaacggaacg caaagcgcat gaggcgtggg ccgggcttat tgcgaggaaa     1620
cccacggcgg caatgctgct gcatcacctc gtggcgcaga tgggccacca gaacgccgtg     1680
gtggtcagcc agaagacact ttccaagctc atcggacgtt ctttgcggac ggtccaatac     1740
gcagtcaagg acttggtggc cgagcgctgg atctccgtcg tgaagctcaa cggccccggc     1800
accgtgtcgg cctacgtggt caatgaccgc gtggcgtggg gccagccccg cgaccagttg     1860
cgcctgtcgg tgttcagtgc cgccgtggtg gttgatcacg acgaccagga cgaatcgctg     1920
ttggggcatg gcgacctgcg ccgcatcccg accctgtatc cgggcgagca gcaactaccg     1980
accggccccg gcgaggagcc gcccagccag cccggcattc cgggcatgga accagacctg     2040
ccagccttga ccgaaacgga ggaatgggaa cggcgcgggc agcagcgcct gccgatgccc     2100
gatgagccgt gttttctgga cgatggcgag ccgttggagc cgccgacacg ggtcacgctg     2160
ccgcgccggt agcactgggg ttgcgcagca accgtaagt gcgctgttcc agactatcgg     2220
ctgtagccgc ctctagatta attaacctcc agcgcgggga tctcatgctg gagttcttcg     2280
cccaccccca gacaagctgt gaccgtctcc gggagctgca tgtgtcagag gttttcaccg     2340
tcatcaccga aacgcgcgag gcagcagatc aattcgcgcg cgaaggcgaa gcggcatgca     2400
taatgtgcct gtcaaatgga cgaagcaggg attctgcaaa ccctatgcta ctccgtcaag     2460
ccgtcaattg tctgattcgt taccaattat gacaacttga cggctacatc attcactttt     2520
tcttcacaac cggcacggaa ctcgctcggg ctggccccgg tgcattttt aaatacccgc      2580 gagaaataga gttgatcgtc aaaaccaaca ttgcgaccga cggtggcgat aggcatccgg     2640
gtggtgctca aaagcagctt cgcctggctg atacgttggt cctcgcgcca gcttaagacg     2700
```

| | |
|---|---|
| ctaatccota actgctggcg aaaagatgt gacagacgcg acggcgacaa gcaaacatgc | 2760 |
| tgtgcgacgc tggcgatatc aaaattgctg tctgccaggt gatcgctgat gtactgacaa | 2820 |
| gcctcgcgta cccgattatc catcggtgga tggagcgact cgttaatcgc ttccatgcgc | 2880 |
| cgcagtaaca attgctcaag cagatttatc gccagcagct ccgaatagcg cccttcccct | 2940 |
| tgcccggcgt taatgatttg cccaaacagg tcgctgaaat gcggctggtg cgcttcatcc | 3000 |
| gggcgaaaga accccgtatt ggcaaatatt gacggccagt taagccattc atgccagtag | 3060 |
| gcgcgcggac gaaagtaaac ccactggtga taccattcgc gagcctccgg atgacgaccg | 3120 |
| tagtgatgaa tctctcctgg cgggaacagc aaaatatcac ccggtcggca aacaaattct | 3180 |
| cgtccctgat ttttcaccac ccctgaccg cgaatggtga gattgagaat ataacctttc | 3240 |
| attcccagcg gtcggtcgat aaaaaaatcg agataaccgt tggcctcaat cggcgttaaa | 3300 |
| cccgccacca gatgggcatt aaacgagtat cccggcagca ggggatcatt ttgcgcttca | 3360 |
| gccatacttt tcatactccc gccattcaga aagaaaacca attgtccata ttgcatcaga | 3420 |
| cattgccgtc actgcgtctt ttactggctc ttctcgctaa ccaaaccggt aaccccgctt | 3480 |
| attaaaagca ttctgtaaca aagcgggacc aaagccatga caaaaacgcg taacaaaagt | 3540 |
| gtctataatc acggcagaaa agtccacatt gattatttgc acggcgtcac actttgctat | 3600 |
| gccatagcat ttttatccat aagattagcg gatcctacct gacgcttttt atcgcaactc | 3660 |
| tctactgttt ctccataccc gtttttggg ctagaaataa ttttgagctc aggaaggagc | 3720 |
| gaagcatggg ccatcatcat catcatcaca tgctggatct gctgtcgatc caggacccgt | 3780 |
| ccttcctgaa gaacatgagc atcgacgagc tggagaagct gtccgacgag atccgccagt | 3840 |
| tcctgatcac ctcgctcagc gcctcgggcg gccatatcgg ccccaacctg gcgtcgtgg | 3900 |
| aactgacggt ggccctgcac aaggaattca actcgccgaa ggacaagttc ctgtgggatg | 3960 |
| tgggccatca gtcgtatgtc cacaagctgc tgaccggccg cggcaaggaa ttcgccacgc | 4020 |
| tgcgccaata caagggcctg tgcggctttc cgaagcgctc ggaatcggaa catgacgtct | 4080 |
| gggaaacggg ccacagctcg accagcctga gcggcgccat gggtatggcg ccgcccgcg | 4140 |
| acatcaaggg cacggacgag tatatcatcc cgatcatcgg cgacggcgcc ctgacgggcg | 4200 |
| gcatggcgct cgaagccctc aaccacatcg gtgatgagaa gaaggacatg atcgtgatcc | 4260 |
| tgaacgacaa cgaaatgagc atcgcgccga atgtgggcgc cattcattcg atgctgggcc | 4320 |
| gcctgcgtac cgcgggtaag tatcagtggg tgaaggatga gctggagtac ctgttcaaga | 4380 |
| agatcccggc ggtgggcggc aagctggccg ccacggcgga gcgcgtgaag gactccctga | 4440 |
| agtacatgct cgtcagcggc atgttttcg aggaactggg cttcacctat ctgggcccgg | 4500 |
| tggatggcca ctcctaccat gagctcatcg aaaatctgca atacgccaaa aagacgaagg | 4560 |
| gccccgtcct cctccacgtc atcacgaaga agggcaaggg ctacaagccc gccgaaaccg | 4620 |
| acaccatcgg cacgtggcat ggcaccggcc cctacaagat caacacgggc gactttgtga | 4680 |
| agccgaaggc cgccgcgccg tcctggagcg gcctggtgag cggcaccgtc cagcgtatgg | 4740 |
| cccgcgaaga tggccggatc gtggcgatca ccccggcgat gccggtcggc agcaagctgg | 4800 |
| aaggcttcgc caaggaattc ccggaccgca tgttcgacgt gggcatcgcg gagcagcacg | 4860 |
| ccgccacgat ggcggcggcc atggccatgc agggtatgaa gccgttcctg gcgatctact | 4920 |
| ccacgttcct gcagcgcgcc tacgaccagg tcgtgcacga tatctgccgc cagaatgcga | 4980 |
| atgtgttcat cggcatcgac cgcgcgggcc tggtgggcgc ggacggcgaa acccaccagg | 5040 |
| gcgtgttcga tatcgcgttt atgcgtcaca tcccgaacat ggtcctgatg atgccgaagg | 5100 |

-continued

```
atgagaacga aggccagcac atggtccata ccgccctgag ctatgatgaa ggcccgatcg    5160
ccatgcgctt cccccgtggt aacggcctgg gtgtgaagat ggacgagcag ctcaagacca    5220
tcccgattgg cacctgggaa gtgctgcgcc cgggtaatga cgcggtgatc ctgaccttcg    5280
gcacgaccat cgagatggcc atcgaagcgg ccgaggaact gcagaaggaa ggcctgtcgg    5340
tgcgcgtcgt caacgcccgc ttcattaagc cgatcgacga aagatgatg aagtcgatcc    5400 tgaaggaggg cctgcccatc ctgaccatcg aagaagccgt gctggagggc ggcttcggtt    5460
cgtcgatcct ggaattcgcg cacgaccagg gcgagtacca cacgccgatc gaccgcatgg    5520
gcatcccgga ccggttcatc gagcacggct cggtcaccgc cctgctggaa gaaattggcc    5580
tcaccaagca acaagtggcc aaccggattc ggctcctgat gccccccaag acccacaagg    5640
gcatcggctc gtgactttaa ggaaggagcg aagcatgcgt gtagcgtta gcaccgaaaa    5700 tgtgtcgttt acggaaacgg aaaccgaagc tcgccgcagc gcaaactatg aaccgaactc    5760
gtgggattac gattacctcc ttagcagcga tacggatgaa agcattgaag tgtataaaga    5820
caaagccaag aaactggagg ccgaagtccg tcgcgaaatc aacaatgaga agcggagtt    5880 tcttacgtta ctggaattga tcgataacgt gcaacggtta ggcctcggct accgctttga    5940
gagcgatatc cgtggtgcac tggaccgctt cgtatcgtct ggtggttttg acgccgttac    6000
gaaaacgagc ctgcatggta cagcattgtc ttttcggctg ttgcgccagc atggatttga    6060
agtgtcacag gaggcatttt caggcttcaa agaccagaac gggaattttt tggagaattt    6120
gaaagaagat atcaaagcga tcttatctct gtatgaggcg tcatttctcg ctctggaagg    6180
ggaaaatatt ctggacgaag cgaaagtgtt cgcaatttcc catctgaaag aactttccga    6240
agaaaagatt gggaaagaat tggccgaaca ggtgaaccat cgcgctggaa ctgccactgca    6300 ccgtcgcacc caacgcctcg aagcggtatg gtcgattgaa gcgtatcgca aaaagagga    6360 tgcaaatcag gttctgctgg aactggccat tctcgactat aacatgattc agtccgtcta    6420
tcaacgtgat ctgcgcgaaa ctagtcgttg gtggcgccgt gtaggacttg ccactaaact    6480
gcattttgca cgtgatcgtc tgattgagtc gttctattgg gcggttggtg tagcgtttga    6540
gccgcagtat tctgattgcc gcaatagtgt ggcgaaaatg ttctcctttg tgaccatcat    6600
tgacgatatt tacgacgtgt atggcaccct ggatgaactg gaattattca ccgatgcagt    6660
agaacgctgg gacgtcaacg cgatcaatga tttgccggat tacatgaaac tgtgtttct    6720 ggccctgtat aacaccatta acgaaattgc ctatgacaac ctcaaagaca agggtgaaaa    6780
tatcctgccc tatctgacta aagcttgggc tgatctgtgt aacgcgttct acaggaagc    6840 caaatggctc tacaacaaga gtacgcctac tttcgatgac tactttggca acgcttggaa    6900
aagctctagc ggccctttac aactggtgtt cgcgtatttc gccgttgttc agaatatcaa    6960
gaaagaagag attgagaacc tccaaaagta ccacgatacg atttcgcgtc cgtcacacat    7020
ctttcgcctt tgcaatgatt tggccagtgc atctgcagag attgcgcgcg gtgaaactgc    7080
caactccgtc agttgctaca tgcgtaccaa aggcatcagc gaggaactgg ctaccgagtc    7140
ggtgatgaac ttaatcgatg aaacctggaa gaagatgaac aaagagaaac ttggtggcag    7200
tctgtttgct aaaccgttcg ttgagacagc gattaatctg gcgcgtcaaa gccactgcac    7260
ctaccacaat ggcgatgccc acacatcccc agacgaatta acccggaaac gtgtcctgag    7320
tgtcatcacc gaacccattc tgccgttcga acgctaagcc tgctaacaaa gcccgaaagg    7380
aagctgagtt ggctgctgcc accgctgagt tggctgctgc caccgctgag cactagtgcg    7440
```

```
gccgctttgc gcattcacag ttctccgcaa gaattgattg gctccaattc ttggagtggt    7500
gaatccgtta gcgaggtgcc gccggcttcc attcaggtcg aggtggcccg gctccatgca    7560
ccgcgacgca acgcggggag gcagacaagg tatagggcgg cgcctacaat ccatgccaac    7620
ccgttccatg tgctcgccga ggcggcataa atcgccgtga cgatcagcgg tccagtgatc    7680
gaagttaggc tggtaagagc cgcgagcgat ccttgaagct gtccctgatg gtcgtcatct    7740
acctgcctgg acagcatggc ctgcaacgcg ggcatcccga tgccgccgga agcgagaaga    7800
atcataatgg ggaaggccat ccagcctcgc gtcgcgaacg ccagcaagac gtagcccagc    7860
gcgtcggccg ccatgccggc gataatggcc tgcttctcgc cgaaacgttt ggtggcggga    7920
ccagtgacga aggcttgagc gagggcgtgc aagattccga ataccgcaag cgacaggccg    7980
atcatcgtcg cgctccagcg aaagcggtcc tcgccgaaaa tgcccagag cgctgccggc    8040
acctgtccta cgagttgcat gataaagaag acagtcataa gtgcggcgac gatagtcatg    8100
ccccgcgccc accggaagga gctgactggg ttgaaggctc tcaagggcat cggtcgacgc    8160
tctcccttat gcgactcctg cattaggaag cagcccagta gtaggttgag gccgttgagc    8220
accgccgccg caaggaatgg tgcatgcaag gagatggcgc ccaacagtcc cccggccacg    8280
gggcctgcca ccatacccac gccgaaacaa gcgctcatga gcccgaagtg gcgagcccga    8340
tcttccccat cggtgatgtc ggcgatatag gcgccagcaa ccgcacctgt ggcgccggtg    8400
atgccggcca cgatgcgtcc ggcgtagagg atccacagga cgggtgtggt cgccatgatc    8460
gcgtagtcga tagtggctcc aagtagcgaa gcgagcagga ctgggcggcg gccaaagcgg    8520
tcggacagtg ctccgagaac gggtgcgcat agaaattgca tcaacgcata tagcgctagc    8580
agcacgccat agtgactggc gatgctgtcg gaatggacga tatcccgcaa gaggcccggc    8640
agtaccggca taaccaagcc tatgcctaca gcatccaggg tgacggtgcc gaggatgacg    8700
atgagcgcat tgttagattt catacacggt gcctgactgc gttagcaatt taactgtgat    8760
aaactaccgc attaaagctt atcgatgata agctgtcaaa catgagaatt cttgaagacg    8820
aaagggcctc gtgatacgcc tatttttata ggttaatgtc atgataataa tggtttctta    8880
gacgtcaggt ggcactttc ggggaaatgt gcgcgcccgc gttcctgctg cgctgggcc    8940
tgtttctggc gctggacttc ccgctgttcc gtcagcagct tttcgcccac ggccttgatg    9000
atcgcggcgg ccttggcctg catatcccga ttcaacggcc ccaggcgtc cagaacgggc    9060
ttcaggcgct cccgaaggtc tcgggccgtc tcttgggctt gatcggcctt cttgcgcatc    9120
tcacgcgctc ctgcggcggc ctgtagggca ggctcatacc cctgccgaac cgcttttgtc    9180
agccggtcgg ccacggcttc cggcgtctca acgcgctttg agattcccag ctttcggcc    9240
aatccctgcg gtgcatatggc gcgtggctcg accgcttgcg ggctgatggt gacgtggccc    9300
actggtggcc gctccagggc ctcgtagaac gcctgaatgc gcgtgtgacg tgccttgctg    9360
cc                                                                   9362
```

<210> SEQ ID NO 10
<211> LENGTH: 32
<212> TYPE: DNA
<213> ORGANISM: artificial sequence
<220> FEATURE:
<223> OTHER INFORMATION: Synthetic

<400> SEQUENCE: 10

```
ggaaggagcg aagcatgcgt tgtagcgtta gc                                    32
```

<210> SEQ ID NO 11
<211> LENGTH: 38
<212> TYPE: DNA
<213> ORGANISM: artificial sequence
<220> FEATURE:
<223> OTHER INFORMATION: Synthetic

<400> SEQUENCE: 11
gggctttgtt agcaggctta gcgttcgaac ggcagaat                           38

<210> SEQ ID NO 12
<211> LENGTH: 21
<212> TYPE: DNA
<213> ORGANISM: artificial sequence
<220> FEATURE:
<223> OTHER INFORMATION: Synthetic

<400> SEQUENCE: 12
gcctgctaac aaagcccgaa a                                             21

<210> SEQ ID NO 13
<211> LENGTH: 20
<212> TYPE: DNA
<213> ORGANISM: artificial sequence
<220> FEATURE:
<223> OTHER INFORMATION: Synthetic

<400> SEQUENCE: 13
gcttcgctcc ttccttaaag                                               20

<210> SEQ ID NO 14
<211> LENGTH: 19
<212> TYPE: DNA
<213> ORGANISM: artificial sequence
<220> FEATURE:
<223> OTHER INFORMATION: Synthetic

<400> SEQUENCE: 14
gccgccctat accttgtct                                                19

<210> SEQ ID NO 15
<211> LENGTH: 20
<212> TYPE: DNA
<213> ORGANISM: artificial sequence
<220> FEATURE:
<223> OTHER INFORMATION: Synthetic

<400> SEQUENCE: 15
acggcgtcac actttgctat                                               20

<210> SEQ ID NO 16
<211> LENGTH: 20
<212> TYPE: DNA
<213> ORGANISM: artificial sequence
<220> FEATURE:
<223> OTHER INFORMATION: Synthetic

<400> SEQUENCE: 16
cgcgtcgcga acgccagcaa                                               20

<210> SEQ ID NO 17
<211> LENGTH: 20
<212> TYPE: DNA
<213> ORGANISM: artificial sequence
<220> FEATURE:
<223> OTHER INFORMATION: Synthetic

```
<400> SEQUENCE: 17
acggggcctg ccaccatacc                                               20

<210> SEQ ID NO 18
<211> LENGTH: 20
<212> TYPE: DNA
<213> ORGANISM: artificial sequence
<220> FEATURE:
<223> OTHER INFORMATION: Synthetic

<400> SEQUENCE: 18
cttatcgatg ataagctgtc                                               20

<210> SEQ ID NO 19
<211> LENGTH: 20
<212> TYPE: DNA
<213> ORGANISM: artificial sequence
<220> FEATURE:
<223> OTHER INFORMATION: Synthetic

<400> SEQUENCE: 19
cagccctaga tcggccacag                                               20

<210> SEQ ID NO 20
<211> LENGTH: 20
<212> TYPE: DNA
<213> ORGANISM: artificial sequence
<220> FEATURE:
<223> OTHER INFORMATION: Synthetic

<400> SEQUENCE: 20
tgcctgcccc tcccttttgg                                               20

<210> SEQ ID NO 21
<211> LENGTH: 20
<212> TYPE: DNA
<213> ORGANISM: artificial sequence
<220> FEATURE:
<223> OTHER INFORMATION: Synthetic

<400> SEQUENCE: 21
gcggcgagtg cggggttcc                                                20

<210> SEQ ID NO 22
<211> LENGTH: 20
<212> TYPE: DNA
<213> ORGANISM: artificial sequence
<220> FEATURE:
<223> OTHER INFORMATION: Synthetic

<400> SEQUENCE: 22
ggaaacccac ggcggcaatg                                               20

<210> SEQ ID NO 23
<211> LENGTH: 24
<212> TYPE: DNA
<213> ORGANISM: artificial sequence
<220> FEATURE:
<223> OTHER INFORMATION: Synthetic

<400> SEQUENCE: 23
atcggctgta gccgcctcta gatt                                          24

<210> SEQ ID NO 24
<211> LENGTH: 20
```

```
<212> TYPE: DNA
<213> ORGANISM: artificial sequence
<220> FEATURE:
<223> OTHER INFORMATION: Synthetic

<400> SEQUENCE: 24
agtaacaatt gctcaagcag                                                    20

<210> SEQ ID NO 25
<211> LENGTH: 20
<212> TYPE: DNA
<213> ORGANISM: artificial sequence
<220> FEATURE:
<223> OTHER INFORMATION: Synthetic

<400> SEQUENCE: 25
attcagagaa gaaaccaatt                                                    20

<210> SEQ ID NO 26
<211> LENGTH: 78
<212> TYPE: DNA
<213> ORGANISM: artificial sequence
<220> FEATURE:
<223> OTHER INFORMATION: Synthetic

<400> SEQUENCE: 26
gctagaaata attttgagct caggaaggag cgaagcatgg gccatcatca tcatcatcac        60
atgagttttg atattgcc                                                      78

<210> SEQ ID NO 27
<211> LENGTH: 38
<212> TYPE: DNA
<213> ORGANISM: artificial sequence
<220> FEATURE:
<223> OTHER INFORMATION: Synthetic

<400> SEQUENCE: 27
gcttcgctcc ttccttaaag ttatgccagc caggcctt                                38

<210> SEQ ID NO 28
<211> LENGTH: 81
<212> TYPE: DNA
<213> ORGANISM: artificial sequence
<220> FEATURE:
<223> OTHER INFORMATION: Synthetic

<400> SEQUENCE: 28
gctagaaata attttgagct caggaaggag cgaagcatgg gccatcatca tcatcatcac        60
atgctggatc tgctgtcgat c                                                  81

<210> SEQ ID NO 29
<211> LENGTH: 38
<212> TYPE: DNA
<213> ORGANISM: artificial sequence
<220> FEATURE:
<223> OTHER INFORMATION: Synthetic

<400> SEQUENCE: 29
gcttcgctcc ttccttaaag tcacgagccg atgcccctt                               38

<210> SEQ ID NO 30
<211> LENGTH: 19
<212> TYPE: DNA
<213> ORGANISM: artificial sequence
<220> FEATURE:
```

```
<223> OTHER INFORMATION: Synthetic

<400> SEQUENCE: 30
cactttgcta tgccatagc                                                 19

<210> SEQ ID NO 31
<211> LENGTH: 20
<212> TYPE: DNA
<213> ORGANISM: artificial sequence
<220> FEATURE:
<223> OTHER INFORMATION: Synthetic

<400> SEQUENCE: 31
ctgcggcgag cttcggtttc                                                20

<210> SEQ ID NO 32
<211> LENGTH: 22
<212> TYPE: DNA
<213> ORGANISM: artificial sequence
<220> FEATURE:
<223> OTHER INFORMATION: Synthetic

<400> SEQUENCE: 32
gactccctga agtacatgct cg                                             22
```